(12) United States Patent
de Lange et al.

(10) Patent No.: US 7,507,806 B2
(45) Date of Patent: Mar. 24, 2009

(54) NUCLEIC ACID SEQUENCES OF HUMAN RIF1

(75) Inventors: Titia de Lange, New York, NY (US); Joshua Silverman, New York, NY (US)

(73) Assignee: The Rockefeller University, New York, NY (US)

( * ) Notice: Subject to any disclaimer, the term of this patent is extended or adjusted under 35 U.S.C. 154(b) by 233 days.

(21) Appl. No.: 11/203,806

(22) Filed: Aug. 15, 2005

(65) Prior Publication Data

US 2006/0051737 A1  Mar. 9, 2006

Related U.S. Application Data

(60) Provisional application No. 60/601,405, filed on Aug. 13, 2004.

(51) Int. Cl.
*C07H 21/04* (2006.01)
*C12N 15/00* (2006.01)

(52) U.S. Cl. .................. 536/23.5; 536/23.1; 435/320.1

(58) Field of Classification Search .................. None
See application file for complete search history.

(56) References Cited

OTHER PUBLICATIONS

Nichols et al. Characterization of a new human diploid cell strain, IMR-90. Science, vol. 196, No. 4285, pp. 60-63, Apr. 1977.*

* cited by examiner

*Primary Examiner*—Celine X Qian
*Assistant Examiner*—Jennifer Dunston
(74) *Attorney, Agent, or Firm*—Klauber & Jackson LLC

(57) ABSTRACT

The present invention relates to human Rif1 (hRif1) nucleic acid sequences and human Rif1 amino acid sequences encoded therefrom. The invention also encompasses antibodies that are immunologically specific for human Rif1 polypeptides. Also included in the present invention are methods directed to detecting Rif1 foci formed in response to various treatments that induce DNA damage. The formation of foci comprising Rif1 in response to DNA damage serves as a positive indicator of the presence of wild type ATM kinase activity in a cell, whereas the absence of detectable Rif1 foci under such circumstances serves to identify a cell with reduced ATM kinase activity. Modulators of ATM kinase activity and/or Rif1 activity and methods for identifying such modulators are also included in the present invention.

3 Claims, 15 Drawing Sheets
(5 of 15 Drawing Sheet(s) Filed in Color)

FIG. 1A  Rif1
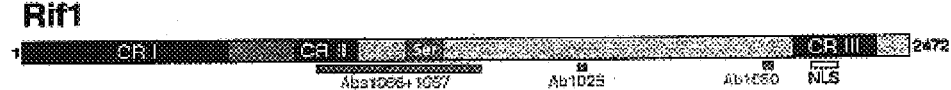
FIG. 1B
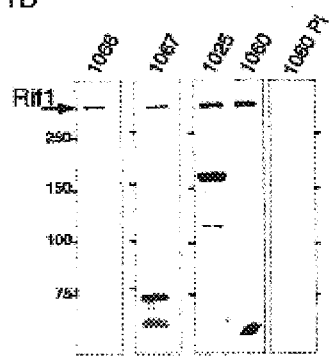

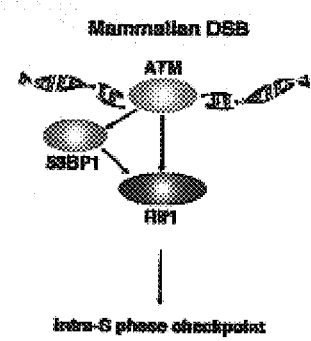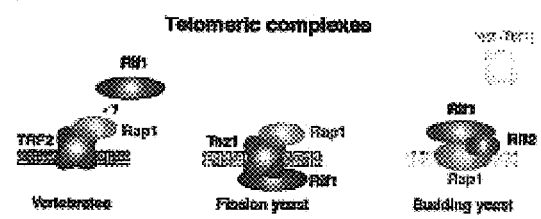
FIG. 7A
FIG. 7B

FIG 6B

Human Rif1 aa 1-1081 (CRI-II)
S. cerevisiae Rif1 aa 172-1219

Human Rif1 aa 2144-2365 (CRIII)
S. cerevisiae Rif1 aa 1345-1579

FIG 9

GGTCTAGGAGGGAGCGCGCCgcacgcgtgagtaaacagccggagctgggaaagtcgagctct
ggcagcgtctgggtgctgaggggcagaggcggagagaaccctgtcctgatcttcctagggtggccgacatgac
ggccaggggtcagagcccctcgcgccgctgttggagactttggaagacccttctgcctcccatggagggcag
actgacgcttacctgactctgaccagtcgtatgactggagaagaaggaaaagaagtaattacagaaattgaga
aaaaacttcctcggctgtacaaagttttaaagactcacatttccagtcaaaactcggagctgagtagtgctgctcta
caagccctggggttttgcttatataatcccaaaattacctcagaattatcagaggcagatgctctagaattgctttca
aaattgaatgataccattaagaattcagacaaaaatgtacgtactagagcactttgggtgatatctaagcagaca
tttccctctgaagtggttggcaaaatggtatccagtataattgattcattagaaatactgtttaacaaaggagagac
gcattctgctgttgttgattttgaagcattaaatgttatcgtaaggctaattgaacaagccccaattcaaatgggaga
agaggcagtgaggtgggcaaaactggtcatacctttagtggttcattcagcacaaaaggtacatttgcggggag
caactgctctggagatgggaatgccattattgcttcagaaacagcaagaaatagcatctattacggagcagcta
tgactactaaattaatctcagaacttcagaagctatttatgagtaaaaatgagacttacgtgttaaaattatggccttt
gtttgtcaaactacttggaaggaccttgcatcgaagtgggagtttcatcaattctctcttgcaactagaagaacttgg
atttcgtagtggagcacccatgattaaaaagatagcttttattgcttggaagagtttaatagataattttgctttaaatc
cagatatactatgtagtgcaaaaagactcaagttgttaatgcagcctttgagttccatccatgtgagaacagaaac
tctagcattaacaaaactagaagtctggtggtatttactgatgagacttggacctcatcttcctgctaattttgaacag
gtttgtgtgcctctgattcaaagtacaataagcattgattctaatgcctcacctcagggcaattcgtgtcatgtagcta
catctccaggtttaaatcctatgactcctgtacacaaaggtgcttcctccccgtacggagccccgggaactccccg
aatgaacctgagttcgaatttaggtggaatggccacaatcccatccattcaacttttgggacttgaaatgttgcttca
tttcttgttgggtccagaagccttgagttttgctaagcaaaataaacttgtgctgagcttagagccattggaacatcc
gttaatcagcagcccttccttttttccaaacatgcaaatacacttatcactgctgttcatgatagctttgttgcagttgg
aaaagatgccccccgatgtggttgtcagtgctatctggaaggagctaattagcttggtgaagtcagttactgaatca
ggtaacaaaaaagagaaaccaggttctgaagttttgactctcttattaaagtctttggaaagcatagtaaagtctg
aagtatttcctgtatcaaaaacgctggtcctcatggaaattacaattaaaggacttcctcagaaagtattaggttca
ccagcatatcaggttgctaatatggatattcttaatggaactccagctttgttcttaattcaattaattttcaacaatttctt
ggaatgtggtgtatcagatgaaaggttctttctcagtttggaatcacttgtaggctgtgttctttctggtccaacttcacc
actagctttcagtgactcagttttaaatgttattaatcaaaatgcaaagcagttggaaaataaggagcatctctgga
aaatgtggagtgttatagtcaccccattaactgaattgattaatcagaccaatgaagtaaatcaaggtgatgcctt
agaacataattttagtgccatctatggtgcattgactttaccagtaaaccacatttttttcagaacagagatttccagtg
gccaccatgaagactttgcttagaacttggtcagaattatatagagcatttgctcgttgtgctgctttggtggcaaca
gcagaagagaacttgtgctgtgaggaactttcttccaagataatgtccagtttggaagatgaaggcttttctaatttg
ttgttcgtggatagaattatttatattattactgtaatggttgattgcattgacttctcaccatataatattaaatatcagcc
caaagttaaatcaccacagagaccttcagattggtccaaaaagaagaatgagccctagggaaattgacttct
tatttaaacttattgtgaaagtgatctattctttccacacactgagcttcaaggaagcacattctgatacccctcttcact
attggcaactcaatcaccggcattatttccagtgtacttgggcatatttctttgccttctatgatccgaaaaatatttgca
actttaacaagacctctggcattattttatgaaaactcaaagcttgatgaagttcctaaagtatatagttgtctgaaca
acaagttagaaaagctactgggagaaattattgcttgtctgcaattcagctacaccggaacttatgatagtgaactt
cttgaacaactctccccactattatgcataatatttctgcacaagaataaacagattcgaaaacagagtgctcagtt
ctggaatgccacttttgccaaagtgatgatgttggtttatcctgaagagttaaaaccagtactaacacaagccaaa
caaaaatttctgctcctgttgcctggtttggaaactgttgaaatgatggaggaatccagtggaccatattctgatgga
acagaaaattcacaactaaatgtgaagataagtggcatggagagaaaatcaaatggaaaagagattcatttt
tggcacaaacaaagaataaaaaagaaaatatgaaaccagcagccaaactgaaacttgaatcttcgtctttaaa
agtaaagggtgaaattcttttggaagaggaaaagtctactgactttgtgtttatacctccagaaggaaaagatgca
aaggaaagaatattaactgatcatcaaaaagaagttctcaaaacaaagcggtgtgatattcctgccatgtataat
aatctggatgtttcccaagatacctttatttactcagtatagtcaggaagagcctatggaaattcctactttaaccaga

FIG. 9 continued aaaccaaaggaggattctaagatgatgattacggaggagcaaatggacagtgacattgtcattcctcaagatgt
cacggaagactgtggtatggctgaacatcttgaaaagtcctcccttt cgaataatgagtgtggttctcttgacaaaa
ccagtccagaaatgtcaaacagtaataatgatgaaagaaaaaagctttaatttcatcaaggaaaacatcaac
tgaatgtgcatctagtacagaaaattctttcgttgtcagcagtagttcagtttctaataccactgttgctggaactcccc
catccctacaagtcggaggcaaacctttattactttggagaagtttgatggttcagaaaatagacctttagtccat
cccccttgaataatatttcatcaactgttacagtgaaaaataaccaggaaccatgattaaaacagattttctacc
aaaagcaaagcaaagagaagggacttttt caaaatctgattctgaaaaaatagtgaatggaactaagagatca
agccggagagctggtaaagctgaacaaacagggaataaaaggtctaagcccttaatgagatctgagccgga
gaaaaatactgaggaatctgttgaaggcattgtagtcttagaaaataaccca cctggtttgcttaatcaaacaga
atgtgtgtcagataatcaggttcatctttctgaatctacaatggagcatgacaatacaaagcttaaagcagcaaca
gtggaaaatgctgtattattggaaactaatactgtagaggagaaaaatgtagaaattaatttggaatccaaagag
aatacaccccagtagtaatatcagcagatcaaatggtaaatgaggatagtcaggttcagataactccaaatca
gaaaacccttagacggtcttcaaggcgacgttcagaagtagtagagtctaccactgaaagccaagataagga
aaatagtcatcaaaaaaaggaacgacgtaaggaagaagaaaaacctcttcagaagagtccattgcatataa
aagatgatgtgttacctaaacaaaaactgattgctgaacaaactctacaggagaatttaattgagaaaggaagt
aatttacatgagaagactcttggggaaactagtgctaatgcagaaactgaacaaaataaaaaaaaggcagac
cctgagaacattaagtctgagggggatggtacccaggacattgtagataagtcctctgagaaactagtcagagg
ccgaacacggtatcaaactagaagagcatctcagggtttgctttccagcattgaaaactcagaatctgatagttc
ggaggcaaaagaagaaggttctaggaagaagagatctggaaaatggaaaaacaaaagcaatgaaagtgtt
gacattcaagatcaagaagagaaagtggtgaaacaggaatgtataaaagctgaaaatcagtcacatgattata
aagcaacttctgaagaagatgtaagcataaaatctccgatttgcgaaaaacaagatgaaagtaatactgtaata
tgtcaggattctacagtaacttcagatttgttgcaagttcctgatgatttaccaaatgtgtgtgaggaaaaaaatgaa
actagcaaatatgcagaatattcctttacaagtctacctgtgccagaatcaaatctaaggactagaaatgccatta
agagattacataagcgagactcttttgataattgtagtttgggagaatcctcaaaaatagggatatcagatatttctt
cgctttcagaaaaaacttttcaaacacttgaatgccaacacaagagaagtaggagggtgaggagatctaaag
gttgtgattgctgtggggaaaaatcacaacctcaggaaaagtcactcattgggttaaagaatacagaaaataat
gacgtagagattagtgaaacaaaaaaggcagatgtgcaagcacctgtaagcccatcagaaacttctcaagct
aatccatattctgaaggacaatttttagatgaacatcatagtgtgaattttcatttgggtctcaaagaggataatgata
ctattaatgattcattaattgtttctgaaaccaaatcaaaagaaaacactatgcaagaatctcttccttctggaatagt
aaactttagagaggaaatttgtgatatggattctagtgaagcaatgtctcttgaaagccaggagtcacctaatgaa
aattttaaaactgttggcccgtgtttaggagactcgaaaaatgtttcacaggaatctttggagacaaaagaagaa
aaaccagaagaaaccccaaaaatggaactgagtctagagaatgttactgttgaaggaaatgcatgtaaagta
acagaatccaatctagagaaagcaaaaactatggaattgaatgtaggaaatgaagctagctttcatggacaag
agagaaccaaaactggtatttctgaagaagcagcaatagaagaaaataaaagaaatgatgactctgaagca
gacacagctaaactgaatgccaaagaagtagcaactgaggaatttaattcagatattagtctttctgataatacta
cacctgtaaaattgaatgctcaaactgagatttctgaacaaacagcagctggggaactagatggaggaaatga
tgtatctgatctacactcatctgaagaaacgaataccaaaatgaaaaattatgaagaaatgatgatcggcgagg
caatggctgaaactggccatgatggtgaaacagagaatgagggcataactaccaaaacctcaaagcctgatg
aagctgaaacaaacatgttgactgcagaaatggacaactttgtttgtgacacagttgaaatgagcactgaagaa
ggaatcattgacgctaataaaactgaaacaaatactgagtatagtaaatctgaagaaaattagataacaatca
aatggtaatgaaagtgatattttacaggaagatcaccatacttcacagaaagtggaggaaccatcacagtgtc
tggcatctggaacagctatctctgagctaataatagaagacaataatgcatctcctcaaaaactaagggaacttg
atccttcacttgtgtcagcaaatgacagtcctagtggcatgcagacacgctgtgtctggtctcctttggcttctccgtct
acgagcattttaaagagaggactaaaaagatcccaagaagatgaaatctcatcacctgttaataaggttcgccg
tgtctcctttgcagatccaatataccaagcaggattggcagatgacattgatagacggtgctctattgttaggtccc

FIG. 9 continued attcttccaatagttctcccataggaaaaagtgttaaaacttctcctactacacaatctaagcataataccacttcag
ccaaaggatttctgtccccaggatcacgtagccctaaatttaagagctcaaagaagtgtttaatttcagaaatggc
caaagaatccataccatgcccaacagaaagtgtttacccaccattggtgaactgtgtggcaccagttgacatcat
tttacctcagattacatcaaacatgtgggcaagaggcctgggacaactcattagagctaagaatataaaaactat
tggtgatttgagtactcttacagcatctgaaataaaaactcttcctatccgttctccaaaagtgtccaatgtaaaaaa
ggctctcagaatatatcatgagcagcaggtgaagactcgtggactagaagagattccagtttttgatatttctgaa
aaaacagtaaatggaatagaaaataaatctttgtcacctgatgaagaaagacttgtctcagatataattgatcctg
ttgctttagaaattccattatccaaaaaccttgtggcacagattagtgctcttgctcttcagctggattcagaagatctt
cataattattcaggaagccaactatttgaaatgcacgagaaactaagttgtatggcaaactctgtaataaaaaat
ctacagtcacgttggagatcaccatcccatgaaaattctatttagtattttcagagaaaattgaaggttttttaaacat
cactggatttcttgattgaggaaacaagttctgaaataatagcacaatttcaaagaagagactctttgcaaagttg
ataacatttcaaaccctgaaggacagtgacttattatccttcctttctccaaagaacagttaaaaccaaatgtgttat
ggtaagctgtaaataccgttggaataaaagataaccgttcatcttacctaaaaaattgaagacaatattttccattg
ttgatgtcacaatttcttgaagatggctctttgcagcctacgtggtagtggagatatatacaaaggacttccctagtat
cgttggaccaacaagcacaagcagatggcaggaagattagaacattggatattgattgccagttttttaagtgtca
ttcttggaaacgtgggagatttaggaaatgacattgaagaggaagaattctGTTGAAATAGTGATTCT
CAACGTGGGGTCCTTGGACAGCAAGTGATGGGGATTGGAATCCCTTTTCCA
ACGTTTTCTTTATACAACACCTGTATGACACAAGAAAGCATCCAGAAAAAAC
AAGAGCAGTCAAAACAGCCCTTTCATCTACCTTGTGGGGAACCTGGTATAAA
ACTACAGACGTCAGACAGAAAAGACAGATTCAACAAGTCAACCTCTCTGTTC
AGGCACAGATCTGGTTTTAATGATGAACTCTACAATGCTAATTCTGGAAATG
AAAAAGTACAATGGAAAGCATTAAGTTATATAACGCTGAGGAATCTTGTTAAT
TCTACTTATAGTATTTCAAATCTAGTCAAGTCACTGAAAATGTTCAAGTATAA
TCGGAAATGTGTCTTTCCGATAGCCGTTCCTGGTGAGACATCCTCTTTATAT
AAAACCTGGGCATTCAGAATCAGGACAGTGTTAACACAGAAGAAAAGAAAA
CCCAGCAGTTCCTGGAGAAAGACTAGGACACATGGCTTTTGTGAAAACAAG
ACACTAGACGATGTTCCCAGGGGTTTTCGCCATGAACCTTGCCATGGGTGA
GGAAAAGATACTATATTTTCTCCCCAATACCACCAACGAAGTAACAGATGAG
TCTTTCATGCTGTGATTTGGGATTAAGATACAAGGTGAGCCCAGAGATGAAT
TGGGCACACATTTCCTGGGGCAGGATGGGAGTTGTGGAGGGCTGCACAAC
AGCCCCACTGCAAGCCTGGGATATCCAGAGGCATCTTCCTCAGCACCCCTA
GGTGCCTGTGGGCTGTGCCTTACATTTAATAAAAACTTACAAGGCTGAAAAA
AAAAAAAAAAAAAAAAAAAAAAAAAAAAAAAAAAAAAAAAAAAAAAAAA

FIG. 10

MTARGQSPLAPLLETLEDPSASHGGQTDAYLTLTSRMTGEEGKEVITEIEKKLPRLYKV
LKTHISSQNSELSSAALQALGFCLYNPKITSELSEADALELLSKLNDTIKNSDKNVRTR
ALWVISKQTFPSEVVGKMVSSIIDSLEILFNKGETHSAVVDFEALNVIVRLIEQAPIQM
GEEAVRWAKLVIPLVVHSAQKVHLRGATALEMGMPLLLQKQQEIASITEQLMTTKLISEL
QKLFMSKNETYVLKLWPLFVKLLGRTLHRSGSFINSLLQLEELGFRSGAPMIKKIAFIAW
KSLIDNFALNPDILCSAKRLKLLMQPLSSIHVRTETLALTKLEVWWYLLMRLGPHLPANF
EQVCVPLIQSTISIDSNASPQGNSCHVATSPGLNPMTPVHKGASSPYGAPGTPRMNLS
SNLGGMATIPSIQLLGLEMLLHFLLGPEALSFAKQNKLVLSLEPLEHPLISSPSFFSKHAN
TLITAVHDSFVAVGKDAPDVVVSAIWKELISLVKSVTESGNKKEKPGSEVLTLLLKSLESI
VKSEVFPVSKTLVLMEITIKGLPQKVLGSPAYQVANMDILNGTPALFLIQLIFNNFLECGV
SDERFFLSLESLVGCVLSGPTSPLAFSDSVLNVINQNAKQLENKEHLWKMWSVIVTPL
TELINQTNEVNQGDALEHNFSAIYGALTLPVNHIFSEQRFPVXTMKTLLRTWSELYRAFA
RCAALVATAEENLCCEELSSKIMSSLEDEGFSNLLFVDRIIYIITVMVDCIDFSPYNIKYQP
KVKSPQRPSDWSKKKNEPLGKLTSLFKLIVKVIYSFHTLSFKEAHSDTLFTIGNSITXIISS
VLGHISLPSMIRKIFATLTRPLALFYENSKLDEVPKVYSCLNNKLEKLLGEIIACLQFSYTG
TYDSELLEQLSPLLCIIFLHKNKQIRKQSAQFWNATFAKVMMLVYPEELKPVLTQAKQKF
LLLLPGLETVEMMEESSGPYSDGTENSQLNVKISGMERKSNGKRDSFLAQTKNKKENM
KPAAKLKLESSSLKVKGEILLEEEKSTDFVFIPPEGKDAKERILTDHQKEVLKTKRCDIPA
MYNNLDVSQDTLFTQYSQEEPMEIPTLTRKPKEDSKMMITEEQMDSDIVIPQDVTEDCG
MAEHLEKSSLSNNECGSLDKTSPEMSNSNNDERKKALISSRKTSTECASSTENSFVVS
SSSVSNTTVAGTPPYPTSRRQTFITLEKFDGSENRPFSPSPLNNISSTVTVKNNQETVIK
TDFLPKAKQREGTFSKSDSEKIVNGTKRSSRRAGKAEQTGNKRSKPLMRSEPEKNTEE
SVEGIVVLENNPPGLLNQTECVSDNQVHLSESTMEHDNTKLKAATVENAVLLETNTVEE
KNVEINLESKENTPPVVISADQMVNEDSQVQITPNQKTLRRSSRRRSEVVESTTESQDK
ENSHQKKERRKEEEKPLQKSPLHIKDDVLPKQKLIAEQTLQENLIEKGSNLHEKTLGETS
ANAETEQNKKKADPENIKSEGDGTQDIVDKSSEKLVRGRTRYQTRRASQGLLSSIENSE
SDSSEAKEEGSRKKRSGKWKNKSNESVDIQDQEEKVVKQECIKAENQSHDYKATSEE
DVSIKSPICEKQDESNTVICQDSTVTSDLLQVPDDLPNVCEEKNETSKYAEYSFTSLPVP
ESNLRTRNAIKRLHKRDSFDNCSLGESSKIGISDISSLSEKTFQTLECQHKRSRRVRRSK
GCDCCGEKSQPQEKSLIGLKNTENNDVEISETKKADVQAPVSPSETSQANPYSEGQFL
DEHHSVNFHLGLKEDNDTINDSLIVSETKSKENTMQKTLPSGIVNLKEEICDMDSSEAM
SLESQESPNENFKTVGPCLGDSKNVSQESLETKEEKPEETPKMELSLENVTVEGNACK
VTESNLEKAKTMELNVGNEASFHGQERTKTGISEEAAIEENKRNDDSEADTAKLNAKEV
ATEEFNSDISLSDNTTPVKLNAQTEISEQTAAGELDGGNDVSDLHSSEETNTKMKNYEE
MMIGEAMAETGHDGETENEGITTKTSKPDEAETNMLTAEMDNFVCDTVEMSTEEGIIDA
NKTETNTEYSKSEEKLDNNQMVMESDILQEDHHTSQKVEEPSQCLASGTAISELIIEDN
NASPQKLRELDPSLVSANDSPSGMQTRCVWSPLASPSTSILKRGLKRSQEDEISSPVN
KVRRVSFADPIYQAGLADDIDRRCSIVRSHSSNSSPIGKSVKTSPTTQSKHNTTSAKGFL
SPGSRSPKFKSSKKCLISEMAKESIPCPTESVYPPLVNCVAPVDIILPQITSNMWARGLG
QLIRAKNIKTIGDLSTLTASEIKTLPIRSPKVSNVKKALRIYHEQQVKTRGLEEIPVFDISEK
TVNGIENKSLSPDEERLVSDIIDPVALEIPLSKNLVAQISALALQLDSEDLHNYSGSQLFE
MHEKLSCMANSVIKNLQSRWRSPSHENSI*

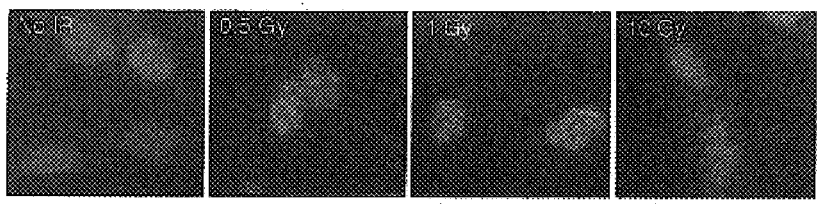
FIG. 11A
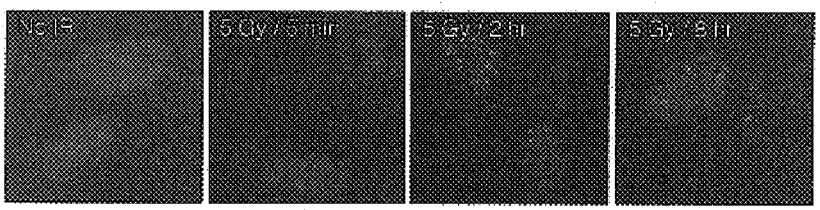
FIG. 11B
FIG. 11C
FIG. 11E
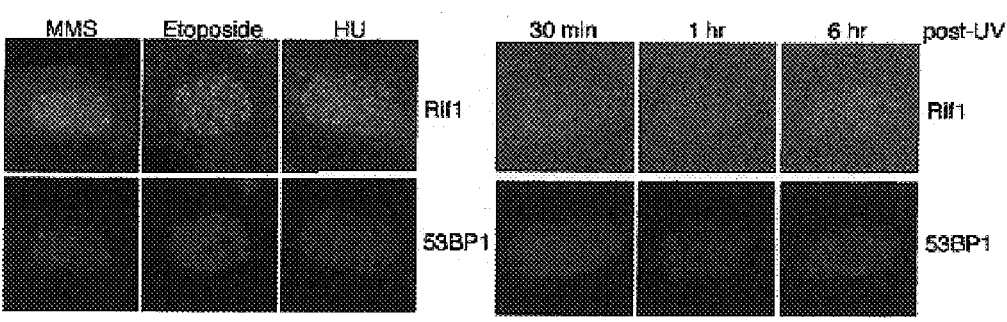
FIG. 11D
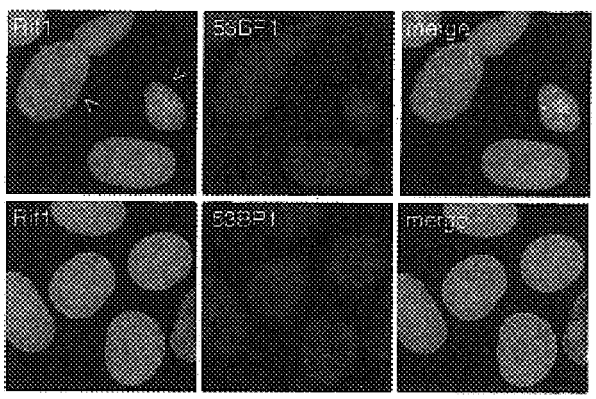
FIG. 11F

NUCLEIC ACID SEQUENCES OF HUMAN RIF1

CROSS REFERENCE TO RELATED APPLICATION

This application claims priority under 35 USC §119(e) from U.S. Provisional Application Ser. No. 60/601,405, filed Aug. 13, 2004, which application is herein specifically incorporated by reference in its entirety.

The research leading to the present invention was funded in part by NCI Grant No. CA76027. The United States government may have certain rights in the invention.

FIELD OF THE INVENTION

The present invention pertains to the fields of molecular biology, genetic testing, and diagnostic medicine. More specifically, the invention relates to human Rif1 nucleic acid sequences and amino acid sequences encoded thereby, and antibodies immunologically specific for a human Rif1 polypeptide. Methods of making and using Rif1 nucleic and amino acid sequences and Rif1 antibodies are also encompassed by the present invention.

BACKGROUND OF THE INVENTION

Several publications and patent documents are referenced in this application in order to more fully describe the state of the art to which this invention pertains. The disclosure of each of these publications and documents is incorporated by reference herein.

The ability of mammalian cells to survive chromosomal damage depends on the coordinated activity of DNA response pathways that halt cell cycle progression and facilitate DNA repair prior to DNA replication or mitosis. The Ataxia Telangiectasia Mutated (ATM) kinase plays a crucial function as a transducer of the DNA damage signal [reviewed in (Abraham. (2001) Genes Dev 15, 2177-2196; Kastan and Lim. (2000) Nat Rev Mol Cell Biol 1, 179-186; Shiloh. (2003) Nat Rev Cancer 3, 155-168; Zhou and Elledge. (2000) Nature 408, 433-439].Following the generation of double-strand breaks (DSBs) by IR or clastogens, inactive ATM kinase dimers are converted into active monomers through autophosphorylation on serine 1981 [Bakkenist and Kastan. (2003) Nature 421, 499-506]. ATM has a number of direct targets, including Nbs1, Chk2, Mdm2, 53BP1, BRCA1, Rad17, Smc1, FANCD2, and H2AX [reviewed in (D'Andrea and Grompe. (2003) Nat Rev Cancer 3, 23-34; Kastan and Lim. (2000) supra; Shiloh. (2003) supra]. The ATM- and Rad3-related kinase, ATR, responds to replication stress and UV damage as well as to DSBs [reviewed in (Abraham. (2001) supra]. ATR requires an interacting partner, ATRIP, and the loading of RPA on single-stranded DNA for its activation [Cortez et al. (2001) Science 294, 1713-1716; Zou and Elledge. (2003) Science 300, 1542-1548]. There is considerable redundancy in the ATM and ATR signaling pathways in part because most effectors can be phosphorylated by both kinases.

Many ATM targets and other proteins involved in the DNA damage response physically accumulate at or near DNA lesions [Haaf et al. (1995). Proc Natl Acad Sci USA 92, 2298-2302; reviewed in (Petrini and Stracker. (2003) supra). As was first shown by indirect immunofluorescence (IF) for the Mre11 complex [Nelms et al. (1998) Science 280, 590-592] large multimeric complexes, termed ionizing radiation induced foci (IRIF) are formed at sites of DNA damage. IRIFs contain numerous additional factors, including ATM, ATR, ATRIP, β-H2AX, Rad17, Chk1, 53BP1, and BRCA1.

A hallmark of AT cells is their diminished ability to survive ionizing radiation (IR) or other genotoxic treatments that create double-strand breaks [Taylor et al. (1975) Nature 258, 427-429; reviewed in (Shiloh, 2003, supra]. The ATM-dependent DNA damage response can block progression through the cell cycle before, during, and after DNA replication. DNA damage-induced cell cycle arrest in late G1/early S phase involves ATM-dependent activation of p53, a process that is mediated by Chk2 and Mdm2 [Hirao et al. (2000) Science 287, 1824-1827; Kastan et al. (1992) Cell 71, 587-597; Maya et al. (2001) Genes Dev 15, 1067-1077]; reviewed in Abraham et al. (2001) supra]. The intra-S phase checkpoint involves ATM-mediated phosphorylation of Nbs1, Smc1, and BRCA1 [Gatei et al. (2000) Nat Genet 25, 115-119; Kim et al. (2002) Genes Dev 16, 560-570; Lim et al. (2000) Nature 404, 613-617; Wu et al. (2000) Nature 405, 477-482; Xu et al. (2001) Mol Cell Biol 21, 3445-3450; Xu et al. (2002b) Cancer Res 62, 4588-4591; Yazdi et al. (2002) Genes Dev 16, 571-582; Zhao et al. (2000) Nature 405, 473-477]. ATM controls a second parallel intra-S phase pathway that is dependent on Chk2-mediated phosphorylation of Cdc25A, resulting in degradation of Cdc25A and reduced Cdk2 activity [Falck et al. (2001) Nature 410, 842-847; Falck et al. (2002) Nat Genet 30, 290-294]. When the intra-S phase checkpoint is compromised, radioresistant DNA synthesis (RDS) takes place, a second hallmark of AT cells. ATM is also important for the G2/M arrest after IR, a pathway that involves phosphorylation of BRCA1 and inhibition of Cdc25C by Chk2 ATM [Matsuoka et al. (1998) Science 282, 1893-1897; Xu et al. (2001) Mol Cell Biol 21, 3445-3450].

The ATM gene is an example of a complex polyexonic eukaryotic gene that codes for a large protein product, defects in which appear as autosomal recessive mutations. Ataxia telangiectasia (AT), which presents in patients that possess mutations in both alleles of the ATM gene, is an autosomal recessive, multi-system disorder that leads to progressive neuromuscular and vascular degeneration. As indicated herein above, chromosomal breakage and rearrangement are characteristic features of AT cells, which are abnormally sensitive to ionizing radiation. This hypersensitivity is evident in homozygous recessive AT patients and heterozygous carriers, both of which genotypes/phenotypes are predisposed to the development of cancer.

Because of the severity of the disease associated with mutations in the ATM gene, accurate and early detection of an ATM mutation in a patient is critical for the care of the affected individual. Moreover, patients or families frequently request confirmation of a suspected diagnosis of AT. Definitive detection of an ATM mutation in a patient merits additional screening of the patient's family members to identify other individuals possessing the mutation in either homozygous or heterozygous form. Since carriers of ATM mutations (i.e., heterozygotes with one normal gene) may also display an increased risk for cancer, particularly breast cancer, testing for such mutations is imperative because early detection is a critical predictive factor for improved prognosis in cancer patients. Early detection also enables the patient and healthcare providers thereof to take precautionary measures to minimize the exposure of the patient to ionizing radiation.

Improved methods for detecting polymorphisms in the ATM gene are, therefore, needed. Available techniques include restriction endonuclease fingerprinting (REF), the single-stranded conformation polymorphism (SSCP) technique, and the protein truncation test (PTT). Each of these methods, however, suffers from a variety of drawbacks. In general, the methodology used to screen for mutations biases the types of mutations that can be found. The PTT, for example, cannot detect mutations occurring in non-coding regions such as control elements. Thus, a need for improved methods for detecting mutations and polymorphisms in complex polyexonic eukaryotic structural genes such as ATM exists.

SUMMARY OF INVENTION

In one aspect, the present invention is directed to a method for diagnosing ataxia telangiectasia (AT) in a mammal, wherein said method comprises detecting ataxia telangiectasia mutated (ATM) activity in a mammal, said method comprising: (a) isolating at least one cell from said mammal; (b) treating said at least one cell, wherein said treating is capable of inducing foci comprising Rif1 (i.e., sites of DNA damaged) in treated cells having normal levels of ATM kinase activity; and (c) detecting Rif1 in treated cells, wherein detection of foci comprising Rif1 is indicative of normal levels of ATM kinase activity in said treated cells and wherein an absence of detectable foci comprising Rif1 is indicative of reduced levels of ATM kinase activity in said treated cells and is a positive diagnostic indicator of ataxia telangiectasia in said mammal. Indeed, the method of the present invention may be used to identify people with defects in any part of a signaling pathway upstream of Rif1, including 53BP1 and unknown genes.

The mammal utilized can be any mammal, including, for example, a mouse, cat, dog, or pig. The ability of human Rif1 antibodies to cross-react with Rif1 orthologs/homologs of these species is predictive of the utility of the present method for mammals other than humans.

In a particular embodiment, the mammal is a primate, such as a monkey or a human. The present method is used to particular advantage with a human subject that is suspected of being homozygous for an ataxia telangiectasia mutation. A skilled artisan would also appreciate that the present method may be used to identify subjects that are compound homozygous for two different ATM mutations.

Various methods may be used to induce DNA damage in the methods of the invention. Such methods include, but are not limited to, those wherein the treating comprises irradiating said at least one cell or contacting said at least one cell with a radiomimetic drug. In an embodiment of the invention, the irradiating level of the method is between 0.1 and 50 Gray (Gy). In a particular embodiment, the irradiating level is between 0.5 and 10 Gy. Exemplary radiomimetic drugs include, but are not limited to, etoposide, neocarzinostatin, campothecin, or bleomycin. A skilled artisan would be aware of the dose range of a particular radiomimetic drug that induces the same or a similar amount of DNA damage as compared to that induced by a dose range of 0.1-50 Gray gamma irradiation.

In one embodiment, the at least one cell of the methods of the invention is a cell isolated from a bodily fluid sample, wherein the bodily fluid sample includes, but is not limited to, blood or a blood isolate, lymphatic fluid, pleural effusion, or ascites. In another embodiment, the at least one cell is a cell isolated from a tissue sample, such as, for example, a skin sample, a hair root sample, or a tumor sample.

In another aspect of the invention, a method for determining ATM status in a tumor specimen isolated from a mammal is presented, wherein the method comprises detecting ataxia telangiectasia mutated (ATM) activity in the tumor specimen, the method comprising: (a) isolating at least a portion of said tumor specimen from said mammal; (b) irradiating said at least a portion of said tumor specimen, wherein said irradiating is capable of inducing foci comprising Rif1 (i.e., sites of DNA damage) in irradiated cells having normal levels of ATM kinase activity; and (c) detecting Rif1 in irradiated cells of said at least a portion of a tumor specimen, wherein detection of foci comprising Rif1 is indicative of normal levels of ATM kinase activity in said irradiated cells and wherein an absence of detectable foci comprising Rif1 is indicative of reduced levels of ATM kinase activity in said irradiated cells and reveals ATM status in said tumor specimen. The at least one portion of a tumor specimen isolated from a mammal may be further processed prior to the irradiating step to render the specimen a cell suspension, for example, so as to facilitate more uniform exposure of the treated cells to the irradiation. Such procedures are known in the art and described herein.

In one aspect of the method, absence of detectable foci comprising Rif1 is indicative of reduced levels of ATM kinase activity in said irradiated cells of the mammal's tumor specimen and detection of reduced levels of ATM kinase activity identifies a mammal treatable by agents capable of modulating ATM activity.

The invention also describes a method for screening to identify a modulator of ATM activity, said method comprising the steps of: (a) dividing a population of cells into at least two subpopulations of cells; (b) contacting a first subpopulation of cells with an agent; (c) contacting a second subpopulation of cells with a control substance; (d) treating the first and second subpopulations of cells, wherein said treating is capable of inducing foci comprising Rif1 in treated cells having normal ATM kinase activity; and (e) detecting Rif1 in the first and second subpopulations of treated cells, wherein a change in foci number comprising Rif1 in the first subpopulation of treated cells relative to that detected in the second subpopulation of treated cells identifies an agent capable of modulating ATM activity.

In an aspect of the invention, treating comprises irradiating said population of cells or contacting said population with a radiomimetic drug. In one embodiment, the irradiating level of the method is between 0.1 and 50 Gray (Gy). In a particular embodiment, the irradiating level is between 0.5 and 10 Gy. Exemplary radiomimetic drugs include etoposide, neocarzinostatin, campothecin, or bleomycin. A dose range of a particular radiomimetic drug that induces the same or a similar amount of DNA damage as compared to that induced by a dose range of 0.1-50 Gray gamma irradiation may readily be determined by an ordinarily skilled practitioner.

In one aspect, an agent identified as capable of modulating ATM activity decreases ATM kinase activity. In another aspect, an agent capable of modulating ATM activity increases ATM activity. In a particular embodiment, the agent is present until the time at which the subpopulations are processed (e.g., fixed).

The invention is also directed to a method for screening to identify a modulator of Rif1 activity, said method comprising the steps of: (a) dividing a population of cells into at least two subpopulations of cells; (b) contacting a first subpopulation of said cells with an agent; (c) contacting a second subpopulation of said cells with a control substance; (d) treating the first and second subpopulations of cells, wherein said treating is capable of inducing foci comprising Rif1 in treated cells having normal ATM kinase activity; and (e) detecting Rif1 in the first and second subpopulations of cells, wherein a change in foci number comprising Rif1 in the first subpopulation of treated cells relative to that detected in the second subpopulation of treated cells identifies an agent capable of modulating Rif1 activity.

The above screening method calls for treating which comprises irradiating said population of cells or contacting said population with a radiomimetic drug. In one embodiment, the irradiating level of the method is between 0.1 and 50 Gray (Gy). In a particular embodiment, the irradiating level is between 0.5 and 10 Gy. Exemplary radiomimetic drugs include, but are not limited to, etoposide, neocarzinostatin, campothecin, or bleomycin. As described herein, an appropriate dose range of a particular radiomimetic drug capable of inducing the same or a similar amount of DNA damage as compared to that induced by a dose range of 0.1-50 Gray gamma irradiation is a matter of routine practice for a skilled person.

An agent identified using the above screening method, which is capable of modulating hRif1 activity may either decrease or increase hRif1 activity. Exemplary agents capable of decreasing and/or inhibiting hRif1 activity include, but are not limited to: Rif1 small inhibitory RNAs (siRNAs) described herein below. An agent identified as a hRif1 modulator may also be capable of modulating ATM activity and may, therefore, either decrease or increase ATM kinase activity. In a particular embodiment, the agent is present until the time at which the subpopulations are processed (e.g., fixed).

Also included in the present invention is a method for increasing radiation sensitivity of cancer cells, said method comprising introducing a modulating agent identified in the screening methods of the invention into a population of cancer cells, wherein said introducing decreases ATM kinase activity and effectuates an increase in radiation sensitivity of said population of cancer cells. Such agents may be introduced into a population of transformed cells or cancer cells in vitro or in vivo.

In another aspect, a method is presented for increasing radiation sensitivity of cancer cells, said method comprising introducing a modulating agent identified in the screening methods of the invention into a population of cancer cells, wherein said introducing decreases Rif1 activity and effectuates an increase in radiation sensitivity of said population of cancer cells. Such agents may be introduced into a population of cancer cells in vitro or in vivo.

The present invention also includes a method of treating a patient with a cancer, said method comprising administering to said patient at least one modulating agent (ATM modulatory agent or hRif1 modulatory agent) identified in the screening methods of the invention, wherein said at least one agent increases sensitivity of cancer cells in said patient to radiation. For some applications, the at least one modulatory agent is delivered directly into a tumor in said patient. Alternatively, or in addition, the at least one modulatory agent is delivered systemically to a patient with a cancer.

The invention is also directed to an isolated nucleic acid sequence encoding a polypeptide comprising SEQ ID NO: 2 or having sequence and/or structural homology to SEQ ID NO: 2, or a functional fragment thereof, wherein said polypeptide exhibits an activity of hRif1, for example, is capable of forming foci at sites of DNA damage in cells treated to induce DNA damage, wherein said cells have normal ATM kinase activity. In one embodiment, a polypeptide having sequence and/or structural homology to SEQ ID NO: 2 or a functional fragment thereof is a hRif1 homolog or ortholog that exhibits a hRif1 activity. Also included are expression vectors comprising an isolated nucleic acid sequence which encodes an amino acid sequence of the invention (e.g., SEQ ID NO: 2), wherein expression of the nucleic acid sequence is controlled by regulatory sequences in the expression vector. Cells comprising such expression vectors are also encompassed. In yet another aspect, a transgenic animal comprising an isolated nucleic acid sequence encoding a polypeptide comprising SEQ ID NO: 2 or a hRif1 homolog or ortholog is presented, wherein the polypeptide is a hRif1 polypeptide or functional fragment thereof, capable of exhibiting a hRif1 activity, and the nucleic acid sequence is expressed in at least one cell of the transgenic animal.

In another aspect of the invention, an isolated amino acid sequence comprising a polypeptide of SEQ ID NO: 2, or having sequence and/or structural homology to either SEQ ID NO: 2, or a functional fragment thereof, wherein said polypeptide is capable of exhibiting a hRif1 activity, is presented. As described herein, hRif1 activities include the ability to form foci at sites of DNA damage in cells treated to induce DNA damage, wherein said cells have normal ATM kinase activity. Also included are expression vectors encoding an amino acid sequence of the invention (e.g., SEQ ID NO: 2), wherein expression of the amino acid sequence is controlled by regulatory sequences in the expression vector, cells comprising such expression vectors, and transgenic animals comprising an amino acid sequence of the invention, wherein the amino acid sequence is expressed in at least one cell in the transgenic animal.

In another aspect of the invention, an isolated nucleic acid sequence comprising SEQ ID NO: 1 is provided, wherein the nucleic acid sequence encodes hRif1 or functional fragment thereof capable of exhibiting an activity attributable to hRif1 as described herein. Also described is an expression vector comprising a nucleic acid sequence of SEQ ID NO: 1, wherein the nucleic acid sequence encodes hRif1 or functional fragment thereof capable of exhibiting a Rif1 activity, and SEQ ID NO: 1 is operably linked to a regulatory sequence. Moreover, a cell comprising such an expression vector is also within the scope of the invention. In another aspect, a transgenic animal comprising a nucleic acid sequence comprising SEQ ID NO: 1, wherein the nucleic acid sequence encodes hRif1 or functional fragment thereof capable of exhibiting a hRif1 activity, and wherein the nucleic acid sequence is expressed in at least one cell of the transgenic animal is presented.

The present invention also encompasses an antibody immunologically specific for an amino acid sequence comprising SEQ ID NO: 2. Such antibodies can be polyclonal or monoclonal antibodies and functional fragments thereof.

The present invention also includes a kit comprising an isolated nucleic acid sequence comprising SEQ ID NO: 1, wherein the nucleic acid sequence encodes a hRif1 polypeptide or functional fragment thereof; an isolated nucleic acid sequence encoding an amino acid sequence comprising SEQ ID NO: 2 or a functional fragment thereof; an isolated amino acid sequence comprising SEQ ID NO: 2, wherein the amino acid sequence is a hRif1 polypeptide or functional fragment thereof; a hRif1 activity compatible buffer; at least one antibody immunologically specific for hRif1; and instructional materials.

Also described is a composition comprising at least one hRif1 polypeptide or functional fragment thereof, hRif1 encoding nucleic acid sequence, at least one antibody immunologically specific for hRif1, and/or hRif1 and/or ATM modulatory agent identified using the methods of the invention and a pharmaceutically acceptable buffer.

Other features and advantages of the invention will be apparent from the following description of the preferred embodiments thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-B show (A) schematic of human Rif1 indicating the approximate position of the regions conserved in vertebrate Rif1 proteins (CRI-III), a predicted bipartite nuclear localization signal (NLS), and a serine (Ser) rich region. The positions of antigens used for generating antibodies are also indicated (underlying boxes); and (B) immunoblots of HeLa cell extract probed with the indicated antibodies or a pre-immune serum (1060 PI).

FIGS. 7A-B show cartoons depicting the role of Rif1 (A) in the DNA damage response and (B) at telomeres.

FIGS. 8A-B show alignments of human Rif1 open reading frames with Rif1 from other species, specifically (A) shows a schematic of human Rif1 indicating the approximate position of conserved regions CRI-III and illustrates ClustalX alignment of human, mouse, and fugu Rif1 orthologs: red indicates amino acids conserved in all three genes, blue indicates amino acids conserved in two of the three genes, and black indicates non-conserved amino acids. Amino acid sequences and sequence identifiers are as follows: human Rif1: SEQ ID NO: 2; mouse Rif1: SEQ ID NO: 11; fugu Rif1: SEQ ID NO: 12; and S. cerevisiae Rif1; SEQ ID NO: 13; and (B) illustrates ClustalX alignment of the indicated regions from human and S. cerevisiae Rif1. Amino acid sequences and identifiers are as follows: human Rif1 amino acid sequences 1-1081 (CRI-II domains) and amino acid sequences 2144-2365 (CRIII domain) of SEQ ID NO: 2; and S. cerevisiae Rif1 amino acid sequences 172-1219 and 1345-1579 of SEQ ID NO: 13.

FIG. 9 shows a nucleic acid sequence encoding human Rif1 (SEQ ID NO: 1). The start codon at position 131 and the stop codon at position 7547 are underlined.

FIG. 10 shows an amino acid sequence of human Rif1 (SEQ ID NO: 2).

FIGS. 11A-F show photomicrographs depicting immunofluorescence staining.

DETAILED DESCRIPTION OF THE INVENTION

Figure 2A:
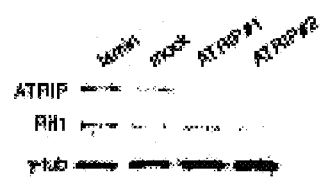
FIGS. 2A-B show (A) immunoblotting analysis of the effect of ATRIP siRNAs on HeLa1.2.11 cells transfected twice with the indicated siRNAs and analyzed by immunoblotting for expression of the indicated proteins (Rif1 was detected with mouse serum 1060) and (B) Immunoblotting analysis of the effects of ATRIP siRNAs on Rad17 S345 and Chk1 S345 phosphorylation in HeLa1.2.11 cells treated as in (A) and exposed to 25 J/m² UV 72 hr after siRNA transfection. Cells were collected 1 hr post-UV and immunoblotting for the indicated protein.

In order to more clearly set forth the parameters of the present invention, the following definitions are used:

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

The term "complementary" refers to two DNA strands that exhibit substantial normal base pairing characteristics. Complementary DNA may, however, contain one or more mismatches. The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 60%, but often, more than 85%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The terms "percent similarity", "percent identity" and "percent homology" when referring to a particular sequence are used as set forth in the University of Wisconsin GCG software program and are known in the art.

The present invention also includes active portions, fragments, derivatives and functional or non-functional mimetics of a human Rif1 polypeptide or protein of the invention. An "active portion" of a human Rif1 polypeptide means a peptide that is less than the full length human Rif1 polypeptide, but which retains measurable Rif1 biological activity.

A "fragment" or "portion" of a human Rif1 polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. A "derivative" of the human Rif1 polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of the original human Rif1 polypeptide.

Different "variants" of the human Rif1 polypeptide exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acid residues are substituted with conservative or non-conservative amino acids, (b) variants in which one or more amino acids are added to the human Rif1 polypeptide, (c) variants in which one or more amino acids include a substituent group, and (d) variants in which the human Rif1 polypeptide is fused with another peptide or polypeptide such as a fusion partner, a protein tag or other chemical moiety, that may confer useful properties to the human Rif1 polypeptide, such as, for example, an epitope for an antibody, a polyhistidine sequence, a biotin moiety and the like. Other human Rif1 polypeptides of the invention include variants in which amino acid residues from one species are substituted for the corresponding residue in another species, either at conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to a person having ordinary skill in the art.

To the extent such allelic variations, analogues, fragments, derivatives, mutants, and modifications, including alternative nucleic acid processing forms and alternative post-translational modification forms result in derivatives of a human Rif1 polypeptide that retain any of the biological properties of the human Rif1 polypeptide, they are included within the scope of this invention.

The term "ortholog" as used herein refers to polypeptides encoded by nucleic acid sequences of a different species whose polypeptide product has greater than 60% identity to a human Rif1 encoding sequence and/or whose gene products have similar three dimensional structure and/or biochemical activities of human Rif1. The use of such orthologs in the methods of the invention is contemplated herein.

The term "homolog" as used herein refers to polypeptides encoded by nucleic acid sequences of the same species whose polypeptide product has greater than 60% identity to a human Rif1 encoding sequence and/or whose gene products have similar three dimensional structure and biochemical activities of human Rif1. The use of such homologs in the methods of the invention is contemplated herein.

The term "functional" as used herein implies that the nucleic or amino acid sequence is functional for the recited assay or purpose.

The term "functional fragment" as used herein implies that the nucleic or amino acid sequence is a portion or subdomain of a full length polypeptide and is functional for the recited assay or purpose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence and which are placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers may be labeled fluorescently with 6-carboxyfluorescein (6-FAM). Alternatively primers may be labeled with 4, 7, 2',7'-Tetrachloro-6-carboxyfluorescein (TET). Other alternative DNA labeling methods are known in the art and are contemplated to be within the scope of the invention.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like). "Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

The compositions containing the molecules or compounds of the invention can be administered for diagnostic and/or therapeutic treatments. In therapeutic applications, compositions are administered to a patient already suffering from a hyperproliferative disorder (such as, e.g., cancer) in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

As used herein, the term "cancer" refers to an abnormal growth of tissue resulting from uncontrolled progressive multiplication of cells. Examples of cancers that can be treated according to a method of the present invention include, without limitation, sarcomas, blastomas, and carcinomas such as: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastric cancer, pancreatic cancer, breast cancer, meningeal carcinomatosis (which is most commonly associated with disseminated breast or lung cancer), ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumor, cervical cancer, testicular cancer, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Examples of hematologic malignancies that can be treated according to a method of the present invention include: acute myeloid leukemia (AML), chronic myeloid leukemia (CML), acute lymphocytic leukemia (ALL), chronic lymphocytic leukemia (CLL), multiple myeloma, non-Hodgkin's lymphoma (NHL), Hodgkin's disease and lymphoma (HD), pro-lymphocytic leukemia (PLL), and myelodysplastic syndrome (MDS).

An "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in vitro and in various cellular or animal systems.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunloglobulin molecule such as those portions known in the art as Fab, Fab', F(ab')2 and F(v).

As used herein, an "agent", "candidate compound", or "test compound" may be used to refer to, for example, nucleic acids (e.g., DNA and RNA), carbohydrates, lipids, proteins, peptides, peptidomimetics, small molecules and other drugs.

The term "control substance", "control agent", or "control compound" as used herein refers a molecule that is inert or has no activity relating to an ability to modulate a biological activity. With respect to the present invention, such control substances are inert with respect to an ability to modulate a hRif1 activity, an ATM kinase activity, and/or a signaling pathway that contributes to an activity of either of hRif1 or ATM kinase. Exemplary controls include, but are not limited to, solutions comprising physiological salt concentrations.

The term "hRif1 modulatory agent" as used herein refers to an agent that is capable of modulating (e.g., increasing or decreasing) an activity attributable to hRif1. The term "ATM modulatory agent" as used herein refers to an agent that is capable of modulating (e.g., increasing or decreasing) an ATM kinase activity. Methods for screening/identifying such agents are presented herein below. It is to be understood that agents identified in screening assays as hRif1 modulators may also be found to exhibit ATM modulator properties. The inverse is also a possibility in that an agent identified in a screening assay as an ATM modulator may also exhibit properties of a hRif1 modulator. Upon reading the specification, a skilled artisan would anticipate that the respective signal transduction pathways of hRif1 and ATM kinase clearly intersect, and thus, modulators of the activity of one of these molecules may potentially act as a modulator of the other molecule.

As used herein, the term "normal ATM kinase activity" refers to levels of ATM kinase activity that are observed in homozygous ATM+/ATM+ cells and heterozygous ATM+/ATM– cells. The terms "wild type ATM kinase activity" or "wild type levels of ATM kinase activity" may also be used to refer to "normal ATM kinase activity".

As used herein, the term "foci comprising hRif1" refers to complexes comprising hRif1 which form at sites of DNA damage caused by treating a cell with various conditions/agents that induce DNA damage. As described herein, foci comprising hRif1 have been found to form in the presence of wildtype ATM kinase activity levels. In the absence of wild-type ATM kinase activity levels, hRif1 foci do not form at sites of DNA damage.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

All publications mentioned herein are incorporated herein by reference to disclose and described the methods and/or materials in connection with which the publications are cited.

Aspects of the Invention

Before the present discovery and methods of use thereof are described, it is to be understood that this invention is not limited to particular assay methods, or test compounds and experimental conditions described, as such methods and compounds may vary. It is also to be understood that the terminology used herein is for the purpose of describing particular embodiments only, and is not intended to be limiting, since the scope of the present invention will be limited only the appended claims.

The present inventors have discovered that human Rif1 (hRif1), the human ortholog of yeast Rif1 (Rap1 interacting factor 1), is a novel component of the ATM pathway. Rif1 was identified in budding yeast (*Saccharomyces cerevisiae; S. cerevisiae*) as one of two Rap1 binding partners required for the regulation of telomere length [Hardy et al. (1992) Genes Dev 6, 801-814] and a similar function has been ascribed to Rif1 from *Schizosaccharomyces pombe [S. pombe*; Kanoh and Ishikawa. (2001) Curr Biol 11, 1624-1630]. The maintenance of yeast telomeres is controlled by a negative feedback loop that involves binding of the telomere length regulator Rap1 to the telomeric repeat tract [reviewed in Smogorzewska et al. (2000) Mol Cell Biol 20, 1659-1668]. Telomere-bound Rap1 recruits Rif1 and Rif2 which both limit extension of the telomeric tract by telomerase [Hardy et al. (1992), supra; Marcand et al. (1997) Science 275, 986-990; Wotton and Shore. (1997) Genes Dev 11, 748-760]. Recent data indicate that Rif1 and Rif2 promote a telomere state that blocks telomerase access [Teixeira et al. (2004) Cell, 117, 323-335]. Rif1 is also required for gene-silencing at subtelomeric loci in *S. cerevisiae* [Hardy et al. (1992), supra] and *S. pombe* Rif1 affects spore viability [Kanoh and Ishikawa. (2001) Curr Biol 11, 1624-1630].

The present inventors have identified a hRif1 gene by database analyses, and have determined that this is likely to be the only Rif1 ortholog in the human genome. The sequence similarity of hRif1 to *S. cerevisiae* Rif1 (scRif1) and *S. pombe* Rif1 (spRif1) is modest (10-15% sequence identity) but extends throughout the reading frame. Significantly, as described for the first time herein, hRif1 functions as a DNA damage response factor required for cell survival after radiation damage and proper execution of the intra-S phase checkpoint. These findings underscore the close relationship between the DNA damage response and telomere function and reveal a substantial evolutionary change in the telomeric complex. This discovery also demonstrates that human Rif1 displays a functional activity distinct from those previously characterized for yeast Rif1 homologs.

Accordingly, the invention is directed to an isolated nucleic acid sequence that encodes a polypeptide comprising SEQ ID NO: 2 or a functional fragment thereof. Also encompassed by the invention are expression vectors comprising an isolated nucleic acid sequence which encodes a polypeptide comprising SEQ ID NO: 2 or a functional fragment thereof. Cells comprising these expression vectors are also envisioned, as are transgenic animals comprising an isolated nucleic acid sequence of the invention, wherein a nucleic acid sequence is expressed in at least one cell of the transgenic animal.

In another aspect of the invention, an isolated amino acid sequence comprising a polypeptide of SEQ ID NO: 2 or a functional fragment thereof is presented. With regard to SEQ ID NO: 2, amino acid position 699 has been determined to be an alanine (Ala) and amino acid position 836 has been determined to be an glycine (Gly). Also included are expression vectors encoding an amino acid sequence of the invention, wherein expression of the amino acid sequence is controlled by regulatory sequences in the expression vector, cells comprising such expression vectors, and transgenic animals comprising an amino acid sequence of the invention, wherein the amino acid sequence is expressed in at least one cell in the transgenic animal.

In another aspect of the invention, an isolated nucleic acid sequence comprising SEQ ID NO: 1, wherein the nucleic acid sequence encodes human Rif1 or a functional fragment thereof, is presented. An expression vector comprising a nucleic acid sequence of SEQ ID NO: 1, wherein the nucleic acid sequence encodes human Rif1 or a functional fragment thereof, and SEQ ID NO: 1 is operably linked to a regulatory sequence is also described. Moreover, a cell comprising such an expression vector comprising a nucleic acid sequence of SEQ ID NO: 1 is presented. In another aspect, a transgenic animal comprising a nucleic acid sequence comprising SEQ ID NO: 1, wherein the nucleic acid sequence encodes human Rif1 or a functional fragment thereof, and wherein the nucleic acid sequence is expressed in at least one cell of the transgenic animal, is presented.

The present invention also describes antibodies that are immunologically specific for human Rif1. The hRif1 antibodies described herein are the first antibodies specific for a human Rif1 polypeptide to be characterized. As described in detail herein below, polyclonal antibodies immunologically specific for hRif1 have been raised in rabbits and mice in response to two different Rif1 peptides and a protein fragment fused to GST (FIG. 1A). Polyclonal rabbit and mouse antisera raised against each one of these immunogens reacts with the same large (>250 kDa) polypeptide in immunoblots of human cell lines (FIG. 1B). Notably, cells treated with Rif1 small interfering RNAs (siRNAs) showed diminished abundance of this >250 kDa protein, thereby establishing the specificity of the sera generated.

As described by Adams and McLaren [2004, Developmental Dynamics 229:733-744], a mouse ortholog of the yeast Rif1 family of telomere-associated proteins has been isolated. As detailed therein, polyclonal antibodies were generated that are immunologically specific for mouse Rif1 (mRif1).

The region of the mRif1 open reading frame (bases 28-861) against which these antibodies were generated is distinct from the antigenic regions of hRif1 that were selected as immunogens in the methods of the present invention. Indeed, there is no overlap in the antigenic regions used for generating the polyclonal antibodies specific for either mRif1 or hRif1. Moreover, these proteins are only about 65% identical.

As described herein, human Rif1 is required for the pathway whereby the ATM kinase ensures cellular survival after DNA damage. This function is novel and unexpected since the budding and fission yeast Rif1 genes are not known to be involved in the DNA damage response. The strict dependence of human Rif1 on ATM is unusual among ATM substrates, which generally also respond to regulatory input from ATR. Because of this unique regulation, IR-induced hRif1 foci are an excellent indicator for ATM kinase activity. A cell-based assay for ATM activity based on hRif1 foci may, therefore, be used advantageously to identify individuals with alterations in this pathway and reveal the ATM status of tumor samples, thereby improving cancer diagnosis and treatment. Furthermore, the Rif1 assay may be used to identify ATM inhibitors, which have potential application in radiation oncology.

Ataxia Telangiectasia

Ataxia telangiectasia (AT) is an autosomal recessive, multi-system disorder characterized by progressive neuromuscular and vascular degeneration, which is transmitted at an estimated frequency of one per 40,000 live births. AT patients exhibit cerebellar ataxia that gradually develops into general motor dysfunction, oculocutaneous telangiectases (dilation of blood vessels), and various immunological defects. These defects include severe impairment of thymic development, wherein the thymus is either absent or vestigial, and reduced levels of serum IgA, IgE or IgG2, peripheral lymphopenia, and reduced responses to viral antigens and allogeneic cells, that cause many patients to suffer from recurrent sinopulmonary infections. Chromosomal breakage and rearrangement are common features of AT cells, which are abnormally sensitive to ionizing radiation. Moreover, both homozygous recessive AT patients and heterozygous carriers are predisposed to malignancy.

The onset of AT generally occurs by age three, the first symptom of which is usually truncal ataxia [Woods and Taylor. (1992) Quart. J. Med. 82:169-179]. Truncal ataxia, which precedes appendicular ataxia, is characterized by deep tendon reflexes which become diminished or absent by age eight. At patients eventually lose large-fiber sensation. Moreover, by their twenties and early thirties, many AT patients develop progressive spinal muscular atrophy which particularly affects the hands and feet. The most common cause of death in AT patients, typically during the second or third decade of life, is a sinopulmonary infection, with or without malignancy.

Ataxia is reviewed elsewhere, inter alia, in The Merck Manual of Diagnosis and Therapy, 16th Ed. (1992) Merck Research Laboratories, Rahway, N.J. See also Sedgwick and Boder (1991) in Handbook of Clinical Neurology: Hereditary Neuropathies and Spinocellular Atrophies Vol. 16(60) (P. J. Ninken et al., edu.), pp. 347-423, Elsevier Science, Amsterdam.

AT Heterozygotes

As alluded to herein above, AT heterozygotes exhibit a pronounced predisposition for developing a variety of malignancies, with a 3- to 4-fold increased risk for all cancers between the ages of 20 and 80, and a 5-fold increased risk of breast cancer in women. These statistics underscore the ramifications of the disease as a public health problem and accentuate the need to develop improved assays for the identification of heterozygous individuals. Cultured cells from AT heterozygotes indeed show an intermediate degree of X-ray sensitivity, but the difference from normal cells is not always large enough to warrant using this criterion as a laboratory assay for carrier detection. The main reason for the lack of reliability of this assay is the varying degrees of overlap between AT heterozygotes and non-heterozygotes with respect to radiosensitivity. Cytogenetic assays for carriers suffer from the same problems encountered with prenatal diagnosis in that they are labor intensive and frequently inconsistent.

Methods of AT Diagnosis

Diagnosis of ataxia telangiectasia (AT) is definitive when a patient presents with early-onset ataxia with telangiectasias. Before the appearance of telangiectases, clinical diagnosis is problematic because cerebellar ataxia and oculomotor apraxia are also typical of X-linked Pelizaeus-Merzbacher disease and Joubert's syndrome. Elevated levels of alpha-fetoprotein and carcinoembryonic antigen have proven to be the most useful clinical markers (Gatti et al. (1991) Medicine 70:99-117). Dysgammaglobulinemia, decreased cellular immune responses, and peripheral lymphopenia are also indicative of AT, but they are not necessarily evident in all AT patients.

Many other assays have been developed to diagnose AT and/or determine status of the ATM gene in patients. A rapid diagnostic method based on the hypersensitivity of AT lymphocytes to gamma irradiation has, for example, been developed by Henderson et al. (1985, Lancet 11:1242). Such studies have been applied to fibroblasts and chorionic villus samples. Shiloh et al. (1989, Hum. Genet. 84:15-18) evaluated the extent of X-ray damage to chromatids in the G2 phase of AT heterozygous cells to provide an assay to test for heterozygosity of the ATM gene. The reliability of this approach has, however, been challenged on the basis that radiosensitivity of AT cells may be caused by their failure to delay DNA synthesis after radiation damage [Painter and Young (1980) Proc. Natl. Acad. Sci. 77:7315-7317). The exfoliated cell micronucleus test has also been developed to evaluate cells derived from either the oral cavity (collected by swabbing the mucosa) or the urinary bladder (obtained by centrifugation of fresh urine specimens). Micronuclei are membrane-bound, Feulgen-positive, acentric fragments that are produced by fragmentation of chromosomes during division of epithelial cells. Both AT homozygotes and heterozygotes can be identified by this method [Rosin and Ochs (1986) Hum. Genet. 74:335-340; (1989) Hum. Genet. 83:133-138].

Rif1 Localization: An Indicator of ATM Status

The method of the present invention, therefore, addresses the profound need for a reliable assay for the accurate screening of subjects suspected of having mutated alleles for ATM kinase. The method is particularly directed to the analysis of cells isolated from subjects suspected to be homozygous for mutated alleles of the ATM kinase. Such patients are particularly vulnerable to the effects of ionizing radiation and similar insults that lead to DNA damage, thus early identification of a mutated ATM kinase genotype would be an invaluable piece of information for the caretakers and physicians attending the patient. A definitive diagnosis of ATM early in life, preferably before the onset of disease symptoms, would suggest which therapeutic regimens would be effective and which would be contraindicated in view of the subject's ATM genotype.

Preparation of hRif1-Encoding Nucleic Acid Molecules and hRif1 Polypeptides

Nucleic Acid Molecules: Nucleic acid molecules encoding hRif1 polypeptide may be prepared by two general methods: (1) Synthesis from appropriate nucleotide triphosphates; or (2) Isolation from biological sources. Both methods utilize protocols well known in the art.

The availability of nucleotide sequence information, such as a full length cDNA of SEQ ID NO: 1 (See FIG. 9), enables preparation of an isolated nucleic acid molecule of the invention by oligonucleotide synthesis. Synthetic oligonucleotides may be prepared by the phosphoramidite method employed in the Applied Biosystems 380A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Synthetic DNA molecules constructed by such means may then be cloned and amplified in an appropriate vector. Nucleic acid sequences encoding hRif1 may be isolated from appropriate biological sources using methods known in the art. In a preferred embodiment, a cDNA clone is isolated from a cDNA expression library of bacterial origin. In an alternative embodiment, utilizing the sequence information provided by the cDNA sequence, genomic clones encoding hRif1 may be isolated. Alternatively, cDNA or genomic clones having homology to hRif1 may be isolated from other species, using oligonucleotide probes corresponding to predetermined sequences within the hRif1 gene.

In accordance with the present invention, nucleic acids having the appropriate level of sequence homology with the protein coding region of SEQ ID NO: 1 may be identified by using hybridization and washing conditions of appropriate stringency. For example, hybridizations may be performed using a hybridization solution comprising: 5×SSC, 5× Denhardt's reagent, 0.5-1.0% SDS, 100 micrograms/ml denatured, fragmented salmon sperm DNA, 0.05% sodium pyrophosphate and up to 50% formamide. Hybridization is generally performed at 37-42° C. for at least six hours. Following hybridization, filters are washed as follows: (1) 5 minutes at room temperature in 2×SSC and 0.5-1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$T_m = 81.5° C. 16.6 \text{ Log } [Na+] + 0.41 (\% G+C) - 0.63 (\% \text{formamide}) - 600/\#bp$ in duplex As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

As can be seen from the above, the stringency of the hybridization and wash depend primarily on the salt concentration and temperature of the solutions. In general, to maximize the rate of annealing of the two nucleic acid molecules, the hybridization is usually carried out at 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 micrograms/ml denatured salmon sperm DNA at 42° C. and wash in 2×SSC and 0.5% SDS at 55° C. for 15 minutes. A high stringency hybridization is defined as hybridization in 6×SSC, 5× Denhardt's solution, 0.5% SDS and 100 micrograms/ml denatured salmon sperm DNA at 42° C. and wash in 1×SSC and 0.5% SDS at 65° C. for 15 minutes. A very high stringency hybridization is defined as hybridization in 6×SSC, 5× Denhardt's solution, 0.5% SDS and 100 micrograms/ml denatured salmon sperm DNA at 42° C. and wash in 0.1×SSC and 0.5% SDS at 65° C. for 15 minutes.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell. Genomic clones of the invention encoding a hRif1 gene may be maintained in lambda phage FIX II (Stratagene).

hRif1-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of a cDNA of SEQ ID NO: 1. Such oligonucleotides are useful as probes for detecting or isolating genes related to hRif1.

It will be appreciated by persons skilled in the art that variants (e.g., allelic variants) of these sequences exist in bacterial populations and/or species, and must be taken into account when designing and/or utilizing oligonucleotides of the invention. Accordingly, it is within the scope of the present invention to encompass such variants, with respect to the hRif1 sequences disclosed herein or the oligonucleotides targeted to specific locations on the respective genes or RNA transcripts. With respect to the inclusion of such variants, the term "natural allelic variants" is used herein to refer to various specific nucleotide sequences and variants thereof that would occur in a given DNA population. Genetic polymorphisms giving rise to conservative or neutral amino acid substitutions in the encoded protein are examples of such variants. Additionally, the term "substantially complementary" refers to oligonucleotide sequences that may not be perfectly matched to a target sequence, but the mismatches do not materially affect the ability of the oligonucleotide to hybridize with its target sequence under the conditions described.

Thus, the coding sequence may be that shown in, for example, SEQ ID NO: 1, or it may be a mutant, variant, derivative or allele of this sequence. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in SEQ ID NO: 1, but which encodes a polypeptide with the same amino acid sequence.

On the other hand, the encoded polypeptide may comprise an amino acid sequence which differs by one or more amino acid residues from the amino acid sequence shown in SEQ ID NO: 2. See FIG. 10. Nucleic acid encoding a polypeptide which is an amino acid sequence mutant, variant, derivative or allele of the sequence shown in SEQ ID NO: 2 is further provided by the present invention. Nucleic acid encoding such a polypeptide may show greater than 60% identity with the coding sequence shown in SEQ ID NO: 1, greater than about 70% identity, greater than about 80% identity, greater than about 90% identity or greater than about 95% identity.

The present invention provides a method of obtaining a nucleic acid of interest, the method including hybridization of a probe having part or all of the sequence shown in SEQ ID NO: 1, or a complementary sequence thereto, to target the nucleic acid. Successful hybridization leads to isolation of nucleic acid which has hybridized to the probe, which may involve one or more steps of polymerase chain reaction (PCR) amplification.

Such oligonucleotide probes or primers, as well as the full-length sequence (and mutants, alleles, variants, and derivatives) are useful in screening a test sample containing nucleic acids for the presence of alleles, mutants or variants of hRif1, the probes hybridizing with a target sequence from a sample obtained from a cell, tissue, or organism being tested. The conditions of the hybridization can be controlled to minimize non-specific binding. Preferably stringent to moderately stringent hybridization conditions are used. The skilled person is readily able to design such probes, label them and devise suitable conditions for hybridization reactions, assisted by textbooks such as Sambrook et al (1989) and Ausubel et al (1992).

In some preferred embodiments, oligonucleotides according to the present invention that are fragments of the sequences shown in SEQ ID NO: 1, or any allele associated with hRif1 activity, are at least about 10 nucleotides in length, more preferably at least 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence encoding a homolog or ortholog of hRif1.

Polypeptides: hRif1 is the first polypeptide that has been demonstrated to have properties that enable its use as an indicator of the status of ATM kinase activity in a cell. As described herein for the first time, hRif1 localizes to sites of DNA damage following treatment with conditions/agents that cause such damage (e.g., irradiation), but only in the presence of wild type (normal) ATM kinase activity levels. In the absence of ATM kinase activity, such as is observed in ATM null homozygous cells, hRif1 does not localize to sites of DNA damage. Thus, methods and agents useful for detecting hRif1 localization may be used to advantage to assess ATM kinase status in a cell or a sample isolated from a patient, in particular after exposure to conditions/agents that result in DNA damage.

A full-length hRif1 protein of the present invention may be prepared in a variety of ways, according to known methods. The protein may be purified from appropriate sources. This is not, however, a preferred method due to the low amount of protein likely to be present in a given cell type at any time. The availability of nucleic acid molecules encoding hRif1 enables production of this protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of hRif1 may be produced by expression in a suitable prokaryotic or eukaryotic system. For example, part or all of a DNA molecule, such as a cDNA of SEQ ID NO: 1, may be inserted into a plasmid vector adapted for expression in a bacterial cell, such as E. coli. Such vectors comprise regulatory elements necessary for expression of the DNA in a host cell (e.g. E. coli) positioned in such a manner as to permit expression of the DNA in the host cell. Such regulatory elements required for expression include promoter sequences, transcription initiation sequences and, optionally, enhancer sequences.

hRif1 produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

hRif1 of the invention, prepared by the aforementioned methods, may be analyzed according to standard procedures. For example, such proteins may be subjected to amino acid sequence analysis, according to known methods.

Polypeptides which are amino acid sequence variants, alleles, derivatives or mutants are also provided by the present invention. A polypeptide which is a variant, allele, derivative, or mutant may have an amino acid sequence that differs from that given in SEQ ID NO: 2 by one or more of addition, substitution, deletion and insertion of one or more amino acids. Preferred such polypeptides have hRif1 function, that is to say have one or more of the following properties: an ability to localize to sites of induced DNA damage in the presence of normal (wild type) ATM kinase activity levels and not localize to these sites in the absence of normal ATM kinase activity levels; immunological cross-reactivity with an antibody reactive with the polypeptide for which the sequence is given in SEQ ID NO: 2; and sharing an epitope with the polypeptide for which the sequence is given in SEQ ID NO: 2 (as determined for example by immunological cross-reactivity between the two polypeptides.

A polypeptide which is an amino acid sequence variant, allele, derivative or mutant of the amino acid sequence shown in SEQ ID NO: 2 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in SEQ ID NO: 2 by insertion, addition, substitution or deletion of 1 amino acid, 2, 3, 4, 5-10, 10-20, 20-30, 30-40, 40-50, 50-100, 100-150, or more than 150 amino acids. For amino acid "homology", this may be understood to be identity or similarity (according to the established principles of amino acid similarity, e.g., as determined using the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used including without limitation, BLAST (Altschul et al. (1990 J. Mol. Biol. 215:405-410); FASTA (Pearson and Lipman (1998) PNAS USA 85:2444-2448) or the Smith Waterman algorithm (Smith and Waterman (1981) J. Mol. Biol. 147:195-197) generally employing default parameters. Use of either of the terms "homology" and "homologous" herein does not necessarily imply any evolutionary relationship between the compared sequences. The terms are used similarly to the phrase "homologous recombination", i.e., the terms merely require that the two nucleotide sequences are sufficiently similar to recombine under appropriate conditions.

A polypeptide according to the present invention may be used in screening assays for molecules which affect or modulate hRif1 activity or function. Such molecules may be useful for research purposes.

Methods for Making Antibodies Immunologically Specific for hRif1; The methods of the present invention encompass the use of antibodies or fragments thereof capable of specifically or selectively recognizing one or more hRif1 epitopes. Such antibodies may include, but are not limited to, polyclonal antibodies, monoclonal antibodies (mAbs), humanized or chimeric antibodies, single chain antibodies, Fab fragments, F(ab')$_2$ fragments, Fv fragments, fragments produced by a Fab expression library, anti-idiotypic (anti-Id) antibodies, and epitope-binding fragments of any of the above.

Such antibodies may be used, for example, in the detection of hRif1 in a biological sample and may, therefore, be utilized as part of a diagnostic or prognostic technique whereby cells isolated from a patient may be tested to determine if hRif1 localizes to sites of DNA damage following treatment capable of inducing DNA damage such as those described herein and known in the art. As indicated herein for the first time, the ability of hRif1 to localize to sites of DNA damage is dependent on normal (or wildtype) levels ATM kinase activity. Thus, hRif1 localization to sites of DNA damage serves as a positive indicator of or readout for ATM kinase activity. Antibodies immunologically specific for hRif1 are, therefore, useful for visualizing hRif1 localization and, by extension, are also tools for detecting the status of the ATM kinase in a cell. Such antibodies are included as reagents in a kit for use in a diagnostic or prognostic technique. Such antibodies may also be utilized in conjunction with, for example, compound screening methods, such as those described herein below, for the evaluation of the effect of test compounds on hRif1 gene product levels and/or activity, and ATM kinase gene product levels and/or activity.

Described herein are methods for the production of antibodies or fragments thereof. Any of such antibodies or fragments thereof may be produced by standard immunological methods or by recombinant expression of nucleic acid molecules encoding the antibody or fragments thereof in an appropriate host organism.

For the production of antibodies against hRif1, various host animals may be immunized by injection with hRif1, or a portion thereof, or a fusion protein comprising part or all of hRif1. Such host animals may include, but are not limited to rabbits, mice, and rats. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as hRif1, or an antigenic functional derivative thereof. For the production of polyclonal antibodies, host animals such as those described above, may be immunized by injection with hRif1 or a fragment thereof supplemented with adjuvants as described above.

Monoclonal antibodies (mAbs), which are homogeneous populations of antibodies to a particular antigen or epitope thereof, may be obtained by any technique that provides for the production of antibody molecules by continuous cell lines in culture. These include, but are not limited to, the hybridoma technique of Kohler and Milstein, (1975, *Nature* 256: 495; and U.S. Pat. No. 4,376,110), the human B-cell hybridoma technique (Kosbor et al., 1983, *Immunology Today* 4:72; Cole et al., 1983, *Proc. Natl. Acad. Sci. USA* 80:2026), and the EBV-hybridoma technique (Cole et al., 1985, *Monoclonal Antibodies And Cancer Therapy*, Alan R. Liss, Inc., pp. 77). Such antibodies may be of any immunoglobulin class including IgG, IgM, IgE, IgA, IgD and any subclass thereof. A hybridoma producing a mAb of this invention may be cultivated in vitro or in vivo. Production of high titers of mAbs in vivo renders this method a particularly preferred method of production of hRif1 antibodies.

Techniques developed for the production of "chimeric antibodies" (Morrison et al., 1984, Proc. Natl. Acad. Sci., 81, 6851-6855; Neuberger et al., 1984, Nature 312, 604-608; Takeda et al., 1985, Nature 314, 452-454), whereby the genes from a mouse antibody molecule of appropriate antigen specificity are spliced to genes from a human antibody molecule of appropriate biological activity, are also encompassed by the present invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 5,816,397). The invention thus contemplates chimeric antibodies that are specific or selective for hRif1.

Examples of techniques that have been developed for the production of humanized antibodies are known in the art. See, e.g., Queen, U.S. Pat. No. 5,585,089 and Winter, U.S. Pat. No. 5,225,539. An immunoglobulin light or heavy chain variable region consists of a "framework" region interrupted by three hypervariable regions, referred to as complementarity-determining regions (CDRs). The extent of the framework region and CDRs has been precisely defined. See, "Sequences of Proteins of Immunological Interest", Kabat, E. et al., U.S. Department of Health and Human Services (1983). Briefly, humanized antibodies are antibody molecules from non-human species having one or more CDRs from the non-human species and framework regions from a human immunoglobulin molecule. The invention includes the use of humanized antibodies that are specific or selective for hRif1 in the methods of the invention.

The methods of the invention encompass the use of an antibody or derivative thereof comprising a heavy or light chain variable domain, said variable domain comprising (a) a set of three complementarity-determining regions (CDRs), in which said set of CDRs are from a monoclonal antibody to a gene product encoded by a hRif1 nucleic acid sequence (e.g., SEQ ID NO: 1), and (b) a set of four framework regions, in which said set of framework regions differs from the set of framework regions in the hRif1 monoclonal antibody, and in which said antibody or derivative thereof immunospecifically binds to the gene product encoded by a hRif1 gene sequence. Preferably, the set of framework regions is from a human monoclonal antibody, e.g., a human monoclonal antibody that does not bind the gene product encoded by the hRif1 gene sequence.

Phage display technology can be used to increase the affinity of an antibody to hRif1. This technique is useful for obtaining high affinity antibodies to hRif1 that could be used for the diagnosis and/or prognosis of a subject with, for example, a cancer. The technology, referred to as affinity maturation, employs mutagenesis or CDR walking and re-selection using a hRif1 antigen to identify antibodies that bind with higher affinity to the antigen when compared with the initial or parental antibody (see, e.g., Glaser et al., 1992, *J. Immunology* 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contact with the immobilized mutants containing labeled antigen. Any screening method known in the art can be used to identify mutant antibodies with increased avidity to the antigen (e.g., ELISA) (See Wu et al., 1998, *Proc Natl. Acad Sci. USA* 95:6037; Yelton et al., 1995, *J. Immunology* 155:1994). CDR walking which randomizes the light chain is also possible (See Schier et al., 1996, *J. Mol. Bio.* 263:551).

Alternatively, techniques described for the production of single chain antibodies (U.S. Pat. No. 4,946,778; Bird, 1988, *Science* 242:423; Huston et al., 1988, *Proc. Nat. Acad. Sci. USA* 85:5879; and Ward et al., 1989, *Nature* 334:544) can be adapted to produce single chain antibodies against hRif1. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, *Science* 242:1038).

The methods of the invention include using an antibody to a hRif1 polypeptide, peptide or other derivative, or analog thereof that is a bispecific antibody (see generally, e.g., Fanger and Drakeman, 1995, *Drug News and Perspectives* 8:133-137). Such a bispecific antibody is genetically engineered to recognize both (1) an epitope and (2) one of a variety of "trigger" molecules, e.g., Fc receptors on myeloid cells, and CD3 and CD2 on T-cells, that have been identified as being able to cause a cytotoxic T-cell to destroy a particular target. Such bispecific antibodies can be prepared either by chemical conjugation, hybridoma, or recombinant molecular biology techniques known to the skilled artisan.

Antibody fragments that recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, *Science* 246:1275-1281) to allow rapid and easy identification of monoclonal Fab fragments with the desired specificity.

Antibodies, for example, or fragments of antibodies, such as those described herein, useful in the present invention may be used to quantitatively or qualitatively detect the presence of hRif1 polypeptides or naturally occurring variants or peptide fragments thereof. The antibodies (or fragments thereof) useful in the present invention may, additionally, be employed histologically, as in immunofluorescence or immunoelectron microscopy, for in situ detection of hRif1 gene products or conserved variants or peptide fragments thereof. In situ detection may be accomplished by removing a histological specimen from a subject, such as paraffin embedded sections of tissue, e.g., lung tissues and applying thereto a labeled antibody of the present invention. The antibody (or fragment) is preferably applied by overlaying the labeled antibody (or fragment) onto a biological sample. Since the hRif1 gene product is expressed as an intracellular protein, it is desirable to introduce the antibody inside the cell, for example, by making the cell membrane permeable. Under circumstances wherein hRif1 polypeptides (of exogenous origin and genetically engineered to be expressed at the cell surface) are also expressed on the cell surface, cells can be directly labeled by applying antibodies that are specific or selective for hRif1 polypeptides or fragments thereof to the cell surface.

Through the use of such a procedure, it is possible to determine not only the presence of a hRif1 gene product, or naturally occurring variants thereof or peptide fragments, but also its distribution in the examined tissue. Using the methods of the present invention, those of ordinary skill will readily perceive that any of a wide variety of histological methods (such as staining procedures) can be modified in order to achieve such in situ detection.

Immunoassays for hRif1 polypeptides or conserved variants or peptide fragments thereof will typically comprise contacting a sample, such as a biological fluid, tissue or a tissue extract, freshly harvested cells, or lysates of cells which have been incubated in cell culture, in the presence of an antibody that specifically or selectively binds to a hRif1 gene product, e.g., a detectably labeled antibody capable of identifying hRif1 polypeptides or conserved variants or peptide fragments thereof, and detecting the bound antibody by any of a number of techniques well-known in the art (e.g., Western blot, ELISA, FACS).

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled antibody that selectively or specifically binds to a hRif1 encoded polypeptide. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art are aware of many other suitable carriers for binding antibody or antigen, and are able to ascertain the same by use of routine experimentation.

The anti-hRif1 antibody can be detectably labeled by linking the same to an enzyme and using the labeled antibody in an enzyme immunoassay (EIA) (Voller, A., "The Enzyme Linked Immunosorbent Assay (ELISA)", 1978, *Diagnostic*

Horizons 2:1, Microbiological Associates Quarterly Publication, Walkersville, Md.); Voller, A. et al., 1978, *J. Clin. Pathol.* 31: 507-520; Butler, J. E., 1981, *Meth. Enzymol.* 73:482; Maggio, E. (ed.), 1980, *Enzyme Immunoassay*, CRC Press, Boca Raton, Fla.; Ishikawa, E. et al., (eds.), 1981, *Enzyme Immunoassay*, Kgaku Shoin, Tokyo). The enzyme that is bound to the antibody reacts with an appropriate substrate, preferably a chromogenic substrate, in such a manner as to produce a chemical moiety detectable, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect hRif1 encoded polypeptides through the use of a radioimmunoassay (RIA). See, for example, Weintraub, B., *Principles of Radioimmunoassays, Seventh Training Course on Radioligand Assay Techniques*, The Endocrine Society, March, 1986. The radioactive isotope can be detected by such means as the use of a gamma counter or a scintillation counter or by autoradiography.

An antibody of the invention can also be labeled with a fluorescent compound. When the fluorescently labeled antibody is exposed to light of the proper wavelength, its presence can be detected due to fluorescence emission. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody can also be detectably labeled by coupling it to a chemiluminescent compound. The presence of the chemiluminescent-tagged antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In various embodiments, the present invention provides methods for the measurement of hRif1 polypeptides, and the uses of such measurements in clinical applications using antibodies immunologically specific for hRif1.

Uses of hRif1-Encoding Nucleic Acids, hRif1 Polypeptides and Antibodies Thereto

Detection of hRif1 may be used to advantage to detect or assess the status of ATM kinase in a cell, tissue, or organism. hRif1 molecules and compositions of the invention may be used to advantage to treat patients with a hyperproliferative disorder. In some aspects of the invention, hRif1 molecules and agents capable of modulating hRif1 activity and/or ATM kinase activity identified using the methods of the invention can be used to render transformed cells in a cancer patient more susceptible to treatment with irradiation.

Additionally, hRif1 nucleic acids, proteins and antibodies thereto, according to this invention, may be used as a research tool to identify other proteins that are intimately involved in the DNA damage response.

hRif1-Encoding Nucleic Acids: hRif1-encoding nucleic acids may be used for a variety of purposes in accordance with the present invention. hRif1-encoding DNA, RNA, or fragments thereof may be used as probes to detect the presence of and/or expression of genes encoding hRif-like proteins. Methods in which hRif1-encoding nucleic acids may be utilized as probes for such assays include, but are not limited to: (1) in situ hybridization; (2) Southern hybridization (3) northern hybridization; and (4) assorted amplification reactions such as PCR. hRif1-encoding nucleic acids of the invention may also be utilized as probes to identify related genes from other bacterial, plant, insect or animal species. As is well known in the art, hybridization stringencies may be adjusted to allow hybridization of nucleic acid probes with complementary sequences of varying degrees of homology. Thus hRif1-encoding nucleic acids may be used to advantage to identify and characterize other genes of varying degrees of relation to hRif1, thereby enabling further characterization of the DNA damage response. Additionally, they may be used to identify genes encoding proteins that interact with hRif1 (e.g., by the "interaction trap" technique), which should further accelerate identification of the components involved in pathways involved in the DNA damage response.

Nucleic acid molecules, or fragments thereof, encoding hRif1 may also be utilized to control the production of hRif1, thereby regulating the amount of protein available to participate in DNA damage responses. Alterations in the physiological amount of hRif1 protein may dramatically affect the activity of other protein factors involved in the DNA damage response.

hRif1 and Antibodies Thereto: As described herein, purified hRif1 proteins, or fragments thereof, produced via expression of hRif1 encoding nucleic acids of the present invention may be used to produce polyclonal or monoclonal antibodies which also may serve as sensitive detection reagents for the presence and accumulation of hRif1 (or complexes containing hRif1) in human cells and potentially cells of related mammals and primates. Recombinant techniques enable expression of fusion proteins containing part or all of the hRif1 protein. The full length protein or fragments of the protein may be used to advantage to generate an array of monoclonal antibodies specific for various epitopes of the protein, thereby providing a potentially even greater sensitivity for detection of the protein in cells.

Polyclonal or monoclonal antibodies immunologically specific for hRif1 may be used in a variety of assays designed to detect and quantitate the protein. Such assays include, but are not limited to: (1) flow cytometric analysis; (2) immunochemical localization of hRif1 in cells; and (3) immunoblot analysis (e.g., dot blot, Western blot) of extracts from various cells. Additionally, as described above, anti-hRif1 antibodies, for example, can be used for purification of hRif1 and orthologs thereof (e.g., affinity column purification and immunoprecipitation).

Methods for Visualizing Rif1 Localization Patterns

Isolation of cells from a patient: Samples are isolated from subjects by any means routinely used in the art for such purposes. Cells in suspension, such as those found in blood (e.g., peripheral blood lymphocytes, metastasized tumor cells), lymph, ascites, and pleural effusion are well suited to assays described herein for detecting hRif1 localization patterns. Cells isolated from, e.g., lymph node fluid draining from a tumor site may be used effectively in the present assays to determine the status of the ATM gene in tumor cells sloughed from the tumor mass. Such cells may removed from the patient using, for example, a needle and syringe or other means useful for aspirating cells in suspension or solution.

Cells isolated from solid tissue are also useful in the present assays, but additional preparatory steps are advisable to ensure accuracy of detection. Tumor samples may, for example, be excised from a subject and treated by any means known to digest extracellular matrices so as to produce a single cell population of tumor cells in suspension. Tumor samples may, for example, be treated with an appropriate concentration of collagenase as described below.

Collagenase Treatment of Tissue Samples: Step 1; Weigh the tissue (e.g., a tumor sample) to determine how much collagenase solution to make. Collagenase [e.g., CLS3 type Collagenase Worthington Biochemical Corporation (Freehold, N.J. #LS004183)] is resuspended at 200 units/ml in media [e.g., M-1 99+Gentimycin (5 ug/ml)]. For 20-30 grams of normal tissue make up 100 ml of collagenase. Divide into 2 different digestions in two separate flasks to optimize for cellular viability which may vary as a function of tissue sensitivity to the collagenase treatment. Alternatively, for a tumor sample, 20 ml of collagenase solution is routinely used for the first gram of tissue and 10 ml for each additional gram. Step 2; Sterile filter the collagenase solution before use and deposit into, e.g., a sterile 250 ml Erlenmeyer flask with a sterile aluminum foil cap. Step 3; Cross cut the tumor using two sterile scalpels, being careful to cut the tissue, rather than tear it. Dice into small pieces, about 1 mm. Step 4; Transfer the diced tissue into the flask containing the sterile collagenase solution. Replace and secure the sterile top. Step 5; Transfer flask with diced tissue/collagenase solution into a 37° C. shaker or shaking water bath. Securely fasten the flask so it will stay upright. Set motion at 65 rpm. Leave overnight for collagenase to fully digest the tissue. Step 6; After overnight incubation, titrate the mixture 20 to 25 times using a sterile pipette. Transfer to centrifuge tubes and centrifuge the cells at 1000 rpm for 5 minutes at room temperature. Step 7; Wash/resuspend cell pellet in 10 ml M-199+G. Centrifuge at 1000 rpm for 5 minutes at room temperature. Repeat wash/resuspend and centrifugation steps two more times. Step 8; After the last wash, resuspend in 5 to 10 ml media. Determine cell density using, e.g., a Coulter Counter. Step 9; Plate the cells in appropriate media at a desired density such as those described in the Examples herein below.

Skilled practitioners would also be aware of other methods for digesting tumor samples to prepare cell suspensions therefrom. A variety of enzymes capable of digesting extracellular matrices may be used for such experimental purposes. A skilled artisan would be able to determine which particular enzymes and experimental parameters would be well suited for digestion of a particular tumor type.

Cell suspensions, isolated or generated as described above, are subsequently irradiated as set forth herein below in the Examples. The level of gamma irradiation used to treat cell suspensions may range from 0.1 and 50 Gray (Gy). Within this broad range, a particular range of 0.5 and 10 Gy may used to treat cell suspensions in the present assay. In a particular embodiment, cells are irradiated with 1-10 Gy from a $^{137}$Cs source at a dose rate of 3 Gy per minute and incubated for 30 minutes at 37° C prior to processing for immunofluorescence as described herein. Alternatively, cells may be exposed to γ-irradiation using a $^{137}$CS source at a rate of 7.7 Gray/min in 6 cm dishes as described herein. As indicated herein below, Rif1 localization to sites of DNA damage following irradiation occurs rapidly. Rif1 re-localization to foci can be apparent within 5 minutes and persists for many hours. Rif1 foci may be visualized in a time frame ranging from approximately 5 minutes to 4 hours after exposure to irradiation.

A skilled artisan would appreciate that any form of ionizing radiation may be used in the method of the present invention. A determination of appropriate dosage ranges of other forms of ionizing radiation would be well within the capabilities of a skilled practitioner and would require minimal experimentation.

Radiomimetic drugs, such as etoposide, may also be used in assays of the present invention because these treatments can trigger formation of double stranded DNA breaks (DSBs) which, in turn, results in the localization of hRif1 to the resultant DSBs. Radiomimetic drugs may be added to culture media and cells are fixed 1-8 hours later. Examples of radiomimetic drugs include, but are not limited to, etoposide, neocarzinostatin, campothecin, and bleomycin. Concentrations and vehicle vary for each drug and such information is readily available and known to skilled practitioners.

Alternatively, whole tissue (e.g., a tumor sample) can be isolated and irradiated in culture. A skilled practitioner would be aware of methods for optimizing the irradiation step to maximize uniformity and penetrance of the irradiation. Sections can then be sliced from the tumor using routine protocols and processed for immunofluorescence as described herein below in the Examples.

Cell suspensions may be fixed by a variety of means known in the art. Fixation protocols adapted for the present invention are described in detail in the Examples presented herein. Fixation protocols described herein may also be adapted for use with tissue sections. Alternatively, protocols for fixing tissue sections are well known in the art and can be accessed from a variety of readily available laboratory manuals.

Antibodies immunologically specific for hRif1 are used for detecting the localization pattern of hRif1 polypeptide in treated cells (e.g., irradiated cells) using immunofluorescence protocols such as those described in the Examples presented herein. The polyclonal anti-hRif1 antibodies described herein may be used in a range of concentrations from approximately 0.1 ng/microliter to 5.0 ng/microliter for immunofluorescence procedures. Polyclonal anti-hRif1 antibodies described herein may be used at a particular final concentration of approximately 0.5 ng/microliter for applications involving immunofluorescence.

Methods for generating antibodies immunologically specific for hRif1 are described in detail herein. Such methods include those used for generating monoclonal and polyclonal hRif1 antibodies. As described in detail herein, hRif1 antibodies can be generated in response to full length hRif1, or any antigenic fragment thereof (e.g., an antigenic peptide), or a fusion protein comprising all or an antigenic fragment of hRif1.

Anti-hRif1 antibodies may be labeled directly to facilitate detection of antibodies bound to hRif1 protein in a cell. Alternatively, secondary antibodies which recognize an epitope on the primary antibody (i.e., the anti-hRif1 antibody) may be labeled to enable detection of hRif1-antibody complexes. Methods wherein labeled secondary or tertiary antibodies are used to visualize the binding of a primary antibody to its specific target are a matter of routine practice. Indeed, labeling of secondary or tertiary antibodies is generally considered to amplify the signal and, thereby, promote the level of detection to enable visualization of rare antibody-antigen complexes. Various labels that are useful for such purposes are known in the art and described herein.

Visualization of immunofluorescent complexes comprising hRif1 and associated antibodies may be visualized using any means available for detection of fluorescently labeled molecules at a level of resolution sufficient for detecting intracellular localization patterns, such as localization to sites of DNA damage. Such means include fluorescent microscopes equipped with high magnification lenses, and confocal microscopes. Skilled practitioners are familiar with the technical parameters required for detection at this level of resolution and are knowledgeable with regard to the instrumentation required for such determinations.

From the foregoing discussion, it can be seen that hRif1-encoding nucleic acids, hRif1 expressing vectors, and anti-hRif1 antibodies of the invention can be used to produce large quantities of hRif1 protein, detect hRif1 gene expression and alter hRif1 accumulation for purposes of assessing the genetic and protein interactions involved in the DNA damage response. In particular, the detection of hRif1 localization in cells that have undergone conditions resulting in DNA damage may be used as a sensitive means for detecting the ATM kinase genotype or status of a cell. In so doing, the ATM kinase genotype of a subject from which a cell or population of cells (e.g., a sample) can be assessed.

General Methods for Identifying Compounds Capable of Modulating hRif1 Activity

A structure of the hRif1 can be determined by standard means familiar in the art. Generally, such means begin with polypeptide modeling that utilizes a selected protein structure derived by conventional means, e.g., X-ray crystallography, NMR, homology modeling, or the like. Such methods are known to those skilled in the art.

Based on information presented herein, suitable peptide targets in hRif1 include, but are not limited to, those residues and regions listed below. Suitable peptide targets in hRif1 include the CRI, CRII, and CRIII regions. Also included are critical residues and small peptides encompassing these critical residues (e.g. 5-10 residue peptides comprising these residues and flanking residues thereof) which are identified on the basis of high resolution information determined for hRif1.

In one embodiment of the invention, a crystal structure of hRif1 is used as a target in a virtual ligand screening procedure that seeks to identify, via computer docking methods, candidate compounds from a vast compound library which bind with high affinity to the target site.

In another embodiment, structural information pertaining to hRif1 is used to design compounds predicted to bind to hRif1 and interfaces formed between molecules (e.g., polypeptides, nucleic acid sequences), and such compounds are tested for high affinity binding.

In specific embodiments, candidate compounds and "designed compounds" are selected which modulate binding of hRif1 to DNA and DNA/protein complexes. Such compounds may either enhance or inhibit binding of hRif1 to DNA. Such compounds may, in turn, effectuate an increase or a decrease in hRif1 binding to sites of DNA damage. Alternatively, such compounds may alter the ability of hRif1 to act downstream of ATM kinase. Modulation of hRif1 activity may be assessed, for example, in a cell-based assay wherein the ability of hRif1 to bind to sites of DNA damage following treatment with agents/conditions known to induce such damage (such as those described herein and known in the art) can be determined. In one embodiment, cells used in such assays comprise wild type (normal) ATM kinase activity (e.g., ATM/ATM homozygous or ATM/ATM-heterozygous cells). In an alternate embodiment, cell-based assays utilize cells with impaired levels of ATM kinase activity (e.g., ATM-/ATM-homozygous cells or ATM null cells). Compounds derived or obtained from either approach scoring the highest in the docking procedure can also be tested in cell-free assays, as well as cell-based assays (which are both described in detail herein below), to determine their efficacy in modulating hRif1 activity.

Any compounds which show efficacy in biological assays may then be co-crystallized with hRif1 to identify the binding site(s). In a further embodiment of the invention, candidate compounds able to bind hRif1 are modified by methods known in the art to further improve specific characteristics, e.g., to increase efficacy and/or specificity and/or solubility. Selected compounds exhibiting the most desired characteristics are designated lead compounds, and further tested in, for example, animal models of hyperproliferative disorders to measure their efficacy.

Virtual Ligand Screening Via Flexible Docking Technology

Current docking and screening methodologies can select small sets of likely lead candidate ligands from large libraries of compounds using a specific protein structure. Such methods are described, for example, in Abagyan and Totrov (2001) Current Opinion Chemical Biology 5:375-382, herein specifically incorporated by reference in its entirety.

Virtual ligand screening (VLS) based on high-throughput flexible docking is useful for designing and identifying compounds able to bind to a specific protein structure. VLS can be used to virtually sample a large number of chemical molecules without synthesizing and experimentally testing each one. Generally, the methods start with polypeptide modeling which uses a selected protein structure derived by conventional means, e.g., X-ray crystallography, NMR, and/or homology modeling. A set of compounds and/or molecular fragments are then docked into the selected binding site using any one of the existing docking programs, such as for example, MCDOCK (Liu et al. (1999) J. Comput. Aided Mol. Des. 13:435-451), SEED (Majeux et al. (1999) Proteins 37:88-105; DARWIN (Taylor et al. (2000) Proteins 41:173-191; MM (David et al. (2001) J. Comput. Aided Mol. Des. 15:157-171. Compounds are scored as ligands, and a list of candidate compounds predicted to possess the highest binding affinities are generated for further in vitro and in vivo testing and/or chemical modification.

In one approach of VLS, molecules are "built" into a selected binding pocket prior to chemical generation. A large number of programs are designed to "grow" ligands atom-by-atom [see, for example, GENSTAR (Pearlman et al. L(1 993) J. Comput. Chem. 14:1184), LEGEND (Nishibata et al. (1993) J. Med. Chem. 36:2921-2928), MCDNLG (Rotstein et al. (1993) J. Comput-Aided Mol. Des. 7:23-43), CONCEPTS (Gehlhaar et al. (1995) J. Med. Chem 38:466-472] or fragment-by-fragment [see, for example, GROUPBUILD (Rotsein et al. (1993) J. Med. Chem. 36:1700-1710), SPROUT (Gillet et al. (1993) J. Comput. Aided Mol. Des. 7:127-153), LUDI (Bohm (1992) J. Comput. Aided Mol. Des. 6:61-78), BUILDER (Roe (1995) J. Comput. Aided Mol. Des. 9:269-282), and SMOG (DeWitte et al. (1996) J. Am. Chem. Soc. 118:11733-11744].

Methods for scoring ligands for a particular protein are known which allow discrimination between the small number of molecules able to bind the protein structure and the large number of non-binders. See, for example, Agagyan et al. (2001) supra, for a report on the growing number of ligands successfully identified via virtual ligand docking and screening methodologies.

For example, Nishibata et al. (1993) J. Med. Chem 36:2921-2928, describe the ability of a structure construction program to generate inhibitory molecules based on the three-dimension structure of the active site of a molecule, dihydrofolate reductase. The program was able to predict molecules having a similar structure to four known inhibitors of the enzyme, providing strong support that new lead compounds can be obtained with knowledge of the target three-dimensional structure. Similarly, Gillet et al. (1993) J. Computer Aided Mol. Design 7:127-153 describe structure generation through artificial intelligence techniques based on steric constraints (SPROUT).

Agents Identified by the Screening Methods of the Invention

The invention provides methods for identifying agents (e.g., candidate compounds or test compounds) that bind with high affinity to hRif1. Agents identified by the screening method of the invention are useful as candidate anti-hyperproliferative disorder therapeutics.

Examples of agents, candidate compounds or test compounds include, but are not limited to, nucleic acids (e.g., DNA and RNA), carbohydrates, lipids, proteins, peptides, peptidomimetics, small molecules and other drugs. Exemplary nucleic acids determined to be capable of modulating hRif1 activity include, but are not limited to: hRif1 siRNA molecules described herein. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233, each of which is incorporated herein in its entirety by reference.

Libraries of compounds may be presented, e.g., presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869) or phage (Scott and Smith (19900 Science 249:386-390; Devlin (1990) Science 249:404-406; Cwirla et al. (1990) Proc. Natl. Acad. Sci. USA 87:6378-6382; and Felici (1991) J. Mol. Biol. 222:301-310), each of which is incorporated herein in its entirety by reference.

Screening Assays

Small molecules identified through the above described virtual ligand docking and screening methodologies are further tested in in vitro and in vivo assays. In one embodiment, agents that interact with (i.e., bind to) hRif1 are identified in a cell-based assay system.

In accordance with this embodiment, cells expressing hRif1 or a functional fragment thereof, are contacted with a candidate compound or a control compound and the ability of the candidate compound to interact with hRif1 is determined. If desired, this assay may be used to screen a plurality (e.g. a library) of candidate compounds. The cell, for example, can be of prokaryotic origin (e.g., *E. coli*) or eukaryotic origin (e.g., yeast or mammalian). Exemplary cells and cell lines that can be used in cell-based assays include, but are not limited to, IMR90 primary human fibroblasts (ATCC, early passage), GM847 (ATCC), hTERT/BJ, SV40-transformed NBS-1 LB1 cells [Zdzienicka. (1999) Biochimie 81,107-116], and ATLD-3 and ATLD-4 cells [Stewart et al. (1999) Cell 99, 577-587], U2OS cells (ATCC), HCC1937 cells (ATCC) and HCT-15 cells (ATCC). Depending on the goal of the cell-based assay performed, a skilled artisan would know to select cells that express either wild type levels of ATM kinase activity or are ATM null.

Further, the cells can express hRif1 or a fragment thereof endogenously or be genetically engineered to express hRif1 or a hRif1 fragment. In certain instances, hRif1 or a hRif1 fragment is labeled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between hRif1 and a candidate compound. The ability of the candidate compound to bind to hRif1 can be determined by methods known to those of skill in the art. For example, the interaction between a candidate compound and hRif1 can be determined by flow cytometry, a scintillation assay, immunoprecipitation or immunoblot analysis.

In another embodiment, agents that interact with (i.e., bind to) hRif1, or a functional fragment thereof, are identified in a cell-free assay system. In accordance with this embodiment, a native or recombinant hRif1 or fragment thereof is contacted with a candidate compound or a control compound and the ability of the candidate compound to interact with hRif1 is determined. If desired, this assay may be used to screen a plurality (e.g. a library) of candidate compounds. In one embodiment, hRif1 or fragment thereof is first immobilized, by, for example, contacting with an immobilized antibody which specifically recognizes and binds to hRif1, or by contacting a purified preparation of hRif1 or fragment thereof, with a surface designed to bind proteins. hRif1 or a fragment thereof may be partially or completely purified (e.g., partially or completely free of other polypeptides) or part of a cell lysate. Further, hRif1 or a fragment thereof may be a fusion protein comprising hRif1 or a biologically active portion thereof, and a domain such as glutathionine-S-transferase. Alternatively, hRif1 or a fragment thereof can be biotinylated using techniques well known to those of skill in the art (e.g., biotinylation kit, Pierce Chemicals; Rockford, Ill.). The ability of a candidate compound to interact with hRif1 can be determined by detection methods known to those of skill in the art.

In another embodiment, agents that modulate the hRif1 activity are identified or tested in an animal model. Examples of suitable animals include, but are not limited to, mice, rats, rabbits, monkeys, guinea pigs, dogs and cats. As indicated herein above, the ability of human Rif1 antibodies to cross-react with Rif1 orthologs/homologs of these species is predictive of the utility of the present method for mammals other than humans. Preferably, the animal used represents a model of a hyperproliferative disorder. In accordance with this embodiment, the test compound or a control compound is administered (e.g., orally, rectally or parenterally such as intraperitoneally or intravenously) to a suitable animal and the effect on the level of Rif1 activity is determined.

A skilled practitioner would appreciate that the hRif1 RNAi (siRNA) molecules described herein are exemplary hRif1 modulatory agents. Specifically, these RNAi molecules have been demonstrated herein to significantly reduce and/or eliminate hRif1 expression levels in cells into which the molecules have been introduced.

The basic molecular biology techniques used to practice the methods of the invention are well known in the art, and are described for example in Sambrook et al., 1989, *Molecular Cloning: A Laboratory Manual*, Cold Spring Harbor Laboratory, New York; Ausubel et al., 1988, *Current Protocols in Molecular Biology*, John Wiley & Sons, New York; and Ausubel et al., 2002, *Short Protocols in Molecular Biology*, John Wiley & Sons, New York).

Therapeutic Uses of Agents Able to Bind and/or Modulate hRif1 and/or ATM Kinase Activity The invention provides for treatment of hyperproliferative disorders by administration of a therapeutic compound identified using the above-described methods. Such compounds include, but are not limited to proteins, peptides, protein or peptide derivatives or analogs, antibodies, nucleic acids, and small molecules.

The invention provides methods for treating patients afflicted with a hyperproliferative disorder comprising administering to a subject an effective amount of a compound identified by a method of the invention. In a particular aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu (1987) J. Biol. Chem. 262:4429-4432), and construction of a nucleic acid as part of a retroviral or other vector. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally, e.g., by local infusion during surgery, topical application, e.g., by injection, by means of a catheter, or by means of an implant, said implant being of a porous, non-porous, or gelatinous material, including membranes, such as sialastic membranes, or fibers.

In another embodiment, the compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., a target tissue or tumor, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533).

Pharmaceutical Compositions

The present invention also provides pharmaceutical compositions. Such compositions comprise a therapeutically effective amount of an agent, and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, incorporated in its entirety by reference herein. Such compositions contain a therapeutically effective amount of the compound, preferably in purified form, together with a suitable amount of carrier so as to provide a form for proper administration to a subject. The formulation should suit the mode of administration.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of a hyperproliferative disorder (e.g., cancer) can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Suppositories generally contain active ingredient in the range of 0.5% to 10% by weight; oral formulations preferably contain 10% to 95% active ingredient. Effective doses may be extrapolated from dose-response curves derived from in vitro or animal model test systems.

Nucleic Acids

The invention provides methods of identifying agents capable of binding and/or modulating hRif1 and/or ATM kinase. Accordingly, the invention encompasses administration of a nucleic acid encoding a peptide or protein capable of modulating an activity of hRif1 and/or ATM kinase, as well as antisense sequences or catalytic RNAs capable of interfering with the expression and/or activity of hRif1 and/or ATM kinase.

In one embodiment, a nucleic acid comprising a sequence encoding a peptide or protein capable of competitively binding to hRif1 or ATM kinase is administered. Any suitable methods for administering a nucleic acid sequence available in the art can be used according to the present invention.

Methods for administering and expressing a nucleic acid sequence are generally known in the area of gene therapy. For general reviews of the methods of gene therapy, see Goldspiel et al. (1993) Clinical Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; and Morgan and Anderson (1993) Ann. Rev. Biochem. 62:191-217; May (1993) TIBTECH 11 (5): 155-215. Methods commonly known in the art of recombinant DNA technology which can be used in the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

In a particular aspect, the compound comprises a nucleic acid encoding a peptide or protein capable of binding to and/or modulating an activity of hRif1 and/or ATM kinase (such as the ability to survive DNA damage following exposure to radiation), such nucleic acid being part of an expression vector that expresses the peptide or protein in a suitable host. In particular, such a nucleic acid has a promoter operably linked to the coding region, said promoter being inducible or constitutive (and, optionally, tissue-specific). In a different embodiment, a nucleic acid molecule is used in which the coding sequences and any other desired sequences are flanked by regions that promote homologous recombination at a desired site in the genome, thus providing for intrachromosomal expression of the nucleic acid (Koller and Smithies (1989) Proc. Natl. Acad. Sci. USA 86:8932-8935; Zijlstra et al. (1989) Nature 342:435-438).

Delivery of the nucleic acid into a subject may be direct, in which case the subject is directly exposed to the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject, known as "ex vivo gene therapy".

In another embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286); by direct injection of naked DNA; by use of microparticle bombardment (e.g., a gene gun; Biolistic, Dupont); by coating with lipids, cell-surface receptors or transfecting agents; by encapsulation in liposomes, microparticles or microcapsules; by administering it in linkage to a peptide which is known to enter the nucleus; or by administering it in linkage to a ligand subject to receptor-mediated endocytosis (see, e.g., Wu and Wu, 1987, J. Biol. Chem. 262:4429-4432), which can be used to target cell types specifically expressing the receptors.

In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al. (1989) Nature 342:435-438).

In a further embodiment, a retroviral vector can be used (see Miller et al. (1993) Meth. Enzymol. 217:581-599). Such retroviral vectors have been modified to delete retroviral sequences that are not necessary for packaging of the viral genome and integration into host cell DNA. The nucleic acid encoding a desired polypeptide to be used in gene therapy is cloned into the vector, which facilitates delivery of the gene into a subject. More detail about retroviral vectors can be found in Boesen et al. (1994) Biotherapy 6:291-302, which describes the use of a retroviral vector to deliver the mdr1 gene to hematopoietic stem cells in order to render the stem cells more resistant to chemotherapy. Other references illustrating the use of retroviral vectors in gene therapy are: Clowes et al. (1994) J. Clin. Invest. 93:644-651; Kiem et al. (1994) Blood 83:1467-1473; Salmons and Gunzberg (1993) Human Gene Therapy 4:129-141; and Grossman and Wilson (1993) Curr. Opin. in Genetics and Devel. 3:110-114.

Adenoviruses may also be used effectively in gene therapy. Adenoviruses are especially attractive vehicles for delivering genes to respiratory epithelia. Adenoviruses naturally infect respiratory epithelia where they cause mild disease. Other targets for adenovirus-based delivery systems are the liver, the central nervous system, endothelial cells, and muscle. Adenoviruses have the advantage of being capable of infecting non-dividing cells. Kozarsky and Wilson (1993) Current Opinion in Genetics and Development 3:499-503 present a review of adenovirus-based gene therapy. Bout et al. (1994) Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al. (1991) Science 252:431-434; Rosenfeld et al. (1992) Cell 68:143-155; Mastrangeli et al. (1993) J. Clin. Invest. 91:225-234; PCT Publication WO94/12649; and Wang, et al. (1995) Gene Therapy 2:775-783. Adeno-associated virus (AAV) has also been proposed for use in gene therapy (Walsh et al. (1993) Proc. Soc. Exp. Biol. Med. 204:289-300; U.S. Pat. No. 5,436,146).

Another suitable approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene and such cells are delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr (1993) Meth. Enzymol. 217:599-618; Cohen et al. (1993) Meth. Enzymol. 217:618-644; Cline (1985) Pharmac. Ther. 29:69-92) and may be used in accordance with the present invention, provided that the necessary developmental and physiological functions of the recipient cells are not disrupted. The technique provides for the stable transfer of the nucleic acid to the cell, so that the nucleic acid is expressible by the cell and preferably heritable and expressible by its cell progeny.

The resulting recombinant cells can be delivered to a subject by various methods known in the art. In a preferred embodiment, epithelial cells are injected, e.g., subcutaneously. In another embodiment, recombinant skin cells may be applied as a skin graft onto the subject; recombinant blood cells (e.g., hematopoietic stem or progenitor cells) are preferably administered intravenously. The number of cells envisioned for use depends on the desired effect, the condition of the subject, etc., and can be determined by one skilled in the art.

Cells into which a nucleic acid can be introduced for purposes of gene therapy encompass any desired, available cell type, and include but are not limited to neuronal cells, glial cells (e.g., oligodendrocytes or astrocytes), epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood or fetal liver. In a preferred embodiment, the cell used for gene therapy is autologous to the subject that is treated.

In another embodiment, the nucleic acid to be introduced for purposes of gene therapy may comprise an inducible promoter operably linked to the coding region, such that expression of the nucleic acid is controllable by adjusting the concentration of an appropriate inducer of transcription.

Direct injection of a DNA encoding a peptide or protein capable of binding to and/or modulating an activity of hRif1 and/or ATM kinase may also be performed according to, for example, the techniques described in U.S. Pat. No. 5,589,466. These techniques involve the injection of "naked DNA", i.e., isolated DNA molecules in the absence of liposomes, cells, or any other material besides a suitable carrier. The injection of DNA encoding a protein and operably linked to a suitable promoter results in the production of the protein in cells near the site of injection.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

EXAMPLE I

Methods and Materials

Cell culture conditions: IMR90 primary human fibroblasts (ATCC, early passage), AG02496 and AG04405 primary AT fibroblasts (Cornell Cell Repository), GM847 (ATCC), hTERT/BJ, SV40-transformed NBS-1 LB1 cells [Zdziencka. (1999) Biochimie 81, 107-116; a gift from Margaret Zdziencka), and ATLD-3 and ATLD-4 cells [Stewart et al. (1999) Cell 99, 577-587; a gift from John Petrini] were grown in DMEM, 15% fetal bovine serum. HeLa cells are grown in DMEM, 10% bovine calf serum. U2OS cells (ATCC) were grown in McCoy's modified medium with 10% fetal bovine serum. HCC1 937 cells (ATCC) and HCT-15 cells (ATCC) were grown in RPMI media with 10% fetal bovine serum and 1 mM sodium pyruvate. All media were supplemented with 2 mM L-glutamine, 0.1 mM non-essential amino acids, 100 units of penicillin per ml and 0.1 µg of streptomycin per ml.

For IR treatment, cells were exposed to gamma($\lambda$)-irradiation using a $Cs^{137}$ source at a rate of 7.7 Gray/min in 6 cm dishes. For UV radiation, cells were washed with PBS and exposed to 25 $J/m^2$ UV (265 nm) radiation in a Stratalinker (Stratagene) without a lid. After UV radiation, cells were incubated in media until harvest. For immunoblotting as described in FIG. 2B, cells were harvested 1 hr post-UV. MMS and etoposide (0.01% w/v and 50 µg/ml, respectively) were added to the media and cells were incubated for 1 hr before harvesting. Caffeine (20 mM in $H_2O$) and wortmannin (100 µM, in DMSO) were added to the media 2 hrs and 1 hr before irradiation, respectively, and fixed 30 minutes post-irradiation. Specifically, IMR90 (passage 14) cells were treated with caffeine 2 hr prior to 1 Gy IR and fixed 30 minutes post-IR and U2OS cells were treated with the indicated concentrations of wortmannin 1 hr prior to 5 Gy IR and fixed 30 minutes post-IR.

Antibodies, IF, and Western blotting: Antibodies 1025 and 1060 were affinity purified from rabbit serum immunized with keyhole limpet haemocyanin-conjugated Rif1 peptides [NSESDSSEAKEEG SRKKRSGKWKNK (SEQ ID NO: 3) and EEGIIDANKTETNTEYSKSEEKLDN (SEQ ID NO: 4); both with an added C-terminal Cys residue]. These Rif1 peptides were chosen on the basis of antigenic index analysis of the full length hRif1 protein. Serum obtained from mice immunized with the KLH-conjugated 1060 peptide was also used but without affinity purification. Antibodies 1066 and 1067 are crude serum from rabbits immunized with a GST fusion protein consisting of GST fused to amino acid residues 906-1326 of Rif1. Pre-immune serum (1060 PI) was used as a control for some experiments.

For other proteins, the following antibodies were used: TRF1, 371 [van Steensel and de Lange. (1997) Nature 385, 740-743]; TRF2, 647 [Smogorzewska et al. (2000) Mol Cell Biol 20, 1659-1668] or a monoclonal from Upstate; ATM 2C1 (GeneTex); phospho-ATM Ser 1981 [Bakkenist and Kastan, 2003, supra; a gift from Mike Kastan]; ATRIP-N [Cortez et al., 2001, supra; a gift from Steve Elledge); BRCA1 Ab-1 (Oncogene Research Products); phospho-BRCA1 Ser1524 (Oncogene Research Products); phospho-Chk1 Ser317 (Cell Signaling); phospho-Chk1 Ser345 (Cell Signalling); β-H2AX Ser139 (Upstate); Nbs1 [Maser et al. (2001) Nat Genet 27, 417-421; a gift from John Petrini]; phospho-p53 Ser15 (Cell Signaling); anti-p53 (DO-1; Santa Cruz); anti-p21 (F-5; Santa Cruz); phospho-Rad17 Ser 645 (Cell Signaling); 53BP1 [Ouellette et al. (2000) Hum Mol Genet 9, 403-411]; a gift from Thanos Halazonetis) or Novus Biologicals 100-305A; anti phospho Chk2 (Cell Signaling #2661); α-tubulin clone B-5-1-2 (Sigma); lamin A/C Santa Cruz (sc-7292); and λ-tubulin clone GTU-88 (Sigma).

To prepare whole cell lysates, cells were trypsinized, washed once with media, washed once with cold PBS, counted and resuspended at $1 \times 10^4$ cells/µl Laemmli buffer (4×), boiled for 10 minutes and then sheared through a 28 gauge insulin syringe. To prepare buffer C extract, cells were trypsinized, washed once with media, twice with ice-cold PBS, and incubated in buffer C [van Steensel et al. (1998) Cell 92, 401-413] on ice for 30 minutes. After centrifugation at 4° C. for 10 minutes at 14,000 rpm, the supernatant was collected and the Bradford assay was used to determine protein concentration. The extract was then combined with Laemmli buffer and boiled for 10 minutes. Protein samples were separated by SDS-PAGE and blotted to either nitrocellulose or PVDF (for ATM) membranes. Membranes were blocked in 10% non-fat powdered milk/0.5% Tween-20 in PBS for 30 min at room temperature and incubated with primary antibodies in 0.1% non-fat powdered milk/0.1% Tween-20 in PBS (IB) at 4° C. overnight. Membranes were washed three times in IB, incubated with secondary antibody in IB for 40 minutes at room temperature, washed three times with IB, twice with PBS, and once with $H_2O$. ECL (Amersham) was applied and membranes were exposed to film.

To stain cells for immunofluorescence, tissue culture cells plated on dishes with coverslips were washed twice with PBS, fixed with 2% paraformaldehyde in PBS (stored at −20° C.) for 10 minutes at room temperature (RT), washed twice with PBS and permeabilized with 0.5% NP-40 in PBS for 10 minutes at RT and washed three times with PBS. Cells were processed immediately or stored at 4° C. wrapped in PBS with sodium azide. Coverslips were placed on parafilm in a humidified tray and blocked with PBG (0.2% (w/v) cold water fish gelatin (Sigma), 0.5% (w/v) BSA (Sigma) in PBS (stored at −20° C.) for 30 minutes at RT. Cells were then incubated with primary antibody diluted in PBG for 3 hours at RT, washed three times with PBG for 5 minutes at RT, incubated with secondary antibody diluted 1:100 in PBG for 40 minutes at RT, washed three times with PBG for 5 minutes at RT (with the last wash containing DAPI (p-phenylene diamine (Sigma)). Coverslips were then washed twice with PBS and mounted on glass slides in mounting media and sealed with nail polish.

In some cases, cells were pre-extracted with Triton X-100 or treated with a cytoskeleton pre-extraction protocol [Mirzoeva and Petrini. (2001) Mol Cell Biol 21, 281-288]. For Triton X-100 extraction, cells grown on coverslips were rinsed twice with PBS and extracted with Triton X-100 extraction buffer (0.5% Triton X-100, 20 mM HEPES-KOH pH7.9, 50 mM NaCl, 3 mM MgCl2, and 300 mM sucrose) at either RT or 4° C. for 1-5 minutes. Cells were then rinsed twice with PBS and fixed in 3% paraformaldehyde/2% sucrose for 10 minutes at RT, washed twice with PBS, permeabilized in Triton X-100 buffer for 10 minutes at RT, rinsed twice with PBS and stored in PBS with sodium azide. Detection of Telomere dysfunction Induced Foci (TIFs) was performed as described in Takai et al. [(2003) Curr Biol 13, 1540-1556].

RNAi:

The following sequences were used as Rif1 siRNAs:

1, AACAGACAAGAAAUAGCACCUAdTdT (SEQ ID NO: 5);

2, AAUGAGACUUACGUGUUAAAdTdT (SEQ ID NO: 6);
3, AAGAGAAACCAGGUUCUGAAGdTdT (SEQ ID NO: 7);
4, AAGAAUGAGCCCCUAGGGAAAdTdT (SEQ ID NO: 8);
5, AAGAGGAAAAGUCUACUGACUdTdT (SEQ ID NO: 9); and
6, AAGAGCAUCUCAGGGUUUGCUdTdT (SEQ ID NO: 10);

53BP1 siRNAs 1 and 2 [Wang et al. (2002) Science 298, 1435-1438]; ATRIP siRNAs 1 and 2 [Cortez et al., 2001, supra]; BRCA1 [Ganesan et al. (2002) Cell 111, 393-405]; GFP [Novina et al. (2002) Nat Med 8, 681-686]; lamin A/C and luciferase GL2 [Elbashir et al. (2001) Nature 411, 494-498]; and scrambled (Dharmacon, Scramble I duplex) were used. All siRNAs were obtained from Dharmacon. HeLa, U2OS, or NBS1-LB cells were transfected using Oligofectamine™ (Invitrogen) according to the manufacturer's instructions. Briefly, $1.0 \times 10^5$ of HeLa or $0.8 \times 10^5$ of U2OS or NBS1-LB1 cells per well of a 6-well plate were plated 18-24 hours prior to transfection. Transfections were done twice within a 24 hour interval. Cells were processed 48-72 hr after the first transfection as indicated. As a control, cells were either mock treated or treated with lamin, GFP, scramble I, or luciferase siRNAs.

Clonogenic survival assay: Cells transfected with Rif1 and control siRNAs were harvested and counted in parallel 72 hr after transfection. The cells diluted to the same cell density ($5 \times 10^4$ cells/ml), irradiated, and subsequently plated in triplicate at a range of cell densities. After 10 to 14 days, plates were gently washed with PBS and stained with 50% MeOH/7% glacial acetic acid/43% $H_2O$/0.1% Coomassie Brilliant Blue G for 10 minutes, rinsed with water and air-dried. Colonies were counted for the various treatments on plates with similar numbers of colonies.

Radio-resistant DNA synthesis assay: Inhibition of DNA synthesis after ionizing radiation was assessed on cells treated with siRNAs as previously described [Lim et al., (2000) supra]. Briefly, 4 hours after the second siRNA transfection, cells were placed into DMEM containing 10% FCS and 10 nCi of [methyl/-$^{14}$C]-Thymidine (Amersham Biosciences) per ml, and incubated for 24 hours (HeLa and NBS1-LBI) or 48 hours (AG04405 and IMR90). Medium containing [methy/-$^{14}$C]-Thymidine was then replaced with normal DMEM medium and the cells were incubated for another 24 hours. Cells were subsequently irradiated with either 0 or 10 Gy from a $^{137}$Cs source (dose rate: 3 Gy per min), and incubated for 30 minutes at 37° C. and then pulse-labeled with 2.5 mCi of [methyl-$^3$H]Thymidine (Amersham Biosciences) per ml for 20 minutes at 37° C. After the labeling, cells were rinsed twice with DMEM containing 2.5 mM unlabeled thymidine and collected by trypsinization. The cells were transferred to GF/C filters (Whatman) and washed with 10% trichloroacetic acid. The filters were then rinsed with 100% ethanol, air-dried and the amount of radioactivity was assayed in a liquid scintillation counter. The resulting ratios of $^3$H counts/min to $^{14}$C counts/min ($^3$H/$^{14}$C ratio) were corrected to account for counts resulting from channel crossover. DNA synthesis ratio after exposure to ionizing radiation was calculated as [($^3$H/$^{14}$C ratio in irradiated cells)/($^3$H/$^{14}$C ratio in unirradiated cells)].

G2/M checkpoint assay: G2/M checkpoint assay was performed as described (Xu et al., 2002b). Briefly, HeLa and U2OS cells were transfected with control or Rif1 siRNA twice as described above. Cells were replated at a concentration of $4 \times 10^5$ cells/6 cm dish, 24 hours after the second transfection and were cultured another 24 hours. Cells were treated with 0, 2, or 10 Gy IR and incubated for 1 hr at 37° C. Cells were harvested, washed with PBS and fixed in 70% ethanol. After fixation, cells were resuspended in PBS containing 0.1% Triton-X and 0.5% BSA and stained with anti-phospho-Histone H3 (Ser10) antibody (Upstate) and propidium iodide and analyzed by FACS.

RESULTS

Identification and detection of human Rif1

Figure 8A:
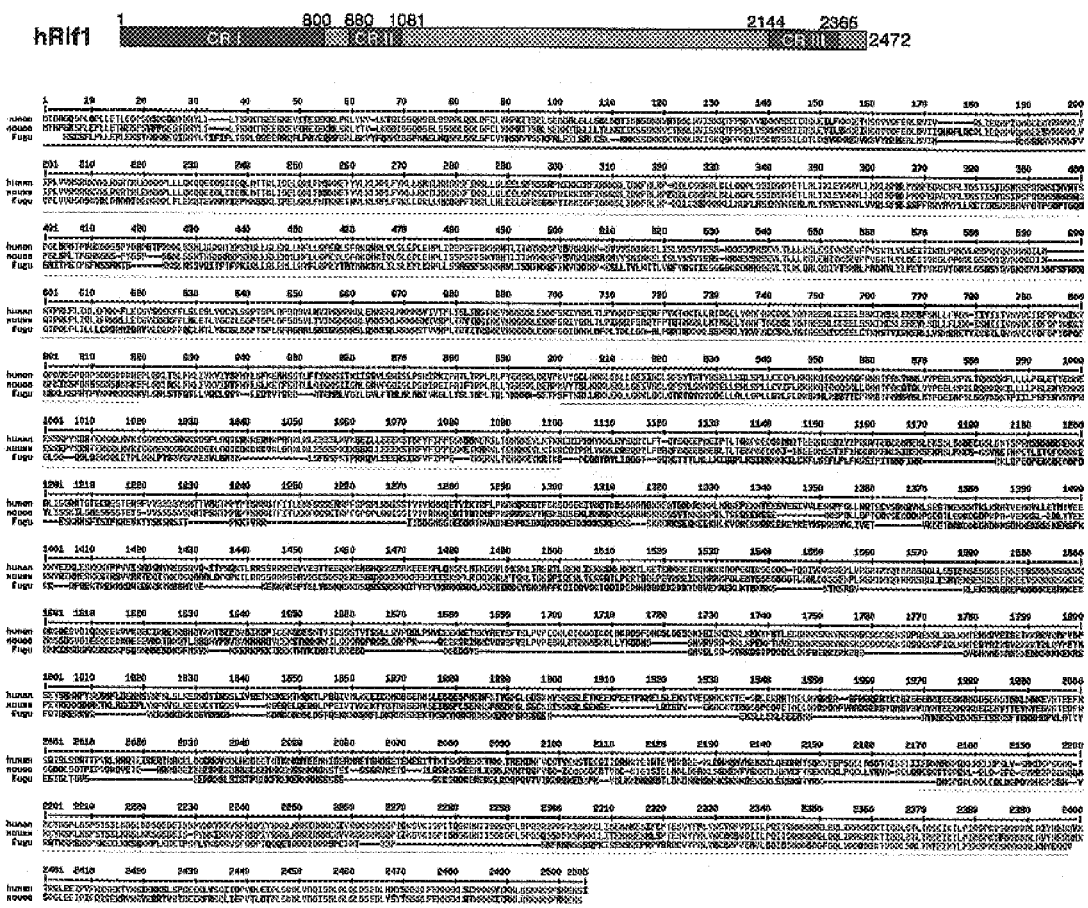

Human Rif1 was identified in Genbank based on sequence similarity to the Rif1 genes of Schizosaccharomyces pombe (S. pombe) and Saccharomyces cerevisiae (S. cerevisiae) (BLAST search; P =$9 \times 10^{-5}$) [Hardy et al. (1992) supra; Kanoh and Ishikawa. (2001) supra] (Genbank accession for mouse Rif1 AY585206; human Rif1 pending; part of the human Rif1 gene is noted in Unigene locus FLJ10599). The human Rif1 sequence predicts a 2472 amino acid protein with a pI of 5.4 and a predicted MW of 274 kDa. Alignment of human, mouse, and fugu Rif1 ORFs revealed three conserved regions, CR I-III (FIG. 1A and FIG. 8A). Comparison to S. cerevisiae Rif1 indicated that 20-25% of the amino acids in CRI-III are conserved (FIG. 8B). The most notable feature of the mammalian Rif1 proteins is that the N-terminal 340 amino acids most likely have the shape of (apparently 8) helical repeats of HEAT- or ARMADILLO-type and it is possible that the HEAT/ARMADILLO repeat structure continues throughout the remaining hydrophobic N-terminal half of the protein (see Example II for additional details). The helical HEAT/ARMADILLO folds typically occur in long arrays, creating an extended curved protein or RNA interaction surface suggesting that Rif1 may have a scaffolding function.

Polyclonal rabbit and mouse antisera were raised against two different Rif1 peptides and a protein fragment fused to GST (FIG. 1A). All antibodies react with the same large (>250 kDa) polypeptide in Western blots of human cell lines (FIG. 1B). The abundance of the polypeptide recognized by the antibodies is diminished in cells treated with siRNAs corresponding to Rif1, thereby confirming that the large, reactive polypeptide is encoded by the Rif1 gene and establishing the specificity of the sera. Human Rif1 is detectable in different human cell lines and strains (e.g. IMR90, BJ, W138, GM847, VA-13, HeLa, U2OS, HCT15, HT1080) and Rif1 mRNA is present in a wide variety of tissues, suggesting ubiquitous expression. HeLa cells in G1, S, or G2/M phase obtained by centrifugal elutriation contain similar amounts of Rif 1.

Indirect immunofluorescence (IF) with Rif1 antibodies reveals a nuclear staining pattern with most of the signal distributed in a diffuse pattern throughout the nucleus of interphase cells. Dual IF with markers for telomeric sites, including TRF1, TRF2, Rap1, and TIN2, does not reveal accumulation of Rif1 on chromosome ends. Telomeric accumulation is also not observed in several other cell types, using a variety of methods for cell fixation (paraformaldehyde and methanol), and after extraction of soluble nucleoplasmic proteins with Triton-X-100. Furthermore, Rif1 is not recovered in immunoprecipitates of the telomeric proteins TRF1, TRF2, and Rap1 and chromatin immunoprecipitations with Rif1 antiserum do not bring down telomeric DNA.

Telomeres protect natural chromosome ends from being recognized as sites of DNA damage. The main protective protein at human telomeres is TRF2 [reviewed in de Lange. (2002) supra]. Inhibition of TRF2 with a dominant negative allele results in telomere dysfunction [Karlseder et al. (1999) Science 283, 1321-1325; van Steensel and de Lange. (1997)

Nature 385, 740-743]. Such uncapped telomeres are recognized as sites of DNA damage, leading to the accumulation of DNA damage response factors, such as Nbs1, 53BP1, ATM, Rad17, and β-H2AX at chromosome ends [d'Adda di Fagagna et al. (2003) Nat Rev Cancer 3, 23-34; Takai et al. (2003) Curr Biol 13, 1540-1556]. The foci formed at uncapped telomeres resemble DNA damage response foci and are referred to as Telomere Dysfunction Induced Foci or TIFs. IF revealed that Rif1 co-localizes with some of the telomeres in cells infected with a dominant negative allele of TRF2, suggesting that Rif1 is a component of TIFs.

Rif1 is also associated with unusual telomeric DNA containing structures present in ALT (Alternative Lengthening of Telomeres) cell lines, which maintain telomeric DNA in the absence of telomerase [reviewed in Henson et al. (2002) Oncogene 21, 598-610]. A subset of the cells in ALT cultures contain large foci of telomeric DNA associated with telomeric proteins as well as a number of protein factors that are not normally observed at telomeres, including the PML protein, Rad52, and RPA [Yeager et al. (1999) Cancer Res 59, 4175-4179]. These structures are referred to as ALT associated PML Bodies, or APBs. IF analysis showed that Rif1 is detectable in most of the APBs in the ALT cell line GM847.

Rif1 Response to Double-Strand Breaks

The association of Rif1 with dysfunctional telomeres and with the APBs of ALT cells suggested a role for Rif1 in the DNA damage response. To test this, cells were irradiated and the nuclear Rif1 pattern was ascertained by IF. After IR, all cells exhibit discrete Rif1 foci that are detectable with all Rif1 antibodies. This response is rapid, occurs within 5 minutes, and persists for many hours. At 8 hours after irradiation, the number of Rif1 foci per cell diminishes. As little as 0.5 Gy induces Rif1 foci and the number of foci increases with higher doses, reaching a plateau between 1-10 Gy. The foci co-localize with the DNA damage response factor 53BP1 [Schultz et al. (2000) J Cell Biol 151, 1381-1390], consistent with the idea that Rif1 re-localizes to sites of DNA damage. Rif1 also forms foci after treatment with radiomimetic drugs (such as MMS and etoposide) and prolonged incubation in hydroxyurea, which represent conditions capable of leading to formation of DSBs. See FIGS. 11A-F.

In addition to treatments that induce DSBs, DNA damage created by UV light leads to a Rif1 response. Unlike the response to IR, which occurs in all cells, UV-induced Rif1 foci only form in a subset of the cells (~20-30%). To test whether progression through S-phase is required for this response, cells are treated with aphidicolin after the UV irradiation. Aphidicolin treated cells fail to form Rif1 foci after UV, whereas 53BP1 foci are still detectable. This result indicates that the Rif1 response to UV light depends on progression through S-phase which may convert the primary UV damage into DSBs. Collectively, these findings suggest that Rif1 responds primarily to DSBs. See FIGS. 11A-F.

In addition to 53BP1, the IR-induced Rif1 foci co-localized with several other DNA damage response factors, including β-H2AX, Chk1 phosphorylated on S317, activated ATM (phosphorylated on S1981), Rad17 phosphorylated on S645, Mre11, and BRCA1. In contrast, TRF1 and other telomeric proteins do not localize to sites of DNA damage, as previously described [Zhu et al. (2000). Nat Genet 25, 347-352]. Rif1, therefore, behaves similarly to previously described factors that accumulate at sites of DSBs.

Rif1 Controlled by ATM not ATR

Figure 2B:
Figures 12A, 12B:
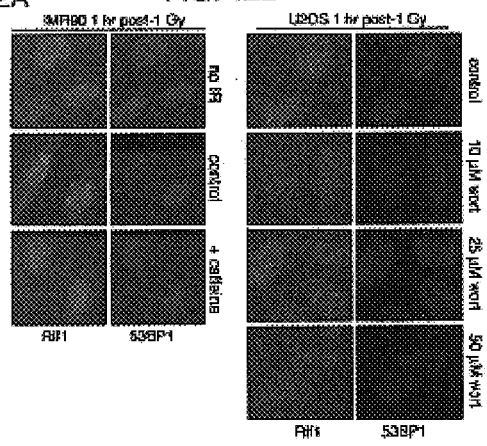
FIGS. 12A-E show photomicrographs depicting immunofluorescence staining.
Figure 12C:
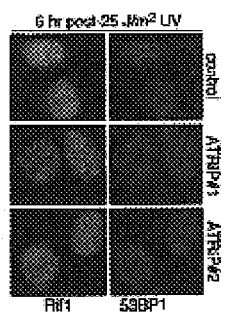
Figure 12D:
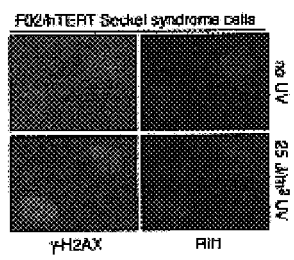

The induction of Rif1 foci is severely reduced when cells are treated with inhibitors of the PI3 kinase-related family of kinases (PIKKs), which includes the ATM and ATR kinases. As shown by IF analysis, treatment of IMR90 cells with caffeine almost completely abolishes the Rif1 response to DNA damage (FIG. 12A). Rif1 foci are also repressed by treatment of IMR90 cells or U2OS cells with wortmannin (FIG. 12B). In order to test the dependence of Rif1 on the ATR kinase, the response of Rif1 to UV was examined in cells treated with siRNAs to ATRIP, an essential partner for ATR [Cortez et al. (2001) supra]. As previously reported, two different ATRIP siRNAs result in nearly complete depletion of the ATRIP protein (FIG. 2A). Furthermore, cells treated with ATRIP siRNAs show a strong reduction in the phosphorylation of Chk1 and Rad17 in response to UV, indicating that ATR signaling is inhibited (FIG. 2B). Despite the diminished ATR signaling, UV treatment continues to induce Rif1 foci in cells transfected with ATRIP siRNA (FIG. 12C). The Rif1 response to UV was also tested in cells derived from a Seckel syndrome patient with a severely reduced ATR protein level due to a splicing defect [O'Driscoll et al. (2003) Nat Genet 33, 497-501]. See FIG. 12D. These cells still exhibit Rif1 foci after UV, verifying that the Rif1 response does not require fully functional ATR.

Figure 12E:
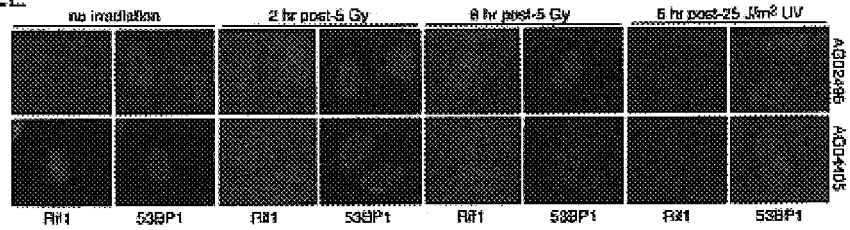

To test the dependence of Rif1 on ATM, fibroblasts from two unrelated AT patients lacking the ATM kinase, as verified by immunoblotting, were used. When these cells are treated with IR, no Rif1 foci are observed (FIG. 12E), even though the cells express normal amounts of Rif1 protein. Even prolonged (8 hr) incubation after 5 Gy (FIG. 12E) or treatment with 20 Gy fails to induce Rif1 foci. By contrast, IR treated AT cells formed 53BP1 foci (FIG. 12E), albeit at diminished levels as previously noted by Rappold et al. [(2001) J Cell Biol 153, 613-620]. AT cells also fail to form Rif1 foci after UV treatment, whereas 53BP1 foci still form (FIG. 12E). These data indicate that the ability of Rif 1 to form foci after the induction of DSBs requires the function of ATM but not ATR.

Dependence of Rif1 on 53BP1

Several components of the ATM signaling pathway were tested for their effect on the Rif1 response to DSBs. Although Chk2 is a target of ATM [Matsuoka et al. (1998) Science 282, 1893-1897], its activity is not required for Rif1 regulation: HCT15 cells, lacking functional Chk2, still display Rif1 foci after IR. The role of the Mre11 complex, which has been shown to contribute to the ATM pathway both upstream and downstream of ATM [Carney et al. (1998) Cell 93, 477-486; Carson et al. (2003). EMBO J 22, 6610-6620; Gatei et al. (2000) supra; Lim et al. (2000) supra; Stewart et al. (1999) supra; Uziel et al. (2003) EMBO J 22, 5612-5621; Wu et al. (2000) supra; Zhao et al. (2000) supra; reviewed in Petrini and Stracker. (2003) Trends Cell Biol 13, 458-462], was also investigated. NBS1-LB1 cells derived from a Nijmegen breakage syndrome patient with a hypomorphic mutation in the Nbs1 component of the Mre11 complex [Kraakman-van der Zwet et al. (1999). Mutat Res 434, 17-27] do not display an obvious defect in Rif1 focus formation. Similarly, two Mre11 mutant cell lines (ATLD3 and 4; [Stewart et al. (1999) supra] formed Rif1 foci after IR. Finally, HCC1937 cells which lack functional BRCA1 retain the ability to form Rif1 foci [Tomlinson et al (1998) Cancer Res 58, 3237-3242]. Treatment of HeLa cells with a BRCA1 siRNA [Ganesan et al. (2002) Cell 111, 393-405] also do not affect the Rif1 response.

Figure 3:
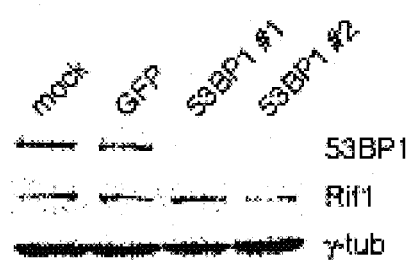
FIG. 3 shows immunoblotting analysis of the effect of 53BP1 siRNAs on HeLa cells transfected twice with the indicated siRNAs and analyzed by immunoblotting 72 hr after the first transfection for expression of the indicated proteins (Rif1 was detected with mouse 1060).

In contrast, inhibition of 53BP1 completely abolishes the Rif1 response to DNA damage. Reduction in 53BP1 expression is achieved with two different siRNAs, as demonstrated by immunoblotting [Wang et al. (2002) Science 298, 1435-1438; FIG. 3A). Rif1 expression is not affected by these siRNAs (FIG. 3A). As expected, the induction of 53BP1 foci by IR is strongly reduced in cells treated with the 53BP1 siRNAs. Cells without 53BP1 foci also lack Rif1 foci, indicating that a functional relationship between these factors exists. Normal Rif1 foci occur in the few nontransfected cells in the culture, providing an internal experimental control. Thus, Rif1 appears to be regulated by two components of the ATM pathway, 53BP1 and ATM. As 53BP1 forms foci in AT cells, but Rif1 does not, it appears that Rif1 requires an ATM regulated event in addition to normal levels of 53BP1.

Figure 4A:
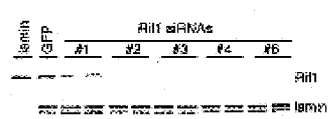
FIGS. 4A-H show (A) immunoblotting analysis of Rif1 siRNAs in HeLa cells transfected twice with the indicated siRNAs and analyzed by immunoblotting 72 hr after the first transfection for expression of the indicated proteins (Rif1 was detected with Ab 1060); (B) photographs of Coomassie stained sample plates showing cells ($10^4$ cells plated per 6 cm² dish) treated with Rif1 siRNA as in (A) and irradiated with the indicated dose of IR 72 hr after transfection; (C) line graphs depicting clonogenic survival of cells treated, plated and stained as in (B): error bars indicate standard deviation of triplicate experiments, dashed lines indicate the least squared linear regression through either mock and scrambled I (black) or two independent Rif1 siRNAs (#2 and #4; red) data points; (D) line graphs depicting clonogenic survival after IR in U2OS cells; (E) line graphs depicting clonogenic survival after mitomycin C treatment in HeLa cells: HeLa cells treated with siRNA as in (A), brought to the same concentration and plated in triplicate at multiple concentrations at 72 hr after transfection and treated with indicated concentration of MMC for 4 hours; (F) scatter plot analysis of DNA synthesis ratios depicting effect of Rif1 siRNAs on the intra S-phase checkpoint in cells treated with siRNA as in (A) and also treated with either 0 Gy or 10 Gy IR at 72 hr post transfection. The DNA synthesis ratio was normalized to untreated cultures; (G) scatter plot analysis of DNA synthesis ratios depicting NBS1-LB1 cells stably infected with control vector or wild type Nbs1 retroviruses treated as in (F); and (H) immunoblot analysis of NBS1-LBI cells treated with Rif1 siRNA.
Figure 4B:
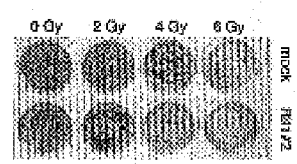

Rif1 deficiency Results in Radiosensitivity and an Intra-S Phase Checkpoint Defect To study the consequences of diminished Rif1 function, several siRNAs to Rif1 were used that potently reduce Rif1 protein levels (FIG. 4A) and block the formation of Rif1 foci after IR. Temporary knock-down of Rif1 expression does not result in phenotypes associated with telomere uncapping (e.g., telomere fusions), consistent with the lack of Rif1 accumulation at functional telomeres.

Figure 5A:
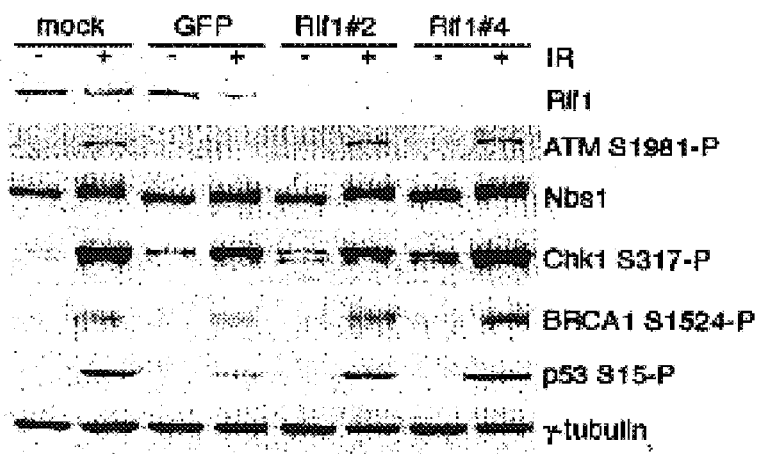
FIGS. 5A-B show immunoblotting analysis of (A) whole cell lysates prepared from U2OS cells transfected twice with the indicated siRNAs and treated with either 0 Gy or 10 Gy IR 72 hr after the first transfection probed with mouse 1060 antisera and antibodies recognizing ATM-S1981-P, BRCA1-S1524-P, Chk1-S317-P, p53-Ser15-P, Nbs1-S343-P, and anti-tubulin blotting (used as a loading control); and (B) cell lysates prepared from Nbs1-LB cells infected with Nbs1 (Nbs1) or the retroviral vector alone (pLPC) treated with the indicated siRNAs, irradiated 72 hours later with 9 Gy, and harvested 30 min post-IR. The scheme summarizes a proposed reciprocal relationship of Nbs1, ATM, and 53BP1 with respect to Chk2T68 phosphorylation.

The effect of Rif1 siRNAs on ATM activation was investigated by immunoblotting to detect phosphorylated ATM targets. The activating auto-phosphorylation of ATM at serine 1981 is not affected by Rif1 siRNA treatment and the phosphorylation of Nbs1, Chk1, BRCA1, and p53 occurs normally in irradiated cells with reduced Rif1 (FIG. 5A). Rif1 inhibition also does not affect IR-induced focus formation by 53BP1. These data are consistent with Rif1 acting downstream of ATM and 53BP1.

Figure 4C:
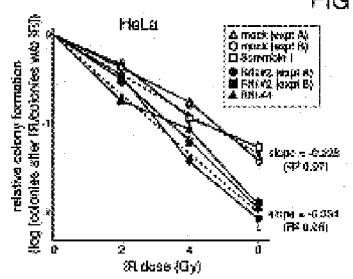
Figure 4D:
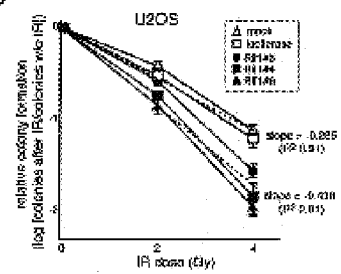
Figure 4E:
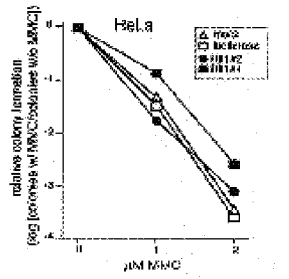

Since deficiency in ATM or 53BP1 results in increased radiosensitivity, the potential for a similar phenotype arising from Rif1 inhibition was explored [Taylor et al. (1975) Nature 258, 427-429; Ward et al. (2003) Mol Cell Biol 23, 2556-2563. Three different tumor cell lines (HeLa, U2OS, A549) were treated with several different Rif1 siRNAs and tested for clonogenic survival after ionizing radiation (FIG. 4C-E). Control cultures were either mock treated or treated with a control siRNA. In each cell line, Rif1 siRNAs lead to hypersensitivity to IR. For instance, after radiation with 6 Gy, Rif1 knockdown HeLa cells exhibit a 4.3-fold reduction in clonogenic survival (P<0.0001, Student's t test). This effect is comparable to the radiosensitivity associated with siRNA mediated knockdown of BRCA1 [Ganesan et al. (2002) supra] or inhibition of ATM and SMC1 function with mutated alleles [Kim et al. (2002) Genes Dev 16, 560-570], but modest compared to the radiosensitivity of AT cells which typically display 10-fold lower survival rates. The importance of Rif1 for survival after DNA damage may, however, be underestimated in this model system.

Figure 4F:
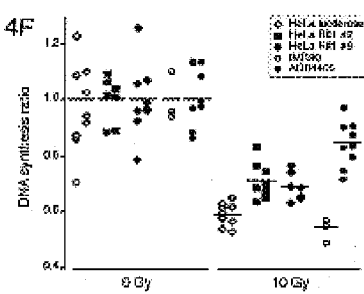

Hypersensitivity to IR is also found under certain circumstances when the Fanconi anemia (FA) pathway is compromised [D'Andrea and Grompe. (2003) supra] and the FA protein FANCD2 is a target of ATM [Taniguchi et al. (2002) Cell 109, 459-472]. In order to determine whether Rif1 contributes to the FA pathway, the consequences of Rif1 siRNA treatment on hypersensitivity to the cross-linking agent MMC were determined. Hypersensitivity to MMC is a useful cellular assay in this context because it is a hallmark of FA cells, but not observed in AT cells [Jaspers et al. (1982) Cancer Res 42, 335-341]. The results reveal that Rif1 siRNAs do not diminish the ability of cells to survive in the presence of MMC (FIG. 4F), arguing against a role for Rif1 in the FA pathway and demonstrating the specificity of the radiosensitive phenotype of Rif1 inhibition.

Figure 4G:
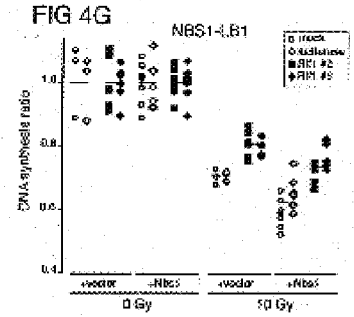

A second consequence of ATM or 53BP1 deficiency is a defect in the intra-S-phase checkpoint [reviewed in Osborn et al. (2002) Trends Cell Biol 12, 509-516]. Inability to repress DNA replication after ionizing radiation, results in radioresistant DNA synthesis (RDS). Rif1 depletion also leads to a defect in the intra S-phase checkpoint as evidenced by RDS (FIG. 4G and Table 1). In HeLa cells, knockdown of Rif1 with two siRNAs leads to a partial RDS phenotype when compared to cells treated with luciferase siRNA or mock treated cells (n>23; p=0.0014; Scheffe's test; Table 1). The RDS defect after Rif1 knockdown was, however, significantly less prominent than the phenotype of AT cells (p=0.0007; Scheffe's test) (FIG. 4G and Table 1), suggesting that there is a second, Rif1-independent pathway.

Table 1 shows results of Rif1 siRNA treatment of HeLa cells: RDS values and statistics

| Group | cells | siRNA | n | RDS values Average (S.D.) |
|---|---|---|---|---|
| 1 | HeLa | mock + luc | 29 | 0.627 (0.079) |
| 2 | HeLa | Rif1#2 + #6 | 23 | 0.717 (0.076) |
| 3 | IMR90 | none | 4 | 0.551 (0.040) |
| 4 | AG04405 | none | 9 | 0.850 (0.083) |

| Comparison | Statistics cells and siRNAs | p value |
|---|---|---|
| 1 versus 2 | HeLa mock + luc v HeLa Rif1#2 + #6 | 0.0014 |
| 3 versus 4 | IMR90 v AG04405 | <0.0001 |
| 4 versus 2 | AG04405 v HeLa Rif1#2 + #6 | 0.0007 |
| 3 versus 1 | IMR90 v HeLa mock + luc | 0.3406 |
| 1 versus 4 | HeLa mock + luc v AG04405 | <0.0001 |
| 3 versus 2 | IMR90 v HeLa Rif1#2 + #6 | 0.0027 | p value is determined using Scheffe's test

Figure 4H:
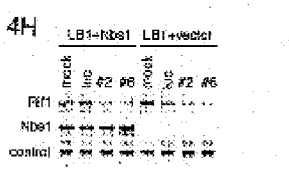

Recent data has indicated that the intra-S phase checkpoint is due to at least two independent pathways, both regulated by ATM. One of these is represented by Nbs1, which probably acts in conjunction with BRCA1, SMC1, and FANCD2 [Falck et al. (2002) supra; Kim et al. (2002) supra; Nakanishi et al. (2002) Nat Cell Biol 4, 913-920; Yazdi et al. (2002) supra]. To determine whether Rif1 acts in this pathway, the RDS phenotype of Rif1 inhibition in NBS1 mutant LB1 cells was evaluated. These cells exhibit the expected effect of Nbs1 deficiency in terms of RDS (FIG. 4H and Table 2) and retroviral expression of wild type Nbs1 in these cells improved the intra-S phase checkpoint (p=0.0074; Scheffe's test) (FIG. 4H-I and Table 2), as previously reported [Zhao et al. (2000) supra]. Inhibition of Rif1 in LB1 cells results in an RDS phenotype (p=0.0017; Scheffe's test; Table 2), regardless of the Nbs1 status (FIG. 4H-I). Moreover, the effects of Rif1 and Nbs1 deficiency are additive (FIG. 4H). Rif1, therefore, acts in an intra-S-phase checkpoint pathway that is separate from the Nbs1 pathway.

Table 2 shows results from Rif1 siRNA treatment of NBS1-LB1 cells: RDS values and statistics

| Group | Cells and retrovirus | siRNA | RDS values Average (S.D.) |
|---|---|---|---|
| 1 | NBS1-LB1 + vector | mock + luc | 0.710 (0.081) |
| 2 | NBS1-LB1 + vector | Rif1#2 + #6 | 0.807 (0.034) |
| 3 | NBS1-LB1 + Nbs1 | mock + luc | 0.628 (0.058) |
| 4 | NBS1-LB1 + Nbs1 | Rif1#2 + #6 | 0.745 (0.048) |

-continued

| Statistics | |
|---|---|
| Comparison | p value (Scheffe's test) |
| 1 versus 2 | 0.0017 |
| 3 versus 4 | <0.0001 |
| 1 versus 3 | 0.0074 |
| 2 versus 4 | 0.0154 |
| 3 versus 2 | <0.0001 |

Figure 5B:
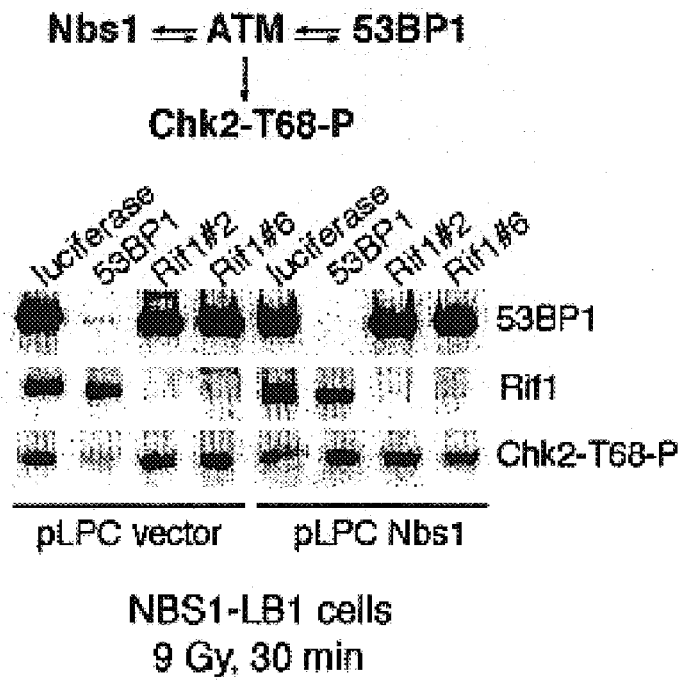

A second pathway involved in the RDS phenotype is defined by the phosphorylation of Cdc25A by Chk2, leading to inactivation of Cdk2 [Falck et al. (2001) supra; Falck et al. (2002) supra]. To assess the effect of Rif1 inhibition on an early step in this pathway, the phosphorylation of Chk2 on T68 after IR, was investigated. As shown herein, Rif1 siRNA treatment does not diminish this phosphorylation event (FIG. 5B). Rif1 also does not affect Chk2 phosphorylation in cells lacking functional Nbs1. In this regard, Rif1 is notably different from 53BP1 which is necessary for Chk2 phosphorylation in the absence of normal Nbs1 function [Mochan et al. (2003) Cancer Res 63, 8586-8591] (FIG. 5B). These data are consistent with the conclusion that Rif1 is not required for Chk2 activation. Similarly, Chk2 is not required for Rif1 focus formation after IR.

Figure 6A:
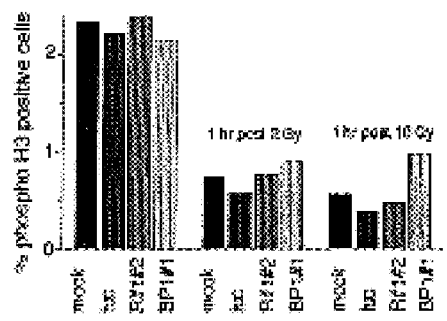
FIGS. 6A-C show (A-B) histograms depicting the percentage of mitotic cells in (A) HeLa and (B) U2OS cell populations transfected with or without siRNA duplex (as indicated) and subsequently treated 48 hr post second transfection with 0, 2, and 10 Gy of y-irradiation and incubated for 1 hr at 37° C. prior to fixation and (C) immunoblotting analysis of cell lysates isolated from U2OS cells treated with mock or Rif1 siRNA and exposed to 10 Gy IR and harvested at 0, 1, 4, and 12 hours after irradiation.
Figure 6B:
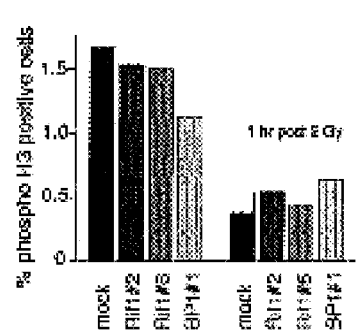
Figure 6C:
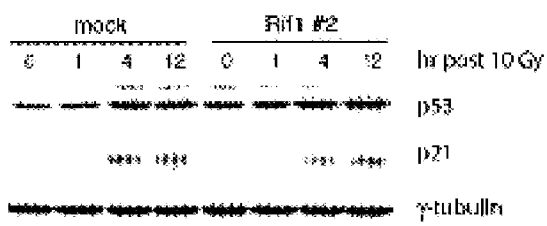

ATM and 53BP1 are also required for the rapid arrest of cells in G2 after IR [DiTullio et al. (2002) supra; Wang et al. (2002) supra; Xu et al. (2002a) Mol Cell Biol 22, 1049-1059]. As a consequence of this checkpoint, cells experiencing damage in G2 will not enter mitosis unless either ATM or 53BP1 is deficient. The G2/M checkpoint was monitored by assessing the propensity of cells to enter mitosis (based on the presence of phosphorylated histone H3) within 1 hour after IR. HeLa and U2OS cells treated with Rif1 siRNA arrest prior to mitosis to the same extent as control cells (FIG. 6A and B), indicating that the ATM regulated G2/M checkpoint does not require full Rif1 function. Finally, it is unlikely that the G1/S checkpoint is affected by Rif1 inhibition since Rif1 siRNAs do not affect Chk2 phosphorylation or p53 activation after IR (FIG. 6C).

Conclusions

Human Rif1 is an ortholog of a fungal protein that associates with telomeres in S. pombe and S. cerevisiae and regulates telomere length. As described herein, human Rif1 does not accumulate at normal functional telomeres. Although a role for human Rif1 at telomeres is not excluded, data presented herein reveal that this factor plays a role in the DNA damage response. Rif1 localizes to sites of DNA damage in an ATM- and 53BP1-dependent manner and functions to regulate the intra-S-phase checkpoint.

Rif1 as a New Component of the ATM Pathway

The ATM pathway is important for the maintenance of genome integrity. Rif1 is regulated by ATM and acts as an ATM effector in the intra-S phase checkpoint (FIG. 7A). Rif1 is unusual in the extent of its dependence on ATM signaling. In ATM deficient cells, Rif1 does not respond to DNA damage, whereas ATR deficiency has no obvious effect. Since Rif1 is the only DNA damage response factor showing this level of ATM dependence with regard to focus formation, Rif1 foci are a useful cell-based indicator of ATM activity. The Rif1 response demonstrated herein confirms earlier reports that UV treatment can activate both ATR and ATM [Hannan et al. (2002) Carcinogenesis 23, 1617-1624; Heinloth et al. (2003) Radiat Res 160, 273-290; Jaspers et al. (1982) supra; Oakley et al. (2001) Mol Biol Cell 12, 1199-1213]. In a subset of UV treated cells, Rif1 forms foci in an ATM-dependent manner. These foci are not formed when S-phase progression is blocked, suggesting that the ATM pathway can be activated when UV-induced lesions are processed during DNA replication. The strict dependence of Rif1 on ATM is also informative in the context of the Rif1 foci formed at a subset of uncapped telomeres. The implication of this finding is that uncapped telomeres can activate ATM, a conclusion consistent with previous data (d'Adda di Fagagna et al. (2003) supra; Karlseder et al. (1999) supra; Takai et al. (2003) supra; Wong et al. (2003) Nature 421, 643-648].

RNAi mediated knockdown showed that partial loss of Rif1 function recapitulates the two phenotypic hallmarks of ATM deficiency: radiosensitivity and RDS. The RDS phenotype of AT cells is due to lack of normal function in at least two parallel pathways. One pathway involves Nbs1, BRCA1, Smc1, and possibly FANCD2. Rif1 is probably not a component of this pathway, however, since the Rif1 RDS phenotype persists in the absence of Nbs1. The second intra-S phase checkpoint pathway is dependent on Chk2. Data presented herein argue against a role for Rif1 in this pathway since Chk2 phosphorylation is not affected by Rif1 status and the Rif1 response is intact in Chk2 cells. Thus, Rif1 may define a third ATM-dependent intra-S phase checkpoint.

Evolutionary Changes in the Telomere Complex

The budding yeast Rif1 gene was identified in a two-hybrid screen executed with Rap1, a protein that binds to the TG1-3 sequences of yeast telomeres. The human ortholog of S. cerevisiae Rap1, identified as a telomeric protein several years ago, is distinct in that it does not bind to telomeric DNA [Li et al. (2000) Cell 101, 471-483]. Instead, human Rap1 is recruited to telomeres by the telomeric binding protein TRF2. This difference led to the proposal that the evolution of budding yeasts included a considerable alteration in the composition of the telomeric protein complex that involved the loss of the TRF1/TRF2-like telomere binding proteins. A vestigial TRF1/TRF2 gene (TBF1) is present in the yeast genome but many of the genes for TRF1 interacting factors such as the tankyrases and TIN2 are not conserved in S. cerevisiae or other budding yeast [reviewed in Smogorzewska and de Lange. (2004) Ann Rev Biochem 73, 177-208]. It was also proposed that the human telomeric complex more closely resembled the ancestral telomere. This view was based on the realization that the fission yeast telomeric protein Taz1p [Cooper et al. (1997) Nature 385, 744-747] is an ortholog of TRF½ [Fairall et al. (2001) Molecular Cell 8, 351-361; Li et al. (2000) supra]. Subsequently, fission yeast Taz1p was shown to recruit Rap1 to telomeres, a situation similar to human telomeres. The recent identification of a TRF½ ortholog in T. brucei (B. Li and G. Cross, pers. comm.) further corroborates the ancient nature of the TRF½ based telomere complex and the relative novelty of the telomeres of budding yeasts.

Telomeres and the DNA Damage Response

It is generally believed that telomeres prevent a DNA damage response at chromosome ends, ensuring that telomeres are not inappropriately processed by DNA repair pathways and guarding against the activation of the ATM and ATR signaling pathways. Telomeres do, however, contain numerous DNA repair factors and associate with components of the damage signaling pathway. Such features have led to the emerging view that telomeres employ factors acting in the DNA damage response for the processing and maintenance of the telomeric complex, but do so in a highly controlled manner such that the detrimental outcomes of these pathways are avoided (see for instance, [de Lange (2004) supra]. This view is supported by evidence showing that the nucleotide excision repair endonuclease ERCC1/XPF and non-homologous end-joining factors are used for the protection of human telomeres [Bailey et al. (1999). Proc Natl Acad Sci U S A 96, 14899-14904; Zhu et al. (2003). Mol Cell 12, 1489-1498]. These same factors have been implicated in the generation of telomere fusions and are, therefore, likely to be controlled by the telomeric complex in its functional state [Smogorzewska et al. (2002). Curr Biol 12, 1635; Zhu et al. (2003) supra].

Rif1 may be an example of a DNA damage response factor that is utilized at telomeres. The data presented herein for human Rif1 suggest that telomere length control in *S. pombe* and *S. cerevisiae* may have a mechanistic link to events taking place when the DNA replication fork encounters a site of DNA damage.

EXAMPLE II

Sequence Analysis Reveals that Human Rif1 is a HEAT/ARMADILLO-Repeat Containing, Macromolecular Scaffold Protein Amino acid compositional bias complicates sequence-analytic dissection of the human Rif1 protein sequence. The N-terminal ~1000 residue stretch is quite hydrophobic (about 50% aliphatic residues, phenylalanine and proline) and is predicted to form stable 3D structures. Indeed, the region comprising the N-terminal 340 amino acids (N-terminal fragment or subdomain) most likely assumes the conformation of eight helical repeats of HEAT- or ARMADILLO-type [Andrade et al. J Mol Biol. (2001) 309:1-18]. This conclusion is corroborated by hits with IMPALA (E=0.0001) [Schaffer et al. Bioinformatics (1999)15:1000-1001], SUPERFAMILY (E=7.5e-09) [Madera et al. Nucleic Acids Res (2004) 32 Database issue:D235-9] and multiple single-repeat hits to the HEAT and ARMADILLO model in the REP database [Andrade et al. (2001) supra]. It is possible that the HEAT/ARMADILLO repeat structure continues throughout the remaining hydrophobic N-terminal subdomain since (i) the predicted secondary structure is mainly helical, (ii) clusters of hydrophobic residues are spaced at distances consistent with the length of one or two HEAT/ARMADILLO repeats and (iii) and there is a single HEAT repeat hit in the homologous region of the apparent *Drosophila melanogaster* homolog (Genbank Accession Number Q9XZ34, residues 587-631).

In contrast, the C-terminal fragment or subdomain (1030-2472) is strongly biased towards polar and even charged residues (20% ST, 18% ED, 13% KR) and text analysis tools such as SEG [Wootton and Federhen. Methods Enzymol (1996) 266:554-571] detect numerous regions with low linguistic complexity. It is, therefore, likely that, except for small segments (especially the final 200 residues), the C-terminal domain has little intrinsic 3D structure-forming potential and represents a highly flexible polypeptide chain.

Whereas the apparent metazoan homologs in mouse (several fragment entries in NR), rat (XP_215736), *Fugu rubripes* (SINFRUP00000157448), *D. melanogaster* (Q9XZ34) and *Anopheles gambiae* (XP_311554) have identical sequence architecture (as far as the possibly incomplete genomic translations enable assessment), the fungal Rif1s represented by the candidate homologues in *S. cerevisiae* (GenBank Accession Number CAA47121) and *S. pombe* (GenBank Accession Number Q96UP3), have an additional polar segment (approximately 100 residues) at the N-terminal side of the apparent HEAT/ARMADILLO repeat region.

With respect to molecular function, sequence-analytic findings suggest that Rif1 s might have scaffolding functions. Macromolecular superhelices formed by helical repeats supply docking sites for globular proteins [Andrade et al. (2001) supra]. In view of its amino acid composition, the unstructured C-terminal domain may comprise recognition motifs for posttranslationally modifying enzymes and/or charged regions for differential protein-protein and/or protein/nucleic acid interactions.

EXAMPLE III hRif1 is a Potential Tumor Suppressor Gene

The present inventors have also discovered that hRif1 may act as a tumor suppressor gene, the loss of which in a cell results in a dramatically increased chance for development of a transformed phenotype. Briefly, in cells comprising a heterozygous hRif1 genotype (i.e., hRif1+/hRif1−), a second hit that results in the loss of the remaining hRif1+ wild type allele strongly predisposes such cells to exhibit phenotypic characteristics of a transformed cell.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid sequence encoding a polypeptide comprising SEQ ID NO: 2, wherein said polypeptide forms foci at sites of DNA damage in cells treated to induce DNA damage, wherein said cells have normal Ataxia Telangiectasia Mutated (ATM) kinase activity.

2. A vector comprising the isolated nucleic acid sequence of claim 1, operably linked to regulatory elements.

3. The vector of claim 2, wherein said vector is an expression vector.

* * * * *

SEQUENCE LISTING

```
<160> NUMBER OF SEQ ID NOS: 13

<210> SEQ ID NO 1
<211> LENGTH: 8914
<212> TYPE: DNA
<213> ORGANISM: Homo sapiens

<400> SEQUENCE: 1
ggtctaggag ggagcgcgcc gcacgcgtga gtaaacagcc ggagctggga aagtcgagct        60
ctggcagcgt ctgggtgctg aggggcagag gcggagagaa ccctgtcctg atcttcctag      120
ggtggccgac atgacggcca ggggtcagag cccccctcgcg ccgctgttgg agactttgga      180
agaccctctt gcctcccatg gagggcagac tgacgcttac ctgactctga ccagtcgtat      240
```

-continued

```
gactggagaa gaaggaaaag aagtaattac agaaattgag aaaaaacttc ctcggctgta      300
caaagtttta aagactcaca tttccagtca aaactcggag ctgagtagtg ctgctctaca      360
agccctgggg ttttgcttat ataatcccaa aattacctca gaattatcag aggcagatgc      420
tctagaattg ctttcaaaat tgaatgatac cattaagaat tcagacaaaa atgtacgtac      480
tagagcactt tgggtgatat ctaagcagac atttccctct gaagtggttg gcaaaatggt      540
atccagtata attgattcat tagaaatact gtttaacaaa ggagagacgc attctgctgt      600
tgttgatttt gaagcattaa atgttatcgt aaggctaatt gaacaagccc caattcaaat      660
gggagaagag gcagtgaggt gggcaaaact ggtcatacct ttagtggttc attcagcaca      720
aaaggtacat ttgcggggag caactgctct ggagatggga atgccattat tgcttcagaa      780
acagcaagaa atagcatcta ttacggagca gcttatgact actaaattaa tctcagaact      840
tcagaagcta tttatgagta aaaatgagac ttacgtgtta aaattatggc ctttgtttgt      900
caaactactt ggaaggacct tgcatcgaag tgggagtttc atcaattctc tcttgcaact      960
agaagaactt ggatttcgta gtggagcacc catgattaaa aagatagctt ttattgcttg     1020
gaaagtttta atagataatt ttgctttaaa tccagatata ctatgtagtg caaaaagact     1080
caagttgtta atgcagcctt tgagttccat ccatgtgaga acagaaactc tagcattaac     1140
aaaactagaa gtctggtggt atttactgat gagacttgga cctcatcttc ctgctaattt     1200
tgaacaggtt tgtgtgcctc tgattcaaag tacataagc attgattcta atgcctcacc     1260
tcagggcaat tcgtgtcatg tagctacatc tccaggttta aatcctatga ctcctgtaca     1320
caaaggtgct cctccccgt acggagcccc gggaactccc cgaatgaacc tgagttcgaa     1380
tttaggtgga atggccacaa tcccatccat tcaacttttg ggacttgaaa tgttgcttca     1440
tttcttgttg ggtccagaag ccttgagttt tgctaagcaa aataaacttg tgctgagctt     1500
agagccattg gaacatccgt taatcagcag cccttccttt ttttccaaac atgcaaatac     1560
acttatcact gctgttcatg atagctttgt tgcagttgga aaagatgccc ccgatgtggt     1620
tgtcagtgct atctggaagg agctaattag cttggtgaag tcagttactg aatcaggtaa     1680
caaaaaagag aaaccaggtt ctgaagtttt gactctctta ttaaagtctt tggaaagcat     1740
agtaaagtct gaagtatttc ctgtatcaaa acgctggtc ctcatggaaa ttacaattaa     1800
aggacttcct cagaaagtat taggttcacc agcatatcag gttgctaata tggatattct     1860
taatggaact ccagctttgt tcttaattca attaattttc aacaatttct tggaatgtgg     1920
tgtatcagat gaaaggttct ttctcagttt ggaatcactt gtaggctgtg ttctttctgg     1980
tccaacttca ccactagctt tcagtgactc agtttttaaat gttattaatc aaaatgcaaa     2040
gcagttggaa aataaggagc atctctggaa aatgtggagt gttatagtca ccccattaac     2100
tgaattgatt aatcagacca atgaagtaaa tcaaggtgat gccttagaac ataattttag     2160
tgccatctat ggtgcattga ctttaccagt aaaccacatt ttttcagaac agagatttcc     2220
agtggccacc atgaagactt tgcttagaac ttggtcagaa ttatatagag catttgctcg     2280
ttgtgctgct ttggtggcaa cagcagaaga gaacttgtgc tgtgaggaac tttcttccaa     2340
gataatgtcc agtttggaag atgaaggctt ttctaatttg ttgttcgtgg atagaattat     2400
ttatattatt actgtaatgg ttgattgcat tgacttctca ccatataata ttaaatatca     2460
gcccaaagtt aaatcaccac agagaccttc agattggtcc aaaaagaaga atgagcccct     2520
agggaaattg acttctttat ttaaacttat tgtgaaagtg atctattctt tccacacact     2580
```

```
gagcttcaag gaagcacatt ctgatacct cttcactatt ggcaactcaa tcaccggcat    2640
tatttccagt gtacttgggc atatttcttt gccttctatg atccgaaaaa tatttgcaac    2700
tttaacaaga cctctggcat tatttttatga aaactcaaag cttgatgaag ttcctaaagt    2760
atatagttgt ctgaacaaca agttagaaaa gctactggga gaaattattg cttgtctgca    2820
attcagctac accggaactt atgatagtga acttcttgaa caactctccc cactattatg    2880
cataatattt ctgcacaaga ataaacagat tcgaaacag agtgctcagt tctggaatgc    2940
cacttttgcc aaagtgatga tgttggttta tcctgaagag ttaaaaccag tactaacaca    3000
agccaaacaa aaatttctgc tcctgttgcc tggtttggaa actgttgaaa tgatggagga    3060
atccagtgga ccatattctg atggaacaga aaattcacaa ctaaatgtga agataagtgg    3120
catggagaga aaatcaaatg gaaaagaga ttcattttg gcacaaacaa agaataaaaa    3180
agaaaatatg aaaccagcag ccaaactgaa acttgaatct tcgtctttaa aagtaaaggg    3240
tgaaattctt ttggaagagg aaagtctac tgactttgtg tttataccctc cagaaggaaa    3300 agatgcaaag gaaagaatat taactgatca tcaaaagaa gttctcaaaa caaagcggtg    3360
tgatattcct gccatgtata ataatctgga tgtttcccaa gatacctatt ttactcagta    3420
tagtcaggaa gagcctatgg aaattcctac tttaaccaga aaaccaaagg aggattctaa    3480
gatgatgatt acgaggagc aaatggacag tgacattgtc attcctcaag atgtcacgga    3540
agactgtggt atggctgaac atcttgaaaa gtcctcccctt tcgaataatg agtgtggttc    3600
tcttgacaaa accagtccag aaatgtcaaa cagtaataat gatgaaagaa aaaaagcttt    3660
aatttcatca aggaaaacat caactgaatg tgcatctagt acagaaaatt ctttcgttgt    3720
cagcagtagt tcagtttcta ataccactgt tgctggaact ccccatacc ctacaagtcg    3780 gaggcaaacc tttattactt tggagaagtt tgatggttca gaaaatagac ctttttagtcc    3840 atccccttg aataatattt catcaactgt tacagtgaaa ataaccagg aaaccatgat    3900 taaaacagat tttctaccaa aagcaaagca aagagaaggg acttttttcaa aatctgattc    3960 tgaaaaaata gtgaatggaa ctaagagatc aagccggaga gctggtaaag ctgaacaaac    4020
agggaataaa aggtctaagc ccttaatgag atctgagccg gagaaaaata ctgaggaatc    4080
tgttgaaggc attgtagtct tagaaaataa cccacctggt ttgcttaatc aaacagaatg    4140
tgtgtcagat aatcaggttc atcttctga atctacaatg gagcatgaca atacaaagct    4200
taaagcagca acagtggaaa atgctgtatt attggaaact aatactgtag aggagaaaaa    4260
tgtagaaatt aatttggaat ccaaagagaa tacacccca gtagtaatat cagcagatca    4320
aatggtaaat gaggatagtc aggttcagat aactccaaat cagaaaaccc ttagacggtc    4380
ttcaaggcga cgttcagaag tagtagagtc taccactgaa agccaagata ggaaaaatag    4440
tcatcaaaaa aaggaacgac gtaaggaaga agaaaaacct cttcagaaga gtccattgca    4500
tataaaagat gatgtgttac ctaaacaaaa actgattgct gaacaaactc tacaggagaa    4560
tttaattgag aaaggaagta atttacatga agactcttt ggggaaacta gtgctaatgc    4620
agaaactgaa caaatataaaa aaaggcaga ccctgagaac attaagtctg aggggggatgg    4680 tacccaggac attgtagata agtcctctga gaaactagtc agaggccgaa cacggtatca    4740
aactagaaga gcatctcagg gtttgctttc cagcattgaa aactcagaat ctgatagttc    4800
ggaggcaaaa gaagaaggtt ctaggaagaa gagatctgga aatggaaaaa acaaaagcaa    4860
tgaaagtgtt gacattcaag atcaagaaga gaaagtggtg aaacaggaat gtataaaagc    4920
tgaaaatcag tcacatgatt ataaagcaac ttctgaagaa gatgtaagca taaaatctcc    4980
```

```
gatttgcgaa aaacaagatg aaagtaatac tgtaatatgt caggattcta cagtaacttc    5040
agatttgttg caagttcctg atgatttacc aaatgtgtgt gaggaaaaaa atgaaactag    5100
caaatatgca gaatattcct ttacaagtct acctgtgcca gaatcaaatc taaggactag    5160
aaatgccatt aagagattac ataagcgaga ctcttttgat aattgtagtt tgggagaatc    5220
ctcaaaaata gggatatcag atatttcttc gctttcagaa aaactttttc aaacacttga    5280
atgccaacac aagagaagta ggagggtgag agatctaaa ggttgtgatt gctgtgggga     5340
aaaatcacaa cctcaggaaa agtcactcat tgggttaaag aatacagaaa ataatgacgt    5400
agagattagt gaaacaaaaa aggcagatgt gcaagcacct gtaagcccat cagaaacttc    5460
tcaagctaat ccatattctg aaggacaatt tttagatgaa catcatagtg tgaattttca    5520
tttgggtctc aaagaggata atgatactat taatgattca ttaattgttt ctgaaaccaa    5580
atcaaaagaa aacactatgc aagaatctct tccttctgga atagtaaact ttagagagga    5640
aatttgtgat atggattcta gtgaagcaat gtctcttgaa agccaggagt cacctaatga    5700
aaattttaaa actgttggcc cgtgtttagg agactcgaaa aatgtttcac aggaatcttt    5760
ggagacaaaa gaagaaaaac cagaagaaac cccaaaaatg gaactgagtc tagagaatgt    5820
tactgttgaa ggaaatgcat gtaaagtaac agaatccaat ctagagaaag caaaaactat    5880
ggaattgaat gtaggaaatg aagctagctt tcatggacaa gagagaacca aaactggtat    5940
ttctgaagaa gcagcaatag aagaaaataa agaaatgat gactctgaag cagacacagc      6000
taaactgaat gccaaagaag tagcaactga ggaatttaat tcagatatta gtctttctga    6060
taatactaca cctgtaaaat tgaatgctca aactgagatt tctgaacaaa cagcagctgg    6120
ggaactagat ggaggaaatg atgtatctga tctacactca tctgaagaaa cgaataccaa    6180
aatgaaaaat tatgaagaaa tgatgatcgg cgaggcaatg gctgaaactg ccatgatgg     6240 tgaaacagag aatgagggca taactaccaa aacctcaaag cctgatgaag ctgaaacaaa    6300
catgttgact gcagaaatgg acaactttgt ttgtgacaca gttgaaatga gcactgaaga    6360
aggaatcatt gacgctaata aaactgaaac aaatactgag tatagtaaat ctgaagaaaa    6420
attagataac aatcaaatgg taatggaaag tgatattta caggaagatc accatacttc     6480
acagaaagtg gaggaaccat cacagtgtct ggcatctgga acagctatct ctgagctaat    6540
aatagaagac aataatgcat ctcctcaaaa actaagggaa cttgatcctt cacttgtgtc    6600
agcaaatgac agtcctagtg gcatgcagac acgctgtgtc tggtctcctt ggcttctcc     6660 gtctacgagc attttaaaga gaggactaaa aagatcccaa gaagatgaaa tctcatcacc    6720
tgttaataag gttcgccgtg tctccttgc agatccaata taccaagcag gattggcaga    6780
tgacattgat agacggtgct ctattgttag gtcccattct tccaatagtt ctcccatagg    6840
aaaaagtgtt aaaacttctc ctactacaca atctaagcat aataccactt cagccaaagg    6900
atttctgtcc ccaggatcac gtagccctaa atttaagagc tcaaagaagt gtttaattc     6960 agaaatggcc aaagaatcca taccatgccc aacagaaagt gtttacccac cattggtgaa    7020
ctgtgtggca ccagttgaca tcattttacc tcagattaca tcaaacatgt gggcaagagg    7080
cctgggacaa ctcattagag ctaagaatat aaaaactatt ggtgatttga gtactcttac    7140
agcatctgaa ataaaaactc ttcctatccg ttctccaaaa gtgtccaatg taaaaaaggc    7200
tctcagaata tatcatgagc agcaggtgaa gactcgtgga ctagaagaga ttccagtttt    7260
tgatatttct gaaaaaacag taaatggaat agaaaataaa tctttgtcac ctgatgaaga    7320
```

-continued

```
aagacttgtc tcagatataa ttgatcctgt tgctttagaa attccattat ccaaaaacct    7380
tgtggcacag attagtgctc ttgctcttca gctggattca gaagatcttc ataattattc    7440
aggaagccaa ctatttgaaa tgcacgagaa actaagttgt atggcaaact ctgtaataaa    7500
aaatctacag tcacgttgga gatcaccatc ccatgaaaat tctatttagt attttcagag    7560
aaaattgaag gtttttttaa acatcactgg atttcttgat tgaggaaaca agttctgaaa    7620
taatagcaca atttcaaaga agagactctt tgcaaagttg ataacatttc aaaccctgaa    7680
ggacagtgac ttattatcct tcctttctcc aaagaacagt taaaaccaaa tgtgttatgg    7740
taagctgtaa ataccgttgg aataaaagat aaccgttcat cttacctaaa aaattgaaga    7800
caatattttc cattgttgat gtcacaattt cttgaagatg ctctttgca gcctacgtgg    7860 tagtggagat atatacaaag gacttcccta gtatcgttgg accaacaagc acaagcagat    7920
ggcaggaaga ttagaacatt ggatattgat tgccagtttt taagtgtcat tcttggaaac    7980
gtgggagatt taggaaatga cattgaagag aagaattct gttgaaatag tgattctcaa     8040
cgtggggtcc ttggacagca agtgatgggg attggaatcc cttttccaac gttttctta    8100 tacaacacct gtatgacaca agaaagcatc cagaaaaaac aagagcagtc aaaacagccc    8160
tttcatctac cttgtgggga acctggtata aaactacaga cgtcagacag aaaagacaga    8220
ttcaacaagt caacctctct gttcaggcac agatctggtt ttaatgatga actctacaat    8280
gctaattctg gaaatgaaaa agtacaatgg aaagcattaa gttatataac gctgaggaat    8340
cttgttaatt ctacttatag tatttcaaat ctagtcaagt cactgaaaat gttcaagtat    8400
aatcggaaat gtgtctttcc gatagccgtt cctggtgaga catcctcttt atataaaacc    8460
tgggcattca gaatcaggac agtgttaaca cagaagaaaa gaaacccag cagttcctgg     8520 agaaagacta ggacacatgg cttttgtgaa acaagacac tagacgatgt tcccaggggt     8580
tttcgccatg aaccttgcca tgggtgagga aaagatacta tattttctcc ccaataccac    8640
caacgaagta acagatgagt ctttcatgct gtgatttggg attaagatac aaggtgagcc    8700
cagagatgaa ttgggcacac atttcctggg gcaggatggg agttgtggag gctgcacaa     8760 cagcccccact gcaagcctgg gatatccaga ggcatcttcc tcagcacccc taggtgcctg    8820
tgggctgtgc cttacattta ataaaaactt acaaggctga aaaaaaaaaa aaaaaaaaa     8880 aaaaaaaaa aaaaaaaaa aaaaaaaaa aaaa                                    8914
```

<210> SEQ ID NO 2
<211> LENGTH: 2472
<212> TYPE: PRT
<213> ORGANISM: Homo sapiens
<220> FEATURE:
<221> NAME/KEY: misc_feature
<222> LOCATION: 699
<223> OTHER INFORMATION: Xaa is any amino acid sequence
<220> FEATURE:
<221> NAME/KEY: misc_feature
<222> LOCATION: 836
<223> OTHER INFORMATION: Xaa is any amino acid sequence

<400> SEQUENCE: 2

```
Met Thr Ala Arg Gly Gln Ser Pro Leu Ala Pro Leu Leu Glu Thr Leu
 1               5                  10                  15

Glu Asp Pro Ser Ala Ser His Gly Gly Gln Thr Asp Ala Tyr Leu Thr
            20                  25                  30

Leu Thr Ser Arg Met Thr Gly Glu Glu Gly Lys Glu Val Ile Thr Glu
        35                  40                  45
```

-continued

```
Ile Glu Lys Lys Leu Pro Arg Leu Tyr Lys Val Leu Lys Thr His Ile
 50                  55                  60

Ser Ser Gln Asn Ser Glu Leu Ser Ser Ala Ala Leu Gln Ala Leu Gly
 65                  70                  75                  80

Phe Cys Leu Tyr Asn Pro Lys Ile Thr Ser Glu Leu Ser Glu Ala Asp
                     85                  90                  95

Ala Leu Glu Leu Leu Ser Lys Leu Asn Asp Thr Ile Lys Asn Ser Asp
                100                 105                 110

Lys Asn Val Arg Thr Arg Ala Leu Trp Val Ile Ser Lys Gln Thr Phe
            115                 120                 125

Pro Ser Glu Val Val Gly Lys Met Val Ser Ser Ile Ile Asp Ser Leu
130                 135                 140

Glu Ile Leu Phe Asn Lys Gly Glu Thr His Ser Ala Val Val Asp Phe
145                 150                 155                 160

Glu Ala Leu Asn Val Ile Val Arg Leu Ile Glu Gln Ala Pro Ile Gln
                165                 170                 175

Met Gly Glu Glu Ala Val Arg Trp Ala Lys Leu Val Ile Pro Leu Val
                180                 185                 190

Val His Ser Ala Gln Lys Val His Leu Arg Gly Ala Thr Ala Leu Glu
            195                 200                 205

Met Gly Met Pro Leu Leu Gln Lys Gln Gln Glu Ile Ala Ser Ile
210                 215                 220

Thr Glu Gln Leu Met Thr Thr Lys Leu Ile Ser Glu Leu Gln Lys Leu
225                 230                 235                 240

Phe Met Ser Lys Asn Glu Thr Tyr Val Leu Lys Leu Trp Pro Leu Phe
                245                 250                 255

Val Lys Leu Leu Gly Arg Thr Leu His Arg Ser Gly Ser Phe Ile Asn
                260                 265                 270

Ser Leu Leu Gln Leu Glu Glu Leu Gly Phe Arg Ser Gly Ala Pro Met
            275                 280                 285

Ile Lys Lys Ile Ala Phe Ile Ala Trp Lys Ser Leu Ile Asp Asn Phe
290                 295                 300

Ala Leu Asn Pro Asp Ile Leu Cys Ser Ala Lys Arg Leu Lys Leu Leu
305                 310                 315                 320

Met Gln Pro Leu Ser Ser Ile His Val Arg Thr Glu Thr Leu Ala Leu
                325                 330                 335

Thr Lys Leu Glu Val Trp Trp Tyr Leu Leu Met Arg Leu Gly Pro His
            340                 345                 350

Leu Pro Ala Asn Phe Glu Gln Val Cys Val Pro Leu Ile Gln Ser Thr
            355                 360                 365

Ile Ser Ile Asp Ser Asn Ala Ser Pro Gln Gly Asn Ser Cys His Val
        370                 375                 380

Ala Thr Ser Pro Gly Leu Asn Pro Met Thr Pro Val His Lys Gly Ala
385                 390                 395                 400

Ser Ser Pro Tyr Gly Ala Pro Gly Thr Pro Arg Met Asn Leu Ser Ser
                405                 410                 415

Asn Leu Gly Gly Met Ala Thr Ile Pro Ser Ile Gln Leu Leu Gly Leu
            420                 425                 430

Glu Met Leu Leu His Phe Leu Leu Gly Pro Glu Ala Leu Ser Phe Ala
        435                 440                 445

Lys Gln Asn Lys Leu Val Leu Ser Leu Glu Pro Leu Glu His Pro Leu
450                 455                 460

Ile Ser Ser Pro Ser Phe Phe Ser Lys His Ala Asn Thr Leu Ile Thr
```

-continued

```
            465                 470                 475                 480
Ala Val His Asp Ser Phe Val Ala Val Gly Lys Asp Ala Pro Asp Val
                    485                 490                 495
Val Val Ser Ala Ile Trp Lys Glu Leu Ile Ser Leu Val Lys Ser Val
                500                 505                 510
Thr Glu Ser Gly Asn Lys Lys Glu Lys Pro Gly Ser Glu Val Leu Thr
            515                 520                 525
Leu Leu Leu Lys Ser Leu Glu Ser Ile Val Lys Ser Glu Val Phe Pro
        530                 535                 540
Val Ser Lys Thr Leu Val Leu Met Glu Ile Thr Ile Lys Gly Leu Pro
545                 550                 555                 560
Gln Lys Val Leu Gly Ser Pro Ala Tyr Gln Val Ala Asn Met Asp Ile
                565                 570                 575
Leu Asn Gly Thr Pro Ala Leu Phe Leu Ile Gln Leu Ile Phe Asn Asn
            580                 585                 590
Phe Leu Glu Cys Gly Val Ser Asp Glu Arg Phe Phe Leu Ser Leu Glu
        595                 600                 605
Ser Leu Val Gly Cys Val Leu Ser Gly Pro Thr Ser Pro Leu Ala Phe
    610                 615                 620
Ser Asp Ser Val Leu Asn Val Ile Asn Gln Asn Ala Lys Gln Leu Glu
625                 630                 635                 640
Asn Lys Glu His Leu Trp Lys Met Trp Ser Val Ile Val Thr Pro Leu
                645                 650                 655
Thr Glu Leu Ile Asn Gln Thr Asn Glu Val Asn Gln Gly Asp Ala Leu
            660                 665                 670
Glu His Asn Phe Ser Ala Ile Tyr Gly Ala Leu Thr Leu Pro Val Asn
        675                 680                 685
His Ile Phe Ser Glu Gln Arg Phe Pro Val Xaa Thr Met Lys Thr Leu
    690                 695                 700
Leu Arg Thr Trp Ser Glu Leu Tyr Arg Ala Phe Ala Arg Cys Ala Ala
705                 710                 715                 720
Leu Val Ala Thr Ala Glu Glu Asn Leu Cys Cys Glu Glu Leu Ser Ser
                725                 730                 735
Lys Ile Met Ser Ser Leu Glu Asp Glu Gly Phe Ser Asn Leu Leu Phe
            740                 745                 750
Val Asp Arg Ile Ile Tyr Ile Ile Thr Val Met Val Asp Cys Ile Asp
        755                 760                 765
Phe Ser Pro Tyr Asn Ile Lys Tyr Gln Pro Lys Val Lys Ser Pro Gln
    770                 775                 780
Arg Pro Ser Asp Trp Ser Lys Lys Asn Glu Pro Leu Gly Lys Leu
785                 790                 795                 800
Thr Ser Leu Phe Lys Leu Ile Val Lys Val Ile Tyr Ser Phe His Thr
                805                 810                 815
Leu Ser Phe Lys Glu Ala His Ser Asp Thr Leu Phe Thr Ile Gly Asn
            820                 825                 830
Ser Ile Thr Xaa Ile Ile Ser Ser Val Leu Gly His Ile Ser Leu Pro
        835                 840                 845
Ser Met Ile Arg Lys Ile Phe Ala Thr Leu Thr Arg Pro Leu Ala Leu
    850                 855                 860
Phe Tyr Glu Asn Ser Lys Leu Asp Glu Val Pro Lys Val Tyr Ser Cys
865                 870                 875                 880
Leu Asn Asn Lys Leu Glu Lys Leu Leu Gly Glu Ile Ile Ala Cys Leu
                885                 890                 895
```

-continued

```
Gln Phe Ser Tyr Thr Gly Thr Tyr Asp Ser Glu Leu Leu Glu Gln Leu
            900                 905                 910

Ser Pro Leu Leu Cys Ile Ile Phe Leu His Lys Asn Lys Gln Ile Arg
            915                 920                 925

Lys Gln Ser Ala Gln Phe Trp Asn Ala Thr Phe Ala Lys Val Met Met
            930                 935                 940

Leu Val Tyr Pro Glu Glu Leu Lys Pro Val Leu Thr Gln Ala Lys Gln
945                 950                 955                 960

Lys Phe Leu Leu Leu Leu Pro Gly Leu Glu Thr Val Glu Met Met Glu
                965                 970                 975

Glu Ser Ser Gly Pro Tyr Ser Asp Gly Thr Glu Asn Ser Gln Leu Asn
            980                 985                 990

Val Lys Ile Ser Gly Met Glu Arg Lys Ser Asn Gly Lys Arg Asp Ser
            995                 1000                1005

Phe Leu Ala Gln Thr Lys Asn Lys Lys Glu Asn Met Lys Pro Ala Ala
            1010                1015                1020

Lys Leu Lys Leu Glu Ser Ser Ser Leu Lys Val Lys Gly Glu Ile Leu
1025                1030                1035                1040

Leu Glu Glu Glu Lys Ser Thr Asp Phe Val Phe Ile Pro Pro Glu Gly
                1045                1050                1055

Lys Asp Ala Lys Glu Arg Ile Leu Thr Asp His Gln Lys Glu Val Leu
            1060                1065                1070

Lys Thr Lys Arg Cys Asp Ile Pro Ala Met Tyr Asn Asn Leu Asp Val
            1075                1080                1085

Ser Gln Asp Thr Leu Phe Thr Gln Tyr Ser Gln Glu Glu Pro Met Glu
            1090                1095                1100

Ile Pro Thr Leu Thr Arg Lys Pro Lys Glu Asp Ser Lys Met Met Ile
1105                1110                1115                1120

Thr Glu Glu Gln Met Asp Ser Asp Ile Val Ile Pro Gln Asp Val Thr
                1125                1130                1135

Glu Asp Cys Gly Met Ala Glu His Leu Glu Lys Ser Ser Leu Ser Asn
            1140                1145                1150

Asn Glu Cys Gly Ser Leu Asp Lys Thr Ser Pro Glu Met Ser Asn Ser
            1155                1160                1165

Asn Asn Asp Glu Arg Lys Lys Ala Leu Ile Ser Ser Arg Lys Thr Ser
            1170                1175                1180

Thr Glu Cys Ala Ser Ser Thr Glu Asn Ser Phe Val Val Ser Ser Ser
1185                1190                1195                1200

Ser Val Ser Asn Thr Thr Val Ala Gly Thr Pro Pro Tyr Pro Thr Ser
            1205                1210                1215

Arg Arg Gln Thr Phe Ile Thr Leu Glu Lys Phe Asp Gly Ser Glu Asn
            1220                1225                1230

Arg Pro Phe Ser Pro Ser Pro Leu Asn Asn Ile Ser Ser Thr Val Thr
            1235                1240                1245

Val Lys Asn Asn Gln Glu Thr Val Ile Lys Thr Asp Phe Leu Pro Lys
1250                1255                1260

Ala Lys Gln Arg Glu Gly Thr Phe Ser Lys Ser Asp Ser Glu Lys Ile
1265                1270                1275                1280

Val Asn Gly Thr Lys Arg Ser Ser Arg Arg Ala Gly Lys Ala Glu Gln
            1285                1290                1295

Thr Gly Asn Lys Arg Ser Lys Pro Leu Met Arg Ser Glu Pro Glu Lys
            1300                1305                1310
```

-continued

Asn Thr Glu Glu Ser Val Glu Gly Ile Val Val Leu Glu Asn Asn Pro
        1315                1320                1325

Pro Gly Leu Leu Asn Gln Thr Glu Cys Val Ser Asp Asn Gln Val His
        1330                1335                1340

Leu Ser Glu Ser Thr Met Glu His Asp Asn Thr Lys Leu Lys Ala Ala
1345                1350                1355                1360

Thr Val Glu Asn Ala Val Leu Leu Glu Thr Asn Thr Val Glu Lys
        1365                1370                1375

Asn Val Glu Ile Asn Leu Glu Ser Lys Glu Asn Thr Pro Val Val
        1380                1385                1390

Ile Ser Ala Asp Gln Met Val Asn Glu Asp Ser Gln Val Gln Ile Thr
        1395                1400                1405

Pro Asn Gln Lys Thr Leu Arg Arg Ser Ser Arg Arg Ser Glu Val
        1410                1415                1420

Val Glu Ser Thr Thr Glu Ser Gln Asp Lys Glu Asn Ser His Gln Lys
1425                1430                1435                1440

Lys Glu Arg Arg Lys Glu Glu Lys Pro Leu Gln Lys Ser Pro Leu
        1445                1450                1455

His Ile Lys Asp Asp Val Leu Pro Lys Gln Lys Leu Ile Ala Glu Gln
        1460                1465                1470

Thr Leu Gln Glu Asn Leu Ile Glu Lys Gly Ser Asn Leu His Glu Lys
        1475                1480                1485

Thr Leu Gly Glu Thr Ser Ala Asn Ala Glu Thr Glu Gln Asn Lys Lys
        1490                1495                1500

Lys Ala Asp Pro Glu Asn Ile Lys Ser Glu Gly Asp Gly Thr Gln Asp
1505                1510                1515                1520

Ile Val Asp Lys Ser Ser Glu Lys Leu Val Arg Gly Arg Thr Arg Tyr
        1525                1530                1535

Gln Thr Arg Arg Ala Ser Gln Gly Leu Leu Ser Ser Ile Glu Asn Ser
        1540                1545                1550

Glu Ser Asp Ser Ser Glu Ala Lys Glu Glu Gly Ser Arg Lys Lys Arg
        1555                1560                1565

Ser Gly Lys Trp Lys Asn Lys Ser Asn Glu Ser Val Asp Ile Gln Asp
        1570                1575                1580

Gln Glu Glu Lys Val Val Lys Gln Glu Cys Ile Lys Ala Glu Asn Gln
1585                1590                1595                1600

Ser His Asp Tyr Lys Ala Thr Ser Glu Glu Asp Val Ser Ile Lys Ser
        1605                1610                1615

Pro Ile Cys Glu Lys Gln Asp Glu Ser Asn Thr Val Ile Cys Gln Asp
        1620                1625                1630

Ser Thr Val Thr Ser Asp Leu Leu Gln Val Pro Asp Asp Leu Pro Asn
        1635                1640                1645

Val Cys Glu Glu Lys Asn Glu Thr Ser Lys Tyr Ala Glu Tyr Ser Phe
        1650                1655                1660

Thr Ser Leu Pro Val Pro Glu Ser Asn Leu Arg Thr Arg Asn Ala Ile
1665                1670                1675                1680

Lys Arg Leu His Lys Arg Asp Ser Phe Asp Asn Cys Ser Leu Gly Glu
        1685                1690                1695

Ser Ser Lys Ile Gly Ile Ser Asp Ile Ser Ser Leu Ser Glu Lys Thr
        1700                1705                1710

Phe Gln Thr Leu Glu Cys Gln His Lys Arg Ser Arg Arg Val Arg Arg
        1715                1720                1725

Ser Lys Gly Cys Asp Cys Cys Gly Glu Lys Ser Gln Pro Gln Glu Lys

```
                              -continued
      1730            1735           1740
Ser Leu Ile Gly Leu Lys Asn Thr Glu Asn Asp Val Glu Ile Ser
1745             1750            1755             1760

Glu Thr Lys Lys Ala Asp Val Gln Ala Pro Val Ser Pro Ser Glu Thr
             1765             1770            1775

Ser Gln Ala Asn Pro Tyr Ser Glu Gly Gln Phe Leu Asp Glu His His
            1780             1785            1790

Ser Val Asn Phe His Leu Gly Leu Lys Glu Asp Asn Asp Thr Ile Asn
            1795             1800            1805

Asp Ser Leu Ile Val Ser Glu Thr Lys Ser Lys Glu Asn Thr Met Gln
1810             1815            1820

Lys Thr Leu Pro Ser Gly Ile Val Asn Leu Lys Glu Glu Ile Cys Asp
1825             1830            1835            1840

Met Asp Ser Ser Glu Ala Met Ser Leu Glu Ser Gln Glu Ser Pro Asn
            1845             1850            1855

Glu Asn Phe Lys Thr Val Gly Pro Cys Leu Gly Asp Ser Lys Asn Val
            1860             1865            1870

Ser Gln Glu Ser Leu Glu Thr Lys Glu Glu Lys Pro Glu Glu Thr Pro
            1875             1880            1885

Lys Met Glu Leu Ser Leu Glu Asn Val Thr Val Glu Gly Asn Ala Cys
            1890             1895            1900

Lys Val Thr Glu Ser Asn Leu Glu Lys Ala Lys Thr Met Glu Leu Asn
1905             1910            1915            1920

Val Gly Asn Glu Ala Ser Phe His Gly Gln Glu Arg Thr Lys Thr Gly
            1925             1930            1935

Ile Ser Glu Glu Ala Ala Ile Glu Glu Asn Lys Arg Asn Asp Asp Ser
            1940             1945            1950

Glu Ala Asp Thr Ala Lys Leu Asn Ala Lys Glu Val Ala Thr Glu Glu
            1955             1960            1965

Phe Asn Ser Asp Ile Ser Leu Ser Asp Asn Thr Thr Pro Val Lys Leu
1970             1975            1980

Asn Ala Gln Thr Glu Ile Ser Glu Gln Thr Ala Ala Gly Glu Leu Asp
1985             1990            1995            2000

Gly Gly Asn Asp Val Ser Asp Leu His Ser Ser Glu Glu Thr Asn Thr
            2005             2010            2015

Lys Met Lys Asn Tyr Glu Glu Met Met Ile Gly Glu Ala Met Ala Glu
            2020             2025            2030

Thr Gly His Asp Gly Glu Thr Glu Asn Glu Gly Ile Thr Thr Lys Thr
            2035             2040            2045

Ser Lys Pro Asp Glu Ala Glu Thr Asn Met Leu Thr Ala Glu Met Asp
            2050             2055            2060

Asn Phe Val Cys Asp Thr Val Glu Met Ser Thr Glu Glu Gly Ile Ile
2065             2070            2075            2080

Asp Ala Asn Lys Thr Glu Thr Asn Thr Glu Tyr Ser Lys Ser Glu Glu
            2085             2090            2095

Lys Leu Asp Asn Asn Gln Met Val Met Glu Ser Asp Ile Leu Gln Glu
            2100             2105            2110

Asp His His Thr Ser Gln Lys Val Glu Glu Pro Ser Gln Cys Leu Ala
            2115             2120            2125

Ser Gly Thr Ala Ile Ser Glu Leu Ile Ile Glu Asp Asn Asn Ala Ser
            2130             2135            2140

Pro Gln Lys Leu Arg Glu Leu Asp Pro Ser Leu Val Ser Ala Asn Asp
2145             2150            2155            2160
```

-continued

```
Ser Pro Ser Gly Met Gln Thr Arg Cys Val Trp Ser Pro Leu Ala Ser
            2165                2170                2175

Pro Ser Thr Ser Ile Leu Lys Arg Gly Leu Lys Arg Ser Gln Glu Asp
        2180                2185                2190

Glu Ile Ser Ser Pro Val Asn Lys Val Arg Arg Val Ser Phe Ala Asp
            2195                2200                2205

Pro Ile Tyr Gln Ala Gly Leu Ala Asp Asp Ile Asp Arg Arg Cys Ser
        2210                2215                2220

Ile Val Arg Ser His Ser Ser Asn Ser Ser Pro Ile Gly Lys Ser Val
2225                2230                2235                2240

Lys Thr Ser Pro Thr Thr Gln Ser Lys His Asn Thr Thr Ser Ala Lys
            2245                2250                2255

Gly Phe Leu Ser Pro Gly Ser Arg Ser Pro Lys Phe Lys Ser Ser Lys
        2260                2265                2270

Lys Cys Leu Ile Ser Glu Met Ala Lys Glu Ser Ile Pro Cys Pro Thr
        2275                2280                2285

Glu Ser Val Tyr Pro Pro Leu Val Asn Cys Val Ala Pro Val Asp Ile
        2290                2295                2300

Ile Leu Pro Gln Ile Thr Ser Asn Met Trp Ala Arg Gly Leu Gly Gln
2305                2310                2315                2320

Leu Ile Arg Ala Lys Asn Ile Lys Thr Ile Gly Asp Leu Ser Thr Leu
            2325                2330                2335

Thr Ala Ser Glu Ile Lys Thr Leu Pro Ile Arg Ser Pro Lys Val Ser
            2340                2345                2350

Asn Val Lys Lys Ala Leu Arg Ile Tyr His Glu Gln Gln Val Lys Thr
            2355                2360                2365

Arg Gly Leu Glu Glu Ile Pro Val Phe Asp Ile Ser Glu Lys Thr Val
        2370                2375                2380

Asn Gly Ile Glu Asn Lys Ser Leu Ser Pro Asp Glu Glu Arg Leu Val
2385                2390                2395                2400

Ser Asp Ile Ile Asp Pro Val Ala Leu Glu Ile Pro Leu Ser Lys Asn
            2405                2410                2415

Leu Val Ala Gln Ile Ser Ala Leu Ala Leu Gln Leu Asp Ser Glu Asp
            2420                2425                2430

Leu His Asn Tyr Ser Gly Ser Gln Leu Phe Glu Met His Glu Lys Leu
            2435                2440                2445

Ser Cys Met Ala Asn Ser Val Ile Lys Asn Leu Gln Ser Arg Trp Arg
            2450                2455                2460

Ser Pro Ser His Glu Asn Ser Ile
2465                2470

<210> SEQ ID NO 3
<211> LENGTH: 25
<212> TYPE: PRT
<213> ORGANISM: Homo sapiens

<400> SEQUENCE: 3

Asn Ser Glu Ser Asp Ser Ser Glu Ala Lys Glu Glu Gly Ser Arg Lys
 1               5                  10                  15

Lys Arg Ser Gly Lys Trp Lys Asn Lys
            20                  25

<210> SEQ ID NO 4
<211> LENGTH: 25
<212> TYPE: PRT
```

-continued

<213> ORGANISM: Homo sapiens

<400> SEQUENCE: 4

Glu Glu Gly Ile Ile Asp Ala Asn Lys Thr Glu Thr Asn Thr Glu Tyr
 1               5                  10                  15

Ser Lys Ser Glu Glu Lys Leu Asp Asn
            20                  25

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1) ... (21)
<223> OTHER INFORMATION: RNA component of siRNA synthetic
      oligonucleotide
<220> FEATURE:
<221> NAME/KEY: misc_feature
<222> LOCATION: 22, 23
<223> OTHER INFORMATION: DNA component of siRNA synthetic
      oligonucleotide

<400> SEQUENCE: 5
aacagcaaga aauagcaccu att                                        23

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1) ... (21)
<223> OTHER INFORMATION: RNA component of siRNA synthetic
      oligonucleotide
<220> FEATURE:
<221> NAME/KEY: misc_feature
<222> LOCATION: 22, 23
<223> OTHER INFORMATION: DNA component of siRNA synthetic
      oligonucleotide

<400> SEQUENCE: 6
aaugagacuu acguguuaaa att                                        23

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1) ... (21)
<223> OTHER INFORMATION: RNA component of siRNA synthetic
      oligonucleotide
<220> FEATURE:
<221> NAME/KEY: misc_feature
<222> LOCATION: 22, 23
<223> OTHER INFORMATION: DNA component of siRNA synthetic
      oligonucleotide

<400> SEQUENCE: 7
aagagaaacc agguucugaa gtt                                        23

<210> SEQ ID NO 8
<211> LENGTH: 23

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1) ... (21)
<223> OTHER INFORMATION: RNA component of siRNA synthetic
      oligonucleotide
<220> FEATURE:
<221> NAME/KEY: misc_feature
<222> LOCATION: 22, 23
<223> OTHER INFORMATION: DNA component of siRNA synthetic
      oligonucleotide

<400> SEQUENCE: 8
aagaaugagc cccuagggaa att                                           23

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1) ... (21)
<223> OTHER INFORMATION: RNA component of siRNA synthetic
      oligonucleotide
<220> FEATURE:
<221> NAME/KEY: misc_feature
<222> LOCATION: 22, 23
<223> OTHER INFORMATION: DNA component of siRNA synthetic
      oligonucleotide

<400> SEQUENCE: 9
aagaggaaaa gucuacugac utt                                           23

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1) ... (21)
<223> OTHER INFORMATION: RNA component of siRNA synthetic
      oligonucleotide
<220> FEATURE:
<221> NAME/KEY: misc_feature
<222> LOCATION: 22, 23
<223> OTHER INFORMATION: DNA component of siRNA synthetic
      oligonucleotide

<400> SEQUENCE: 10
aagagcaucu caggguuugc utt                                           23

<210> SEQ ID NO 11
<211> LENGTH: 2426
<212> TYPE: PRT
<213> ORGANISM: Mus musculus

<400> SEQUENCE: 11

Met Thr Ala Pro Gly Arg Ser Pro Leu Glu Pro Leu Leu Glu Thr Trp
 1               5                  10                  15

Glu Asp Pro Ser Val Pro Pro Gly Glu Gln Thr Asp Ala Tyr Leu Thr
                20                  25                  30

Leu Thr Ser Arg Met Thr Gly Glu Glu Gly Lys Glu Val Ile Ala Glu
            35                  40                  45
```

-continued

```
Ile Glu Lys Asn Leu Ser Arg Leu Tyr Thr Val Leu Lys Ala His Ile
     50                  55                  60

Ser Ser Gln Asn Ser Glu Leu Ser Ser Ala Ala Leu Gln Ala Leu Gly
 65                  70                  75                  80

Phe Cys Leu Tyr Asn Pro Arg Ile Thr Ser Gly Leu Ser Glu Ala Asn
                 85                  90                  95

Ile Gln Glu Leu Leu Thr Leu Asn Gly Ile Ile Lys Ser Ser Asp
            100                 105                 110

Lys Asn Val Cys Thr Arg Ala Leu Trp Val Ile Ser Lys Gln Thr Phe
            115                 120                 125

Pro Ala Glu Leu Val Ser Lys Met Val Ser Ile Ile Asp Ser Leu
            130                 135                 140

Glu Val Ile Leu Ser Lys Gly Glu Ile His Ser Ala Val Val Asp Phe
145                 150                 155                 160

Glu Ala Leu Asn Val Ile Ile Ser His Trp Phe Leu His Cys Arg Leu
                165                 170                 175

Ile Glu Gln Ala Pro Val Gln Met Gly Glu Ser Val Arg Trp Ala
            180                 185                 190

Lys Leu Val Ile Pro Leu Val Val His Ser Ala Gln Lys Val His Leu
            195                 200                 205

Arg Gly Ala Thr Ala Leu Glu Met Gly Met Pro Leu Leu Leu Gln Lys
            210                 215                 220

Gln Gln Glu Ile Ala Leu Ile Thr Glu His Leu Met Thr Thr Lys Leu
225                 230                 235                 240

Ile Ser Glu Leu Gln Lys Leu Phe Lys Asn Lys Asn Glu Thr Tyr Val
                245                 250                 255

Leu Lys Leu Trp Pro Leu Phe Val Lys Leu Leu Gly Lys Thr Leu His
            260                 265                 270

Arg Ser Gly Ser Phe Ile Asn Ser Leu Leu Gln Leu Glu Glu Leu Gly
            275                 280                 285

Phe Arg Ser Gly Thr Pro Met Ile Lys Lys Ile Ala Phe Ile Ala Trp
            290                 295                 300

Lys Ser Leu Ile Asp Asn Phe Ala Leu Asn Pro Asp Ile Leu Cys Ser
305                 310                 315                 320

Ala Lys Arg Leu Lys Leu Leu Met Gln Pro Leu Ser Ser Ile His Val
                325                 330                 335

Arg Thr Glu Thr Leu Ala Leu Thr Lys Leu Glu Val Trp Trp Tyr Leu
            340                 345                 350

Leu Met Arg Leu Gly Pro Gln Leu Pro Ala Asn Phe Glu Gln Val Cys
            355                 360                 365

Val Pro Leu Ile Gln Ser Thr Ile Ser Val Asp Ser Ile Pro Ser Pro
            370                 375                 380

Gln Gly Asn Ser Ser Arg Gly Ser Ala Ser Pro Gly Leu Ser Pro Leu
385                 390                 395                 400

Thr Pro Gly His Lys Gly Ala Ser Pro Tyr Gly Ser Pro Arg Gly Asn
                405                 410                 415

Leu Ser Ser Asn Thr Gly Gly Met Ala Ala Ile Pro Ser Ile Gln Leu
            420                 425                 430

Leu Gly Leu Glu Met Met Leu His Phe Leu Leu Gly Pro Glu Val Leu
            435                 440                 445

Ser Phe Ala Lys Gln His Lys Ile Val Leu Ser Leu Glu Pro Leu Glu
450                 455                 460
```

-continued

```
His Pro Leu Ile Ser Ser Pro Ser Phe Phe Ser Lys Tyr Ala His Thr
465                 470                 475                 480

Leu Ile Thr Ala Val His Asp Ser Phe Val Ser Val Gly Lys Asp Ala
            485                 490                 495

Ser Asp Ala Val Val Ser Ala Ile Trp Lys Glu Leu Ile Ser Leu Val
        500                 505                 510

Lys Ser Val Thr Glu Ala Gly Asn Arg Lys Glu Lys Ser Gly Ser Glu
    515                 520                 525

Val Leu Thr Leu Leu Lys Ser Leu Glu Asn Ile Val Lys Ser Glu
530                 535                 540

Val Phe Pro Val Ser Lys Thr Leu Val Leu Met Glu Ile Thr Val Lys
545                 550                 555                 560

Gly Leu Pro Pro Lys Val Leu Gly Ser Pro Ala Tyr Gln Val Ala Asn
                565                 570                 575

Met Asp Ile Leu Asn Gly Thr Pro Ala Leu Phe Leu Ile Gln Leu Ile
            580                 585                 590

Phe Asn Asn Asn Leu Leu Glu Cys Gly Val Glu Asp Glu Lys Phe Phe
        595                 600                 605

Leu Asn Leu Glu Thr Leu Val Gly Cys Val Leu Ser Gly Pro Thr Ser
    610                 615                 620

Pro Leu Ala Phe Ser Asp Ser Val Leu Thr Val Ile Asn Gln Asn Ala
625                 630                 635                 640

Lys Gln Leu Val Asn Lys Glu His Leu Trp Arg Met Trp Ser Met Ile
                645                 650                 655

Val Ser Pro Leu Thr Asp Val Ile His Gln Thr Asn Glu Val Asn Gln
            660                 665                 670

Gly Asp Ala Leu Glu His Asn Phe Ser Ala Ile Tyr Gly Ala Leu Thr
        675                 680                 685

Leu Pro Ile Asn His Ile Phe Ser Ala Gln Thr Phe Pro Thr Gly Thr
    690                 695                 700

Met Lys Ala Leu Leu Lys Thr Trp Ser Glu Leu Tyr Arg Ala Phe Thr
705                 710                 715                 720

Arg Cys Ala Ser Leu Val Ala Thr Ala Glu Glu Asn Leu Cys Cys Glu
                725                 730                 735

Glu Leu Ser Ser Lys Ile Met Cys Ser Leu Glu Asp Glu Val Leu Ser
            740                 745                 750

Asp Leu Leu Phe Leu Asp Arg Ile Ser His Ile Ile Val Met Val
        755                 760                 765

Asp Cys Ile Asp Phe Ser Pro Tyr Asn Lys Lys Tyr Gln Pro Lys Ile
    770                 775                 780

Lys Ser Pro Gln Arg Ser Ser Asp Trp Ser Arg Lys Lys Lys Glu Pro
785                 790                 795                 800

Leu Gly Lys Leu Ala Ser Leu Phe Lys Leu Ile Val Lys Val Ile Asp
                805                 810                 815

Thr Phe His Thr Leu Ser Leu Lys Glu Thr Phe Ser Asp Thr Leu Leu
            820                 825                 830

Ala Ile Gly Asn Ser Ile Ile Ser Met Leu Ser Asn Val Phe Gly His
        835                 840                 845

Ile Ser Leu Pro Ser Met Ile Arg Glu Ile Phe Ala Thr Phe Thr Arg
    850                 855                 860

Pro Leu Ala Leu Leu Tyr Glu Asn Ser Lys Leu Asp Glu Ala Pro Lys
865                 870                 875                 880

Val Tyr Thr Ser Leu Asn Asn Lys Leu Glu Lys Leu Leu Gly Glu Ile
```

-continued

```
                885                 890                 895
Val Ala Cys Leu Gln Phe Ser Tyr Leu Gly Ala Tyr Asp Ser Glu Leu
                900                 905                 910
Leu Glu His Leu Ser Pro Leu Leu Cys Val Ile Phe Leu His Lys Asn
            915                 920                 925
Lys Gln Ile Arg Lys Gln Ser Ala Leu Leu Trp Asn Ala Thr Phe Ala
        930                 935                 940
Lys Ala Thr Ala Leu Val Tyr Pro Glu Glu Leu Lys Pro Ile Leu Arg
945                 950                 955                 960
Gln Ala Lys Gln Lys Ile Leu Leu Leu Pro Gly Leu Glu Asn Val
                965                 970                 975
Glu Met Met Asp Glu Ser Ser Glu Pro Tyr Ser Glu Ser Thr Glu Asn
                980                 985                 990
Ser Gln Leu Asn Val Lys Ile Ser Gly Met Glu Arg Lys Ser Ser Gly
            995                1000                1005
Lys Arg Asp Ser Ile Leu Ala His Thr Lys Asp Lys Lys Lys Val
        1010                1015                1020
Lys Leu Ser Ala Lys Leu Lys Leu Glu Ser Ser Pro Lys Ile Lys
1025                1030                1035                1040
Ser Gly Lys Leu Leu Glu Glu Lys Ser Thr Asp Phe Val Phe Ile
                1045                1050                1055
Pro Pro Glu Gly Lys Glu Thr Lys Ala Arg Val Leu Thr Glu His Gln
            1060                1065                1070
Lys Glu Val Leu Lys Thr Lys Arg Cys Asp Ile Pro Ala Leu Tyr Asn
        1075                1080                1085
Asn Leu Asp Ala Ser Gln Asp Thr Leu Phe Ser Ala Gln Phe Ser Gln
        1090                1095                1100
Glu Glu Ser Met Glu Ser Leu Thr Leu Thr Glu Lys Pro Lys Glu Asp
1105                1110                1115                1120
Ala Lys Ile Ile Lys Glu Glu Gln Met Glu Ser Thr Ile Phe Ile His
                1125                1130                1135
Gln Asp Ala Pro Glu Asn Cys Gly Ile Asp Glu His Ser Glu Asn Ala
            1140                1145                1150
Ser Leu Pro Asn Cys Gly Gly Ser Val Ala Glu Thr Asn Pro Glu Thr
        1155                1160                1165
Leu Ile Thr Gly Phe Asp Ala Arg Lys Glu Val Leu Ile Ser Ser Lys
        1170                1175                1180
Ile Leu Ser Ala Glu Ser Ser Ser Thr Glu Thr Ser Val Val Ser
1185                1190                1195                1200
Ser Ser Ser Val Ser Asn Ala Thr Phe Ser Gly Thr Pro Pro Gln Pro
                1205                1210                1215
Thr Ser Arg Arg Gln Thr Phe Ile Thr Leu Gly Lys Phe Asp Gly Ser
            1220                1225                1230
Glu Thr Arg Pro Phe Ser Pro Ser Pro Leu Asn Asn Ile Ser Ser Thr
        1235                1240                1245
Val Thr Val Arg Asn Asn Gln Asp Asn Thr Asn Thr Asp Met Pro
        1250                1255                1260
Pro Lys Ala Arg Lys Arg Glu Val Thr Asn Ser Lys Ser Asp Ser Glu
1265                1270                1275                1280
Asn Leu Ala Asn Ala Gly Lys Lys Ser Ser Arg Arg Trp Ser Lys Ala
                1285                1290                1295
Glu Gln Ser Val Thr Lys Lys Ser Lys Pro Ser Leu Thr Ser Glu Gln
            1300                1305                1310
```

```
Glu Glu His Ser Ser Glu Asn Asn Ser Pro Asp Leu Leu Ser Pro Thr
        1315                1320                1325

Glu His Val Ser Glu Asn Asp Asp His Pro Ser Glu Ala Thr Leu Glu
        1330                1335                1340

His Lys Asp Gly Asp Pro Lys Pro Ala Val Glu Asn Ala Ser Leu Glu
1345                1350                1355                1360

Asp Leu Thr Thr Glu Glu Lys Asn Val Gly Ile Asn Met Glu Ser Lys
            1365                1370                1375

Glu Ser Thr Ala Ser Val Val Ala Arg Thr Glu Gln Ile Val Asn Glu
        1380                1385                1390

Asp Ser Gln Ala Ala Ala Leu Ala Pro Asn Pro Lys Thr Leu Arg Arg
        1395                1400                1405

Ser Ser Arg Arg Arg Ser Glu Ala Val Asp Ser Cys Ser Asp Ser Gln
        1410                1415                1420

Glu Arg Glu Ser Gly Gln Gln Lys Lys Glu Arg Arg Lys Glu Glu
1425                1430                1435                1440

Lys Ile Ile Ser Lys Ser Pro Leu Arg Ile Lys Asp Asp Lys Leu Pro
            1445                1450                1455

Thr Gln Lys Leu Thr Asp Glu Ser Pro Ile Gln Glu Asn Leu Thr Glu
            1460                1465                1470

Lys Gly Asn Thr Leu Pro Glu Arg Thr Ser Gly Glu Pro Ser Val Asn
        1475                1480                1485

Ala Glu Ile Asp Gln Asn Arg Arg Lys Pro Asp Leu Glu Asn Val Ser
        1490                1495                1500

Ser Glu Gly Gly Gly Gly Thr Leu Asp Asn Leu Asp Lys Ser Ser Glu
1505                1510                1515                1520

Lys Pro Leu Arg Gly Arg Thr Arg Tyr Gln Thr Arg Ala Ser Gln
        1525                1530                1535

Gly Leu Ile Ser Ala Val Glu Asn Ser Glu Ser Asp Ser Ser Glu Ala
            1540                1545                1550

Lys Glu Glu Val Ser Arg Lys Lys Arg Ser Gly Lys Trp Lys Asn Arg
        1555                1560                1565

Ser Ser Asp Ser Val Asp Ile Glu Glu Gln Glu Glu Lys Lys Ala Glu
        1570                1575                1580

Glu Glu Val Met Lys Thr Ala Asn Gln Thr Leu Asp Gly Gln Ala Val
1585                1590                1595                1600

Pro Asp Val Asp Val Asn Ala Ala Ala Gln Val Cys Glu Lys Ser Thr
            1605                1610                1615

Asn Asn Asn Arg Val Ile Leu Gln Asp Ser Ala Gly Pro Ala Asp Ser
        1620                1625                1630

Leu Gln Ala Pro Pro Lys Gly Glu Glu Lys Ser Lys Ile Asn Lys Cys
        1635                1640                1645

Val Asp Ser Ser Phe Val Ser Leu Pro Val Pro Glu Ser Asn Leu Arg
        1650                1655                1660

Thr Arg Asn Ala Ser Lys Arg Leu Leu Tyr Lys Gln Asp Asn Asp Ser
1665                1670                1675                1680

Asn Val Arg Val Ser Asp Ser Ser Leu Ser Pro Glu Lys Phe Thr Gln
            1685                1690                1695

Val Glu Cys Gln His Lys Arg Ser Arg Arg Val Arg Ser Lys Ser
        1700                1705                1710

Cys Asp Cys Cys Gly Glu Lys Ser Gln Ser Gln Glu Lys Ser Phe Ile
        1715                1720                1725
```

```
Gly Leu Lys Asn Thr Glu Ser Tyr Ala Ile Lys Ser Val Glu Lys Lys
        1730                1735                1740
Lys Thr Asp Leu Gln Val Pro Glu Thr Ala Pro Glu Thr Arg Glu Ala
1745                1750                1755                1760
Arg Asp His Ala Glu Thr Lys Leu Ala Gly Glu Glu Pro Leu Val Asn
                1765                1770                1775
Phe His Val Gly Leu Lys Glu Glu Asn Cys Thr Thr Gly Asp Ser Val
                1780                1785                1790
Lys Ser Glu Ala Glu Leu Gln Glu Ala Ser Leu Pro Pro Glu Ile Val
            1795                1800                1805
Thr Val Lys Glu Lys Thr Tyr Asp Thr Asp Ala Ser Glu Ala Val Ser
        1810                1815                1820
Glu Ile Gln Gly Pro Cys Ser Glu Asn His Ser Pro Ala Glu Asp Pro
1825                1830                1835                1840
Gly Leu Ser Glu Cys Lys Asp Ile Ser Gln Lys Gln Leu Ser Glu Asn
                1845                1850                1855
Gly Glu Leu Asp Ile Ser Asp Val Gly Lys Ala Cys Lys Val Ile Ala
                1860                1865                1870
Gly Ser Ser Pro Glu Gly Val Glu Thr Met Glu Leu Asn Val Arg Asn
            1875                1880                1885
Asp Ala Phe Val Ala Ala Asp Ser Glu Lys Ser Thr Gln Met Asp Val
        1890                1895                1900
Ser Val Asp Val Ala Thr Glu Glu Asp Asn Lys Lys Asp Glu Cys Glu
1905                1910                1915                1920
Ala Val Thr Thr Glu Val Asn Val Glu Gly Val Ala Thr Glu Asp Phe
                1925                1930                1935
Asn Ser Gly Met Asp Leu Ser Asp Thr Pro Ile Pro Val Ser Lys Asp
                1940                1945                1950
Val Glu Thr Glu His Ala Ala Ser Gly Glu Ile Glu Gly Glu Ser Asn
            1955                1960                1965
Glu Ser Asp Ser Gly Ser Cys Glu Glu Met Asn Lys Glu Met Gly Ser
        1970                1975                1980
His Lys Ala Gln Met Ser Thr Glu Ile Asp Ser Ala Arg Val Lys Glu
1985                1990                1995                2000
Thr Asp Ile Leu Ala Ser Ala Ser Lys Ser Glu Glu Ala Leu Ile Gly
                2005                2010                2015
Arg Leu Asp Val Asn Thr Gln Ser Phe Val Ser Asp Ile Glu Met Ser
                2020                2025                2030
Ser Gly Glu Arg Thr Val Asn Cys Lys Thr Glu Thr Ser Ile Glu Leu
            2035                2040                2045
Asn Lys Leu Asp Glu Ala Lys Leu Ser Gly Asn Glu Ala Thr Val Gly
        2050                2055                2060
Asn Asp Thr Leu Gln Glu Val Cys Phe Thr Ser Glu Lys Val Glu Lys
2065                2070                2075                2080
Leu Pro Gln Cys Leu Leu Val Gln Val Ala Ser Glu Leu Gly Ala Glu
                2085                2090                2095
Ser Asn Thr Thr Ser Pro Glu Lys Leu Glu Leu Asp Ser Phe Gly Ser
                2100                2105                2110
Val Asn Glu Ser Pro Ser Gly Met Gln Gln Ala Arg Cys Val Trp Ser
            2115                2120                2125
Pro Leu Ala Ser Pro Ser Thr Ser Ile Leu Lys Arg Gly Leu Lys Arg
        2130                2135                2140
Ser Gln Glu Asp Glu Ile Ser Pro Val Asn Lys Ile Arg Arg Val Ser
```

```
                2145                2150                2155                2160

Phe Ala Asp Pro Ile Tyr Gln Ala Gly Leu Ala Asp Asp Ile Asp Arg
                2165                2170                2175

Arg Cys Ser Val Val Arg Ser His Ser Ser Asn Ser Ser Pro Ile Ile
                2180                2185                2190

Lys Ser Val Lys Thr Ser Pro Thr Ser His Ser Lys His Asn Thr Thr
                2195                2200                2205

Ser Ala Lys Gly Phe Leu Ser Pro Gly Ser Gln Ser Ser Lys Phe Lys
                2210                2215                2220

Ser Pro Lys Lys Cys Leu Ile Thr Glu Met Ala Gln Glu Ser Met Leu
2225                2230                2235                2240

Ser Pro Thr Glu Ser Val Tyr Pro Ala Leu Val Asn Cys Ala Ala Ser
                2245                2250                2255

Val Asp Ile Ile Leu Pro Gln Ile Thr Ser Asn Met Trp Ala Arg Gly
                2260                2265                2270

Leu Gly Gln Leu Ile Arg Ala Lys Asn Ile Lys Thr Ile Gly Asp Leu
                2275                2280                2285

Ser Thr Leu Thr Ala Ser Glu Ile Lys Thr Leu Pro Ile Arg Ser Pro
                2290                2295                2300

Lys Val Phe Asn Val Lys Lys Ala Leu Arg Val Tyr His Glu Gln Gln
2305                2310                2315                2320

Met Lys Ser Arg Gly Leu Glu Glu Ile Pro Ile Phe Asp Ile Ser Glu
                2325                2330                2335

Lys Ala Val Asn Gly Val Glu Ser Arg Thr Val Ser Thr Asp Glu Glu
                2340                2345                2350

Arg Phe Ala Ser Asp Leu Ile Glu Pro Val Thr Leu Asp Thr Pro Leu
                2355                2360                2365

Ser Lys Asn Leu Val Ala Gln Ile Ser Ala Leu Ala Leu Gln Leu Asp
                2370                2375                2380

Ser Glu Asp Leu Tyr Ser Tyr Thr Gly Ser Gln Leu Phe Glu Met His
2385                2390                2395                2400

Glu Lys Leu Gly Thr Met Ala Asn Ser Ile Ile Arg Asn Leu Gln Ser
                2405                2410                2415

Arg Trp Arg Ser Pro Ala His Glu Asn Ser
                2420                2425

<210> SEQ ID NO 12
<211> LENGTH: 2135
<212> TYPE: PRT
<213> ORGANISM: Fugu rubripes

<400> SEQUENCE: 12

Met Gly Gly Ala Ala Val Arg Trp Val Lys Phe Val Pro Leu Val
1               5                   10                  15

Val His Ser Ala Ser Lys Val Arg Leu Arg Ala Ala Thr Met Glu
                20                  25                  30

Met Gly Met Pro Leu Phe Leu Glu Lys Gln Thr Glu Val Ala Ala Val
            35                  40                  45

Ile Glu Pro Met Met Ser Ser Lys Leu Ile Pro Glu Leu Gln Lys Leu
50                  55                  60

Phe Met Thr Lys Asn Glu Thr Asn Val Leu Lys Leu Trp Pro Leu Phe
65                  70                  75                  80

Val Lys Leu Leu Gly Lys Leu Leu His Lys Gly Gly Pro Phe Ile Asn
                85                  90                  95
```

-continued

```
Ser Leu Leu His Leu Glu Glu Leu Gly Phe Arg Ser Ser Ser Pro Thr
            100                 105                 110
Ile Lys Lys Ile Ala Phe Ile Ala Trp Lys Ser Leu Ile Asp Asn Phe
            115                 120                 125
Ala Leu Asn Pro Asp Ile Leu Cys Ser Ser Lys Arg Met Lys Leu Leu
        130                 135                 140
Met Gln Pro Leu Ala Ser Ile His Val Arg Thr Glu Ala Leu Met Leu
145                 150                 155                 160
Thr Lys Val Glu Val Trp Trp Tyr Leu Val Val Gln Leu Gly Pro Asn
                165                 170                 175
Leu Ser Ser Phe Phe Asp Gln Val Ala Val Pro Leu Leu Gln Cys Thr
            180                 185                 190
Ile Arg Ser Asp Ser Ser Ala Val Pro Gly Thr Pro Ser Arg Pro Thr
        195                 200                 205
Gly Gln Asn Gly Ala Ile Thr Pro Gly Thr Pro Gly Phe Asn Ser Ser
    210                 215                 220
Ala Asn Thr Ser Arg Met Ser Leu Asn Ser Ser Val Gln Ile Thr Pro
225                 230                 235                 240
Thr Phe Pro Lys Ile Gln Leu Leu Gly Leu Glu Met Leu Leu His Tyr
                245                 250                 255
Phe Leu Gly Pro Glu Val Thr Ala Thr Ala Ala Lys Ser Lys Leu Ile
            260                 265                 270
Leu Ser Leu Glu Pro Leu Lys His Pro Leu Leu Ser Ser Ala Gly Ser
        275                 280                 285
Phe Ser Lys His Ala Ala Val Leu Ile Ser Asn Ile Asn Asp Gly Phe
    290                 295                 300
Ile Asn Val Gly Asn Asp Ala Pro Glu Ser Leu Leu Thr Val Leu Trp
305                 310                 315                 320
Thr Thr Leu Val His Phe Val Asn Ser Thr Ile Glu Ser Gly Gly Ser
                325                 330                 335
Lys Lys Asp Arg His Gly Ser Glu Val Leu Thr Leu Met Leu Gln Ala
            340                 345                 350
Leu Gln Ser Ile Val Thr Ser Asn Ala Leu Pro Ala Asp Arg Val Leu
        355                 360                 365
Ile Leu Phe Glu Thr Thr Val Lys Gly Val Thr Gln Arg Val Leu Gly
    370                 375                 380
Ser Ala Ser Tyr Gln Val Gly Lys Met Asp Val Leu Asn Asn Phe Ser
385                 390                 395                 400
Phe His Arg Gln Gly Thr Pro Ala Leu Phe Leu Ile Leu Leu Leu Cys
                405                 410                 415
Asn Ser Asn Met Ile Gly Ala Tyr Val Glu Asp Glu Arg Phe Phe Gln
            420                 425                 430
Cys Leu His Thr Leu Val Ser Cys Gly Leu Ser Gly Pro Thr Ser Pro
        435                 440                 445
Leu Ala Phe Ala Gly Ala Ala Leu Gly Ala Ile Gly Gln Ser Ala Ala
    450                 455                 460
Ser Leu Gln Asn Lys Glu Gln Leu Trp Arg Met Trp Ser Thr Val Val
465                 470                 475                 480
Asn Pro Leu Thr Asp Thr Ile Thr Gln Ser Asn Glu Val Asn Gln Gly
                485                 490                 495
Asp Ala Leu Glu His Asn Phe Ser Ala Ile His Ala Ala Leu Met Phe
            500                 505                 510
Pro Leu Thr His Leu Leu Gly Ala Ala Leu Pro Gln Ala Thr Gln Lys
```

-continued

```
            515                 520                 525
Ala Met Leu Ser Ser Trp Ser Lys Leu Tyr Lys Val Phe Ala Cys Cys
            530                 535                 540

Ser Ala Leu Val Ala Thr Ala Glu Glu Asn Ile Cys Cys Glu Glu Leu
545                 550                 555                 560

Cys Thr Lys Met Ser Thr Val Ile Asp Lys Glu Ala Leu Leu Val Ser
                    565                 570                 575

Met Ser Ala Glu Thr Tyr Ile Ser Ser Ile Leu Gln Val Met Val Glu
                580                 585                 590

Cys Val Asp Phe Ser Pro Tyr Ser Pro Gln Phe Gln Gln Lys Leu Lys
                595                 600                 605

Ser Pro His Thr Pro Val Asn Trp Met Lys Lys Asn Lys Val Leu
            610                 615                 620

Gly Asn Leu Ser Thr Phe Gln Thr Leu Leu Val Gln Cys Leu Gln Val
625                 630                 635                 640

Tyr Leu Glu Asp Thr Val Thr Ser Ser Asp Ala Thr Gly Met Ala Leu
                    645                 650                 655

Val Ser Ile Leu Ser Val Leu Phe Thr Asn Leu Ala Leu Ala Asn Ile
                660                 665                 670

Val Lys Glu Leu Leu Thr Ser Leu Thr His Pro Leu Thr Gln Leu Tyr
                675                 680                 685

Lys His Ala Ala Ser Glu Thr Pro Ser Phe Thr Ser Gln Leu Leu Gly
                690                 695                 700

Lys Leu Glu Lys Leu Leu Gly Asp Val Leu Gly Cys Leu Gln Thr Arg
705                 710                 715                 720

Thr Ala Val Ala Tyr Asp Asp Glu Leu Leu Ala Leu Leu Ser Pro Leu
                    725                 730                 735

Leu Ser Val Leu Phe Leu His Lys Ser Lys His Leu Arg Ser Ser Val
                740                 745                 750

Thr Cys Phe Trp Asn Ser Thr Phe Ala Asn Ser Val Ser Leu Lys Tyr
                755                 760                 765

Pro Asp Glu Ile Arg Pro Val Leu Ser Gln Val Lys Gln Lys Thr Pro
770                 775                 780

Ile Ile Leu Pro Gly Phe Glu Ala Val Asp Val Pro Asp Glu Leu Ser
785                 790                 795                 800

Gly Gln Ser Leu Ser Glu Asn Ser Gln Leu Glu Thr Lys Leu Ser Gly
                    805                 810                 815

Leu Pro Val Ser Ser Val Gly Lys Arg Glu Ser Val Leu Gly Arg Gln
                820                 825                 830

Lys Ala Ser Glu Lys Leu Lys Glu Glu Lys Arg Arg Met Ala Glu
                835                 840                 845

Ile Gln Ala Glu Leu Asp Gln Gln Lys Gln Leu Ala Glu Ala Gln Ala
                850                 855                 860

Lys Ser Ala Ala Arg Ala Glu Gln Ala Glu Glu Leu Lys Leu Lys
865                 870                 875                 880

Met Lys Glu Glu Ala Asn Lys Arg Gln Asp Val Ala Val Asp Ala Glu
                    885                 890                 895

Lys Gln Lys Gln Lys Ile Gln Gln Glu Leu Val Asn Leu Lys Arg Leu
                900                 905                 910

Ser Glu Gln Glu Ile Lys Ser Lys Asn Lys Gln Leu Glu Glu Ala Leu
                915                 920                 925

Ile Ser Arg Thr Lys Ile Glu Glu Glu Ile His Ile Ile Lys Leu Gln
                930                 935                 940
```

-continued

```
Leu Glu Thr Thr Ile Lys Gln Lys Val Thr Ala Asp Ala Glu Leu Gln
945                 950                 955                 960

Ala Leu Arg Asp Lys Ala Asp Gln Ala Glu Lys Leu Arg Lys Asn Ala
            965                 970                 975

Gln Asp Glu Ala Glu Arg Leu Arg Lys Gln Val Ala Glu Glu Thr Gln
                980                 985                 990

Lys Lys Lys His Ala Glu Glu Leu Lys Cys Lys Ser Glu Ala Glu
            995                 1000                1005

Lys Ala Ala Ala Lys Gln Lys Gln Lys Ala Met Glu Asp Leu Gln Lys
        1010                1015                1020

Phe Lys Met Gln Ala Glu Glu Ala Glu Arg Arg Met Lys Gln Ala Glu
1025                1030                1035                1040

Glu Glu Lys Ser Arg Gln Ile Lys Leu Val Glu Glu Val Ala Gln Lys
                1045                1050                1055

Ser Thr Val Thr His Leu Gln Thr Gln Ser Met Leu Tyr Thr Asp Lys
                1060                1065                1070

Thr Thr Lys Leu Glu Glu Ser Leu Lys Lys Glu Gln Gly Thr Val Leu
        1075                1080                1085

Gln Leu Gln Glu Glu Ala Glu Lys Leu Arg Lys Gln Gln Glu Glu Ala
        1090                1095                1100

Asn Arg Ala Arg Glu Gln Ala Glu Lys Glu Leu Glu Thr Trp Arg His
1105                1110                1115                1120

Lys Ala Asn Glu Ala Leu Arg Leu Arg Leu Gln Ala Glu Glu Glu Ala
                1125                1130                1135

Gln Asn Lys Cys Gln Ala Gln Glu Glu Ala Glu Arg Gln Lys Ala Glu
                1140                1145                1150

Ala Glu Arg Asp Ala Lys Asn Arg Ala Arg Ala Glu Asp Ala Ala Leu
            1155                1160                1165

Lys Leu Lys Glu Asn Ala Glu Lys Glu Leu Glu Arg Gln Arg Thr Phe
        1170                1175                1180

Ala Glu Glu Ile Ala Gln Gln Lys Leu Ser Ala Glu Gln Glu Cys Ile
1185                1190                1195                1200

Arg Leu Lys Ser Ala Phe Glu His Ala Asp Gln Gln Arg Ser Leu Leu
                1205                1210                1215

Asp Asn Glu Leu His Arg Leu Lys Asn Glu Val Thr Ala Ala Glu Thr
                1220                1225                1230

Gln Arg Lys Glu Leu Glu Gly Glu Leu Gly Lys Val Arg Ser Glu Met
            1235                1240                1245

Asp Ala Leu Leu Gln Met Lys Val Glu Ala Glu Lys Gln Thr Met Ser
        1250                1255                1260

Thr Ala Glu Lys Ser Lys Gln Leu Leu Glu Thr Glu Ala Leu Arg Met
1265                1270                1275                1280

Lys Gln Leu Ala Glu Asp Ala Ala Arg Leu Arg Ala Val Ala Glu Glu
                1285                1290                1295

Ala Thr Lys Gln Arg Lys Ala Ala Glu Glu Ala Ala Arg Gln Arg
            1300                1305                1310

Ala Glu Ala Glu Lys Met Leu Lys Glu Lys Leu Ala Ala Ile Asn Glu
        1315                1320                1325

Ala Ala Arg Leu Lys Ala Glu Val Glu Ile Ala Leu Lys Ala Lys Glu
        1330                1335                1340

Ala Glu Asn Glu Lys Leu Lys Arg Lys Ala Glu Asp Glu Ala Tyr Gln
1345                1350                1355                1360
```

-continued

```
Arg Lys Leu Leu Glu Asp Gln Ala Ala Gln Tyr Lys Gln Asp Ile Glu
            1365                1370                1375

Glu Lys Leu Thr Ala Val Lys Ser Ser Asp Ala Glu Leu Gln Arg
            1380                1385                1390

Gln Lys Asn Val Leu Glu Glu Thr Leu Arg Gln Lys Asn Leu Val Glu
            1395                1400                1405

Glu Glu Ile Tyr Ile Ile Lys Ile Asn Leu Glu Lys Ala Ser Lys Gly
            1410                1415                1420

Lys Ser Glu Leu Glu Val Glu Leu Lys Lys Leu Lys Asp Ile Ala Glu
1425                1430                1435                1440

Glu Ser Gln Arg Ser Lys Leu Lys Ala Glu Glu Ala Glu Lys Met
            1445                1450                1455

Lys Lys Leu Ala Thr Glu Glu Lys Lys Arg Lys Glu Ser Glu Glu
            1460                1465                1470

Arg Val Lys Ile Ile Thr Gly Ala Glu Lys Glu Ala Ser Arg Gln Trp
            1475                1480                1485

Lys Ala Ala Gln Glu Glu Val Glu Arg Leu Lys Lys Ala Glu Glu
            1490                1495                1500

Ala Asn Lys Asp Lys Asp Lys Ala Thr Gln Glu Ala Glu Glu Gln Ala
1505                1510                1515                1520

Leu Gln Ala Gln Glu Ala Ala Arg Lys Cys Gly Ile Ala Glu Gln Lys
            1525                1530                1535

Leu Asn Asp Ile Leu Ser Lys Asn Arg Gln Asp Ile Leu Ala Glu Glu
            1540                1545                1550

Lys Leu Lys Glu Glu Phe Glu Asn Ala Lys Lys Cys Ala Gln Glu Ala
            1555                1560                1565

Gln Lys Ala Lys Glu Ala Ala Glu Arg Glu Ala Ala Ser Leu Arg Gln
            1570                1575                1580

Lys Ala Glu Glu Ala Glu Lys Gln Arg Lys Ala Ala Glu Asn Glu Ala
1585                1590                1595                1600

Ala Lys Gln Ala Lys Ala Gln Lys Glu Ala Glu Met Leu Lys Lys Glu
            1605                1610                1615

Ala Glu Val Glu Val Ser Lys Arg Thr Ala Ala Gln Ala Thr Ala Leu
            1620                1625                1630

Lys Gln Gln Lys Gln Ala Asp Glu Glu Met Ala Lys Gln Lys Gln Gln
            1635                1640                1645

Ala Glu Glu Ala Leu Lys Gln Lys Ser Leu Val Glu Lys Glu Leu Thr
            1650                1655                1660

Val Val Lys Leu Gln Leu Glu Lys Thr Glu Lys Gln Met Asp Val Leu
1665                1670                1675                1680

Asp Glu Glu Leu Gln Arg Val Lys Gly Glu Val Asn Asp Ala Ile Lys
            1685                1690                1695

Gln Lys Ala Gln Val Glu Glu Leu Ser Lys Val Lys Thr Glu Met
            1700                1705                1710

Ser Glu Leu Leu Lys Leu Lys Leu Lys Ile Glu Glu Glu Asn Arg His
            1715                1720                1725

Leu Leu Gln Lys Asp Lys Asp Lys Met Gln Gln Leu Leu Ala Glu Glu
            1730                1735                1740

Ala Ala Lys Met Lys Leu Leu Ala Glu Asp Ala Ala Arg Leu Ser Val
1745                1750                1755                1760

Glu Ala Thr Glu Leu Ala Arg Gln Arg Gln Met Ala Glu Ser Asp Leu
            1765                1770                1775

Ala Glu Gln Arg Ala Leu Ser Glu Lys Met Leu Lys Glu Lys Met Gln
```

```
                 1780            1785            1790
Val Ser Gln Glu Ala Thr Lys Leu Lys Ala Glu Ala Glu Glu Leu Gln
    1795            1800            1805

Lys Gln Arg Asn Gln Ala Gln Glu Met Ala Asn Lys Leu Gln Lys Asp
    1810            1815            1820

Lys Gln Lys Ile Gln Glu Arg Leu Asp Gln Glu Thr Glu Ala Phe Gln
1825            1830            1835            1840

Lys Ser Leu Glu Ala Glu Gln Lys Arg Gln Leu Glu Ile Ser Ala Glu
            1845            1850            1855

Thr Glu Ala Leu Lys Leu Lys Val Lys Glu Leu Thr Asp Ser Asn Ala
        1860            1865            1870

Lys Ala Glu Glu Glu Val Lys Lys Val Lys Arg Gln Ser Asp Glu Val
    1875            1880            1885

Lys Val Lys Leu Gln Ala Ile Glu Lys Gln Asn Lys Glu Ile Val Leu
    1890            1895            1900

Gln Lys Ser Glu Thr Gln Thr Leu Gln Ser Ser Arg Glu Ala Glu Ser
1905            1910            1915            1920

Leu Arg Lys Ala Val Ala Asp Leu Glu Lys Glu Arg Glu Gln Leu Lys
            1925            1930            1935

Lys Glu Ala Glu Glu Leu Gln Lys Lys Ser Pro Ser Lys Leu Arg Asp
        1940            1945            1950

Leu Glu Ala Leu Met Gly Pro Asp Val Asn His Ser Pro Ser Ser His
    1955            1960            1965

Val Arg Gly Thr Trp Ser Pro Ser Ala Ser Pro Ser Asn Ser Ile Leu
    1970            1975            1980

Lys Lys Ser Gln Lys Arg Pro Leu Glu Asp Glu Ile Pro Ser Pro Leu
1985            1990            1995            2000

Val Lys Ser Arg Arg Val Ser Phe Ala Asp Pro Ile Gln Gln Gln Glu
            2005            2010            2015

Thr Ala Asp Asp Ile Asp Arg Arg Ser Pro Cys Ile Arg Thr Ser Ser
        2020            2025            2030

Pro Arg Lys Pro Arg Asn Ala Ser Ser Ser Gln Pro Lys Ile Ser Glu
    2035            2040            2045

Met Ser Gln Glu Pro Arg Pro Val Ser Arg Asp Cys Val Tyr Pro Ala
    2050            2055            2060

Leu Val Gly Cys Ser Ala Pro Val Glu Ala Val Leu Ser Gln Ile Ser
2065            2070            2075            2080

Ser Asn Met Trp Ser Arg Gly Phe Gly Gln Leu Val Arg Ala Arg Asn
            2085            2090            2095

Ile Lys Thr Val Gly Asp Leu Ser Ala Leu Thr Ala Thr Glu Ile Lys
        2100            2105            2110

Thr Leu Pro Ile Arg Ser Pro Lys Ile Ser Asn Val Lys Lys Ala Leu
    2115            2120            2125

Lys Asn Tyr Glu Gln Gln Val
    2130            2135

<210> SEQ ID NO 13
<211> LENGTH: 1196
<212> TYPE: PRT
<213> ORGANISM: S. cerevisiae

<400> SEQUENCE: 13

Glu Tyr Asp Lys Ile Met Lys Val Val Phe Gln Thr Val Glu Val Ala
1               5                   10                  15
```

-continued

```
Ile Ser Asn Val Asn Leu Ala His Asp Leu Ile Leu Thr Ser Leu Lys
             20                  25                  30
His Leu Pro Glu Asp Arg Lys Asp Gln Thr His Leu Glu Ser Phe Ser
         35                  40                  45
Ser Leu Ile Leu Lys Val Thr Gln Asn Asn Lys Asp Thr Pro Ile Phe
 50                  55                  60
Arg Asp Phe Phe Gly Ala Val Thr Ser Ser Phe Val Tyr Thr Phe Leu
 65                  70                  75                  80
Asp Leu Phe Leu Arg Lys Asn Asp Ser Ser Leu Val Asn Phe Asn Ile
                 85                  90                  95
Gln Ile Ser Lys Val Gly Ile Ser Gln Gly Asn Met Thr Leu Asp Leu
                100                 105                 110
Leu Lys Asp Val Ile Arg Lys Ala Arg Asn Glu Thr Ser Glu Phe Leu
                115                 120                 125
Ile Ile Glu Lys Phe Leu Glu Leu Asp Asp Lys Lys Thr Glu Val Tyr
130                 135                 140
Ala Gln Asn Trp Val Gly Ser Thr Leu Leu Pro Pro Asn Ile Ser Phe
145                 150                 155                 160
Arg Glu Phe Gln Ser Leu Ala Asn Ile Val Asn Lys Val Pro Asn Glu
                165                 170                 175
Asn Ser Ile Glu Asn Phe Leu Asp Leu Cys Leu Lys Leu Ser Phe Pro
                180                 185                 190
Val Asn Leu Phe Thr Leu Leu His Val Ser Met Trp Ser Asn Asn Asn
                195                 200                 205
Phe Ile Tyr Phe Ile Gln Ser Tyr Val Ser Lys Asn Glu Asn Lys Leu
210                 215                 220
Asn Val Asp Leu Ile Thr Leu Leu Lys Thr Ser Leu Pro Gly Asn Pro
225                 230                 235                 240
Glu Leu Phe Ser Gly Leu Leu Pro Phe Leu Arg Arg Asn Lys Phe Met
                245                 250                 255
Asp Ile Leu Glu Tyr Cys Ile His Ser Asn Pro Asn Leu Leu Asn Ser
                260                 265                 270
Ile Pro Asp Leu Asn Ser Asp Leu Leu Lys Leu Leu Pro Arg Ser
                275                 280                 285
Arg Ala Ser Tyr Phe Ala Ala Asn Ile Lys Leu Phe Lys Cys Ser Glu
                290                 295                 300
Gln Leu Thr Leu Val Arg Trp Leu Leu Lys Gly Gln Gln Leu Glu Gln
305                 310                 315                 320
Leu Asn Gln Asn Phe Ser Glu Ile Glu Asn Val Leu Gln Asn Ala Ser
                325                 330                 335
Asp Ser Glu Leu Glu Lys Ser Glu Ile Ile Arg Glu Leu Leu His Leu
                340                 345                 350
Ala Met Ala Asn Pro Ile Glu Pro Leu Phe Ser Gly Leu Leu Asn Phe
                355                 360                 365
Cys Ile Lys Asn Asn Met Ala Asp His Leu Asp Glu Phe Cys Gly Asn
                370                 375                 380
Met Thr Ser Glu Val Leu Phe Lys Ile Ser Pro Glu Leu Leu Leu Lys
385                 390                 395                 400
Leu Leu Thr Tyr Lys Glu Lys Pro Asn Gly Lys Leu Leu Ala Ala Val
                405                 410                 415
Ile Glu Lys Ile Glu Asn Gly Asp Asp Asp Tyr Ile Leu Glu Leu Leu
                420                 425                 430
Glu Lys Ile Ile Ile Gln Lys Glu Ile Gln Ile Leu Glu Lys Leu Lys
```

-continued

```
            435                 440                 445
Glu Pro Leu Leu Val Phe Phe Leu Asn Pro Val Ser Ser Asn Met Gln
450                 455                 460

Lys His Lys Lys Ser Thr Asn Met Leu Arg Glu Leu Val Leu Leu Tyr
465                 470                 475                 480

Leu Thr Lys Pro Leu Ser Arg Ser Ala Ala Lys Lys Phe Phe Ser Met
                485                 490                 495

Leu Ile Ser Ile Leu Pro Pro Asn Pro Asn Tyr Gln Thr Ile Asp Met
                500                 505                 510

Val Asn Leu Leu Ile Asp Leu Ile Lys Ser His Asn Arg Lys Phe Lys
                515                 520                 525

Asp Lys Arg Thr Tyr Asn Ala Thr Leu Lys Thr Ile Gly Lys Trp Ile
530                 535                 540

Gln Glu Ser Gly Val Val His Gln Gly Asp Ser Ser Lys Glu Ile Glu
545                 550                 555                 560

Ala Ile Pro Asp Thr Lys Ser Met Tyr Ile Pro Cys Glu Gly Ser Glu
                565                 570                 575

Asn Lys Leu Ser Asn Leu Gln Arg Lys Val Asp Ser Gln Asp Ile Gln
                580                 585                 590

Val Pro Ala Thr Gln Gly Met Lys Glu Pro Pro Ser Ile Gln Ile
                595                 600                 605

Ser Ser Gln Ile Ser Ala Lys Asp Ser Asp Ser Ile Ser Leu Lys Asn
610                 615                 620

Thr Ala Ile Met Asn Ser Ser Gln Gln Glu Ser His Ala Asn Arg Ser
625                 630                 635                 640

Arg Ser Ile Asp Asp Glu Thr Leu Glu Glu Val Asp Asn Glu Ser Ile
                645                 650                 655

Arg Glu Ile Asp Gln Gln Met Lys Ser Thr Gln Leu Asp Lys Asn Val
                660                 665                 670

Ala Asn His Ser Asn Ile Cys Ser Thr Lys Ser Asp Glu Val Asp Val
                675                 680                 685

Thr Glu Leu His Glu Ser Ile Asp Thr Gln Ser Ser Glu Val Asn Ala
                690                 695                 700

Tyr Gln Pro Ile Glu Val Leu Thr Ser Glu Leu Lys Ala Val Thr Asn
705                 710                 715                 720

Arg Ser Ile Lys Thr Asn Pro Asp His Asn Val Asn Ser Asp Asn
                725                 730                 735

Pro Leu Lys Arg Pro Ser Lys Glu Thr Pro Thr Ser Glu Asn Lys Arg
                740                 745                 750

Ser Lys Gly His Glu Thr Met Val Asp Val Leu Val Ser Glu Glu Gln
                755                 760                 765

Ala Val Ser Pro Ser Ser Asp Val Ile Cys Thr Asn Ile Lys Ser Ile
                770                 775                 780

Ala Asn Glu Glu Ser Ser Leu Ala Leu Arg Asn Ser Ile Lys Val Glu
785                 790                 795                 800

Thr Asn Cys Asn Glu Asn Ser Leu Asn Val Thr Leu Asp Leu Asp Gln
                805                 810                 815

Gln Thr Ile Thr Lys Glu Asp Gly Lys Gly Gln Val Glu His Val Gln
                820                 825                 830

Arg Gln Glu Asn Gln Glu Ser Met Asn Lys Ile Asn Ser Lys Ser Phe
                835                 840                 845

Thr Gln Asp Asn Ile Ala Gln Tyr Lys Ser Val Lys Lys Ala Arg Pro
                850                 855                 860
```

```
Asn Asn Glu Gly Glu Asn Asn Asp Tyr Ala Cys Asn Val Glu Gln Ala
865                 870                 875                 880

Ser Pro Val Arg Asn Glu Val Pro Gly Asp Gly Ile Gln Ile Pro Ser
                885                 890                 895

Gly Thr Ile Leu Leu Asn Ser Ser Lys Gln Thr Glu Lys Ser Lys Val
            900                 905                 910

Asp Asp Leu Arg Ser Asp Glu Asp Glu His Gly Thr Val Ala Gln Glu
        915                 920                 925

Lys His Gln Val Gly Ala Ile Asn Ser Arg Asn Lys Asn Asn Asp Arg
    930                 935                 940

Met Asp Ser Thr Pro Ile Gln Gly Thr Glu Glu Ser Arg Glu Val
945                 950                 955                 960

Val Met Thr Glu Glu Gly Ile Asn Val Arg Leu Glu Asp Ser Gly Thr
            965                 970                 975

Cys Glu Leu Asn Lys Asn Leu Lys Gly Pro Leu Lys Gly Asp Lys Asp
            980                 985                 990

Ala Asn Ile Asn Asp Asp Phe Val Pro Val Glu Glu Asn Val Arg Asp
        995                 1000                1005

Glu Gly Phe Leu Lys Ser Met Glu His Ala Val Ser Lys Glu Thr Gly
    1010                1015                1020

Leu Glu Glu Gln Pro Glu Val Ala Asp Ile Ser Val Leu Pro Glu Ile
1025                1030                1035                1040

Arg Ile Pro Ile Phe Asn Ser Leu Lys Met Gln Gly Ser Lys Ser Gln
            1045                1050                1055

Ile Lys Glu Lys Leu Lys Lys Arg Leu Gln Arg Asn Glu Leu Met Pro
            1060                1065                1070

Pro Asp Ser Pro Pro Arg Met Thr Glu Asn Thr Asn Ile Asn Ala Gln
        1075                1080                1085

Asn Gly Leu Asp Thr Val Pro Lys Thr Ile Gly Gly Lys Glu Lys His
    1090                1095                1100

His Glu Ile Gln Leu Gly Gln Ala His Thr Glu Ala Asp Gly Glu Pro
1105                1110                1115                1120

Leu Leu Gly Gly Asp Gly Asn Glu Asp Ala Thr Ser Arg Glu Ala Thr
            1125                1130                1135

Pro Ser Leu Lys Val His Phe Phe Ser Lys Lys Ser Arg Arg Leu Val
            1140                1145                1150

Ala Arg Leu Arg Gly Phe Thr Pro Gly Asp Leu Asn Gly Ile Ser Val
            1155                1160                1165

Glu Glu Arg Arg Asn Leu Arg Ile Glu Leu Leu Asp Phe Met Met Arg
    1170                1175                1180

Leu Glu Tyr Tyr Ser Asn Arg Asp Asn Asp Met Asn
1185                1190                1195
```